US007799773B2

(12) United States Patent
Bamford et al.

(10) Patent No.: US 7,799,773 B2
(45) Date of Patent: *Sep. 21, 2010

(54) BENZAZEPINE DERIVATIVES FOR THE TREATMENT OF NEUROLOGICAL DISORDERS

(75) Inventors: Mark James Bamford, Harlow (GB); David Kenneth Dean, Harlow (GB); Sanjeet Singh Sehmi, Harlow (GB); David Matthew Wilson, Harlow (GB); Jason Witherington, Harlow (GB)

(73) Assignee: Glaxo Group Limited, Greenford, Middlesex (GB)

(*) Notice: Subject to any disclaimer, the term of this patent is extended or adjusted under 35 U.S.C. 154(b) by 0 days.

This patent is subject to a terminal disclaimer.

(21) Appl. No.: 12/339,145

(22) Filed: Dec. 19, 2008

(65) Prior Publication Data

US 2009/0105226 A1 Apr. 23, 2009

Related U.S. Application Data

(63) Continuation of application No. 10/539,385, filed as application No. PCT/EP03/14556 on Dec. 18, 2003.

(30) Foreign Application Priority Data

Dec. 20, 2002 (GB) .................. 0229820.6
Jun. 2, 2003 (GB) .................. 0312607.5

(51) Int. Cl.
*A61P 7/00* (2006.01)
*A61K 31/55* (2006.01)
*C07D 223/16* (2006.01)

(52) U.S. Cl. .................. 514/217.01; 540/594
(58) Field of Classification Search ............ 514/217.01; 540/594

See application file for complete search history.

(56) References Cited

U.S. PATENT DOCUMENTS

| | | | |
|---|---|---|---|
| 3,393,192 A | 7/1968 | Walter et al. | |
| 4,206,210 A | 6/1980 | Holden | 424/244 |
| 4,210,749 A | 7/1980 | Shetty | |
| 4,233,217 A | 11/1980 | Shetty | 260/239 |
| 4,843,081 A | 6/1989 | Regan et al. | |
| 4,959,374 A | 9/1990 | Berge | |
| 5,175,157 A | 12/1992 | Psiorz et al. | |
| 5,364,791 A | 11/1994 | Vegeto et al. | |
| 5,874,534 A | 2/1999 | Vegeto et al. | |
| 5,935,934 A | 8/1999 | Vegeto et al. | |
| 6,218,385 B1 | 4/2001 | Adam et al. | 514/217.01 |
| 7,229,986 B2 | 6/2007 | Ishihara et al. | 514/217.01 |
| 2003/0207863 A1 | 11/2003 | Fukumoto et al. | 514/215 |
| 2004/0053826 A1 | 3/2004 | Matsumoto et al. | |
| 2004/0063699 A1 | 4/2004 | Tarui et al. | |
| 2006/0040918 A1 | 2/2006 | Bamford et al. | 514/217.01 |
| 2006/0089347 A1 | 4/2006 | Gadski et al. | 514/212.07 |
| 2006/0116364 A1 | 6/2006 | Hamaoka et al. | 514/217.01 |
| 2006/0217372 A1 | 9/2006 | Blanco-Pillado et al. | 514/227.5 |
| 2007/0060566 A1 | 3/2007 | Bailey et al. | 514/217.01 |
| 2007/0185089 A1 | 8/2007 | Bamford et al. | 514/217.02 |
| 2007/0208005 A1 | 9/2007 | Parr et al. | 514/217.01 |
| 2007/0232590 A1 | 10/2007 | Bamford et al. | 514/217.01 |
| 2007/0299056 A1 | 12/2007 | Bamford et al. | 514/217.02 |
| 2008/0009479 A1 | 1/2008 | Heightman et al. | 514/217.01 |

FOREIGN PATENT DOCUMENTS

| | | |
|---|---|---|
| CA | 2197789 | 2/1997 |
| DE | 2 207 430 | 7/1981 |
| DE | 44 29 079 | 2/1996 |
| DE | 195 30 996 | 2/1997 |
| EP | 0 292 840 | 11/1988 |
| EP | 0347672 | 12/1989 |
| EP | 0 382 628 | 5/1994 |
| EP | 0 487 071 | 7/1995 |
| EP | 0 634 401 | 8/1997 |
| EP | 0 612 741 B1 | 6/1998 |
| EP | 1 148 054 | 10/2001 |
| EP | 1 283 199 | 2/2003 |
| EP | 1 331 010 | 7/2003 |
| FR | 2171879 | 9/1973 |
| GB | 1 268 243 | 3/1972 |
| JP | 63094239 | 4/1988 |
| JP | 5 239024 | 9/1993 |
| JP | 2001226269 | 8/2001 |
| WO | WO 91/19698 | 12/1991 |
| WO | WO 93/00094 | 1/1993 |
| WO | WO 93/03015 | 2/1993 |

(Continued)

OTHER PUBLICATIONS

Austin et al., "Novel 2,3,4,5-Tetrahydro-1*H*-3-benzazepines with High Affinity and Selectivity for the Dopamine $D_3$ Receptor," Bioorganic & Medicinal Chemistry Letters 10:2553-2555 (2000).
Evans et al., "Kinetics of the Aqueous Periodate Oxidation of Aliphatic Disulfides with Thioethers," J. Org. Chem 55:2580-2586 (1990).
Giovannini et al., "Effects of histamine $H_3$ receptor agonists and antagonists on cognitive performance and scopolamine-induced amnesia," Behavioural Brain Res. 104:147-155 (1999).
Leurs et al., "Therapeutic potential of histamine $H_3$ receptor agonists and antagonists," TiPS 19:177-183 (May 1998).
Lovenberg et al., "Cloning and Functional Expression of the Human Histamine $H_3$ Receptor," Molecular Pharmacology 55:1101-1107 (1999).
Niiyama et al., "Structure-Activity Relationships of 2-Substituted 5,7-Diarylcyclopenteno[1,2-*b*]pyridine-6-carboxylic Acids as a Novel Class of Endothelin Receptor Antagonists," Bioorganic & Medicinal Chemistry Letters 12:3041-3045 (2002).

(Continued)

*Primary Examiner*—Brenda L Coleman
(74) *Attorney, Agent, or Firm*—Duke M. Fitch; Kathryn L. Sieburth; Lorraine Ling

(57) ABSTRACT

The present invention relates to novel benzazepine derivatives having pharmacological activity, processes for their preparation, to compositions containing them and to their use in the treatment of neurological and psychiatric disorders.

19 Claims, No Drawings

FOREIGN PATENT DOCUMENTS

| | | |
|---|---|---|
| WO | WO 93/04686 | 3/1993 |
| WO | WO 93/10089 | 5/1993 |
| WO | WO 93/16997 | 9/1993 |
| WO | WO 94/19315 | 9/1994 |
| WO | WO 95/13075 | 5/1995 |
| WO | WO 95/14028 | 5/1995 |
| WO | WO 96/05194 A1 | 2/1996 |
| WO | WO 98/06701 | 2/1998 |
| WO | WO 98/31356 | 7/1998 |
| WO | WO 99/26919 | 3/1999 |
| WO | WO 99/25709 | 5/1999 |
| WO | WO 99/28314 | 6/1999 |
| WO | WO 99/38862 | 8/1999 |
| WO | WO 99/42462 | 8/1999 |
| WO | WO 99/54310 | 10/1999 |
| WO | WO 99/55677 | 11/1999 |
| WO | WO 00/06254 | 2/2000 |
| WO | WO 00/08022 | 2/2000 |
| WO | WO 00/21951 | 4/2000 |
| WO | WO 00/23437 | 4/2000 |
| WO | WO 00/38618 | 7/2000 |
| WO | WO 00/78724 | 12/2000 |
| WO | WO 01/03680 | 1/2001 |
| WO | WO 01/34571 | 5/2001 |
| WO | WO 01/55118 | 8/2001 |
| WO | WO 01/85695 | 11/2001 |
| WO | WO 01/87834 | 11/2001 |
| WO | WO 02/02530 | 1/2002 |
| WO | WO 02/14513 | 2/2002 |
| WO | WO 02/15934 | 2/2002 |
| WO | WO 02/40451 | 5/2002 |
| WO | WO 02/40471 | 5/2002 |
| WO | WO 02/057258 | 7/2002 |
| WO | WO 03/041641 | 5/2003 |
| WO | WO 03/075858 | 9/2003 |
| WO | WO 03/086306 | 10/2003 |
| WO | WO 03/090751 | 11/2003 |
| WO | WO 2003/091258 | 11/2003 |
| WO | WO 2004/018432 | 3/2004 |
| WO | WO 2004/026305 | 4/2004 |
| WO | WO 2004/035544 A1 | 4/2004 |
| WO | WO 2004/037788 | 5/2004 |
| WO | WO 2004/058682 A1 | 7/2004 |
| WO | WO 2004/069244 | 8/2004 |
| WO | WO 2005/014479 A2 | 2/2005 |
| WO | WO 2005/039591 A1 | 5/2005 |
| WO | WO 2005/058328 A1 | 6/2005 |

OTHER PUBLICATIONS

Onodera and Watanabe, "Histamine $H_3$ Antagonists as Potential Therapeutics in the CNS," ed Leurs and Timmerman, pp. 255-267, Elsevier Science B.V. (1998).

Schlicker et al., "Modulation of neurotransmitter release via histamine $H_3$ heteroreceptors," Fundam Clin Pharmacol 8:128-137 (1994).

Riley et al., "The Reaction of Protein Amino Groups with Methyl 5-Iodopyridine-2-carboximidate . . . ," Biochemical Journal 131(4):625-635 (1973).

Medhurst et al., *Biochemical Pharmacology*, 73, pp. 1182-1194 (2007).

Southam et al., *Psychopharmacology*, 201, pp. 483-494 (2009).

Medhurst et al., *The Journal of Pharmacology and Experimental Therapeutics*, 321(3), pp. 1032-1045 (2007).

Medhurst et al., *Pain*, 138, pp. 61-69 (2008).

Pérez-Garcia et al., *Psychopharmacology*, 142, pp. 215-220 (1999).

Fox et al., *The Journal of Pharmacology and Experimental Therapeutics*, 313(1), pp. 176-190 (2005).

Wijtmans et al., *Expert Opin. Investig. Drugs*, 16(7), pp. 967-985 (2007).

Celanire et al., *DDT*, 10(23/24), pp. 1613-1627 (2005).

Sander et al., *Biol. Pharm. Bull.*, 31(12), pp. 2163-2181 (2008).

BENZAZEPINE DERIVATIVES FOR THE TREATMENT OF NEUROLOGICAL DISORDERS

CROSS-REFERENCE TO RELATED APPLICATIONS

This application is a Continuation of U.S. application Ser. No. 10/539,385 filed on Jun. 16, 2005; which is a U.S. National Phase Application of International Application No. PCT/EP2003/014556 filed on Dec. 18, 2003; which claims priority from Application No. GB0312607.5 filed on Jun. 2, 2003 and Application No. GB0229820.6 filed on Dec. 20, 2002; all of which are incorporated herein by reference in their entirety.

FIELD OF THE INVENTION

The present invention relates to novel benzazepine derivatives having pharmacological activity, processes for their preparation, to compositions containing them and to their use in the treatment of neurological and psychiatric disorders.

BACKGROUND OF THE INVENTION

JP 2001226269 and WO 00/23437 (Takeda Chem Ind Ltd) describe a series of benzazepine derivatives which are claimed to be useful in the treatment of obesity. DE 2207430, U.S. Pat. No. 4,210,749 and FR 2171879 (Pennwalt Corp) and GB 1268243 (Wallace and Tiernan Inc) all describe a series of benzazepine derivatives which are claimed as being antagonists for narcotics (such as morphine or codeine) and also anti-histamines and anticholinergic agents. WO 02/14513 (Takeda Chem Ind Ltd) describe a series of benzazepine derivatives with GPR12 activity which are claimed to be useful in the treatment of attention deficit disorder, narcolepsy or anxiety. WO 02/02530 (Takeda Chem Ind Ltd) describe a series of benzazepine derivatives as GPR14 antagonists which are claimed to be useful in the treatment of hypertension, atherosclerosis and cardiac infarction. WO 01/03680 (Isis Innovation Ltd) describe a series of benzazepine derivatives which are claimed as effective agents in the preparation of cells for transplantation in addition to the inhibition of diseases such as diabetes. WO 00/21951 (SmithKline Beecham plc) discloses a series of tetrahydrobenzazepine derivatives as modulators of dopamine D3 receptors which are claimed to be useful as antipsychotic agents. WO 01/87834 (Takeda Chem Ind Ltd) describe a series of benzazepine derivatives as MCH antagonists which are claimed to be useful in the treatment of obesity. WO 02/15934 (Takeda Chem Ind Ltd) describe a series of benzazepine derivatives as urotensin II receptor antagonists which are claimed to be useful in the treatment of neurodegenerative disorders.

The histamine H3 receptor is predominantly expressed in the mammalian central nervous system (CNS), with minimal expression in peripheral tissues except on some sympathetic nerves (Leurs et al., (1998), Trends Pharmacol. Sci. 19, 177-183). Activation of H3 receptors by selective agonists or histamine results in the inhibition of neurotransmitter release from a variety of different nerve populations, including histaminergic and cholinergic neurons (Schlicker et al., (1994), Fundam. Clin. Pharmacol. 8, 128-137). Additionally, in vitro and in vivo studies have shown that H3 antagonists can facilitate neurotransmitter release in brain areas such as the cerebral cortex and hippocampus, relevant to cognition (Onodera et al., (1998), In: The Histamine H3 receptor, ed Leurs and Timmerman, pp 255-267, Elsevier Science B.V.). Moreover, a number of reports in the literature have demonstrated the cognitive enhancing properties of H3 antagonists (e.g. thioperamide, clobenpropit, ciproxifan and GT-2331) in rodent models including the five choice task, object recognition, elevated plus maze, acquisition of novel task and passive avoidance (Giovanni et al., (1999), Behav. Brain Res. 104, 147-155). These data suggest that novel H3 antagonists and/or inverse agonists such as the current series could be useful for the treatment of cognitive impairments in neurological diseases such as Alzheimer's disease and related neurodegenerative disorders.

SUMMARY OF THE INVENTION

The present invention provides, in a first aspect, a compound of formula (I) or a pharmaceutically acceptable salt thereof:

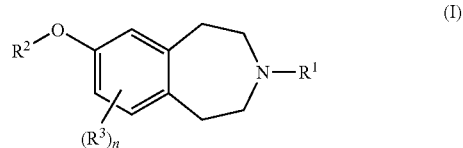

(I)

wherein:

$R^1$ represents —$C_{3-7}$ cycloalkyl optionally substituted by $C_{1-3}$ alkyl;

$R^2$ represents hydrogen, —$C_{1-6}$ alkyl, —X—$C_{3-8}$ cycloalkyl, —X-aryl, —X-heterocyclyl, —X-heteroaryl, —X—$C_{3-8}$ cycloalkyl-Y—$C_{3-8}$ cycloalkyl, —X—$C_{3-8}$ cycloalkyl-Y-aryl, —X—$C_{3-8}$ cycloalkyl-Y-heteroaryl, —X—$C_{3-8}$ cycloalkyl-Y-heterocyclyl, —X-aryl-Y—$C_{3-8}$ cycloalkyl, —X-aryl-Y-aryl, —X-aryl-Y-heteroaryl, —X-aryl-Y-heterocyclyl, —X-heteroaryl-Y—$C_{3-8}$ cycloalkyl, —X-heteroaryl-Y-aryl, —X-heteroaryl-Y-heteroaryl, —X-heteroaryl-Y-heterocyclyl, —X-heterocyclyl-Y—$C_{3-8}$ cycloalkyl, —X-heterocyclyl-Y-aryl, —X-heterocyclyl-Y-heteroaryl, —X-heterocyclyl-Y-heterocyclyl;

X represents a bond or $C_{1-6}$ alkyl;

Y represents a bond, $C_{1-6}$ alkyl, CO, CO$C_{2-6}$ alkenyl, O or SO$_2$;

$R^3$ represents halogen, $C_{1-6}$ alkyl, $C_{1-6}$ alkoxy, cyano, amino or trifluoromethyl;

n is 0, 1 or 2;

wherein said alkyl, cycloalkyl, aryl, heteroaryl and heterocyclyl groups of $R^2$ may be optionally substituted by one or more substituents (eg. 1, 2 or 3) which may be the same or different, and which are selected from the group consisting of halogen, hydroxy, cyano, nitro, =O, trifluoromethyl, trifluoromethoxy, fluoromethoxy, difluoromethoxy, $C_{1-6}$ alkyl, pentafluoroethyl, $C_{1-6}$ alkoxy, aryl$C_{1-6}$ alkoxy, $C_{1-6}$ alkylthio, $C_{1-6}$ alkoxy$C_{1-6}$ alkyl, $C_{3-7}$ cycloalkyl$C_{1-6}$ alkoxy, $C_{1-6}$ alkanoyl, $C_{1-6}$ alkoxycarbonyl, $C_{1-6}$ alkylsulfonyl, $C_{1-6}$ alkylsulfinyl, $C_{1-6}$ alkylsulfonyloxy, $C_{1-6}$ alkylsulfonyl$C_{1-6}$ alkyl, sulfonyl, arylsulfonyl, arylsulfonyloxy, arylsulfonyl$C_{1-6}$ alkyl, aryloxy, $C_{1-6}$ alkylsulfonamido, $C_{1-6}$ alkylamino, $C_{1-6}$ alkylamido, —$R^4$, —CO$_2R^4$, —COR$^4$, $C_{1-6}$ alkylsulfonamidoC$_{1-6}$ alkyl, $C_{1-6}$ alkylamido$C_{1-6}$ alkyl, arylsulfonamido, arylcarboxamido, arylsulfonamido$C_{1-6}$ alkyl, arylcarboxamido$C_{1-6}$ alkyl, aroyl, aroyl$C_{1-6}$ alkyl, aryl$C_{1-6}$ alkanoyl, or a group —NR$^5$R$^6$, —$C_{1-6}$ alkyl-NR$^5$R$^6$, —$C_{3-8}$ cycloalkyl- NR⁵R⁶, —CONR⁵R⁶, —NR⁵COR⁶, —NR⁵SO₂R⁶, —OCONR⁵R⁶, —NR⁵CO₂R⁶, —NR⁴CONR⁵R⁶ or —SO₂NR⁵R⁶ (wherein R⁴, R⁵ and R⁶ independently represent hydrogen, $C_{1-6}$ alkyl, —$C_{3-8}$ cycloalkyl, —$C_{1-6}$ alkyl-$C_{3-8}$ cycloalkyl, aryl, heterocyclyl or heteroaryl or —NR⁵R⁶ may represent a nitrogen containing heterocyclyl group, wherein said R⁴, R⁵ and R⁶ groups may be optionally substituted by one or more substituents (eg. 1, 2 or 3) which may be the same or different, and which are selected from the group consisting of halogen, hydroxy, $C_{1-6}$ alkyl, $C_{1-6}$ alkoxy, cyano, amino, =O or trifluoromethyl); or solvates thereof.

In one particular aspect of the present invention, there is provided a compound of formula (I) as defined above wherein:

R² represents —$C_{1-6}$ alkyl, —X—$C_{3-8}$ cycloalkyl, —X-aryl, —X-heterocyclyl, —X-heteroaryl, —X—$C_{3-8}$ cycloalkyl-Y—$C_{3-8}$ cycloalkyl, —X—$C_{3-8}$ cycloalkyl-Y-aryl, —X—$C_{3-8}$ cycloalkyl-Y-heteroaryl, —X—$C_{3-8}$ cycloalkyl-Y-heterocyclyl, —X-aryl-Y—$C_{3-8}$ cycloalkyl, —X-aryl-Y-aryl, —X-aryl-Y-heteroaryl, —X-aryl-Y-heterocyclyl, —X-heteroaryl-Y—$C_{3-8}$ cycloalkyl, —X-heteroaryl-Y-aryl, —X-heteroaryl-Y-heteroaryl, —X-heteroaryl-Y-heterocyclyl, —X-heterocyclyl-Y—$C_{3-8}$ cycloalkyl, —X-heterocyclyl-Y-aryl, —X-heterocyclyl-Y-heteroaryl, —X-heterocyclyl-Y-heterocyclyl; and Y represents a bond, $C_{1-6}$ alkyl, CO, O or SO₂; and R⁴, R⁵ and R⁶ independently represent hydrogen, $C_{1-6}$ alkyl, —$C_{3-8}$ cycloalkyl, aryl, heterocyclyl or heteroaryl or —NR⁵R⁶ may represent a nitrogen containing heterocyclyl group.

DETAILED DESCRIPTION OF THE INVENTION

A specific set of compounds of formula (I) which may be mentioned are those wherein R² represents —X-heterocyclyl, —X-heterocyclyl-Y—$C_{3-8}$ cycloalkyl, —X-heterocyclyl-Y-aryl, —X-heterocyclyl-Y-heteroaryl or —X-heterocyclyl-Y-heterocyclyl and said heterocyclyl groups are attached to X via a carbon atom.

Alkyl groups, whether alone or as part of another group, may be straight chain or branched and the groups alkoxy and alkanoyl shall be interpreted similarly. Alkyl moieties are more preferably $C_{1-4}$ alkyl, eg. methyl or ethyl. The term 'halogen' is used herein to describe, unless otherwise stated, a group selected from fluorine, chlorine, bromine or iodine.

References to 'aryl' include references to monocyclic carbocyclic aromatic rings (eg. phenyl) and bicyclic carbocyclic aromatic rings (e.g. naphthyl) or carbocyclic benzofused rings (eg. $C_{3-8}$ cycloalkyl fused to a phenyl ring, such as dihydroindenyl or tetrahydronaphthalenyl).

The term "heterocyclyl" is intended to mean a 4-7 membered monocyclic saturated or partially unsaturated aliphatic ring or a 4-7 membered saturated or partially unsaturated aliphatic ring fused to a benzene ring containing 1 to 3 heteroatoms selected from oxygen, nitrogen or sulphur. Suitable examples of such monocyclic rings include pyrrolidinyl, piperidinyl, piperazinyl, morpholinyl, thiomorpholinyl, tetrahydrofuranyl, tetrahydropyranyl, diazepanyl, azepanyl, imidazolidinyl, isothiazolidinyl, oxazolidinyl, pyrrolidinone and tetrahydro-oxazepinyl. Suitable examples of benzofused heterocyclic rings include indolinyl, isoindolinyl, benzodioxolyl, dihydroisoindole, dihydrobenzofuranyl, dihydrobenzothiopyranyl and dihydroisoquinolinyl.

The term "nitrogen containing heterocyclyl" is intended to represent any heterocyclyl group as defined above which contains a nitrogen atom.

The term "heteroaryl" is intended to mean a 5-7 membered monocyclic aromatic or a fused 8-11 membered bicyclic aromatic ring containing 1 to 3 heteroatoms selected from oxygen, nitrogen and sulphur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridyl and tetrahydropyranyl. Suitable examples of such fused aromatic rings include benzofused aromatic rings such as quinolinyl, isoquinolinyl, quinazolinyl, quinoxalinyl, cinnolinyl, naphthyridinyl, indolyl, indazolyl, furopyridinyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like.

Preferably, R¹ represents unsubstituted —$C_{3-7}$ cycloalkyl (eg. cyclobutyl, cyclopentyl or cyclohexyl). Also preferably, R¹ represents —$C_{3-7}$ cycloalkyl (eg. cyclopentyl) substituted by a $C_{1-3}$ alkyl (eg. methyl) group.

Most preferably, R¹ represents unsubstituted cyclobutyl or cyclopentyl, especially unsubstituted cyclobutyl.

Preferably, R² represents
hydrogen;
—$C_{1-6}$ alkyl (eg. methyl or propyl) optionally substituted by a —CO₂R⁴ or —CONR⁵R⁶ group;
—X—$C_{3-8}$ cycloalkyl-Y-heterocyclyl (eg. —X-cyclohexyl-Y-morpholinyl);
—X-aryl (eg. —X-phenyl) optionally substituted by one or two halogen (eg. fluorine, iodine or chlorine), $C_{1-6}$ alkyl (eg. methyl), $C_{1-6}$ alkoxy (eg. methoxy), —CO₂R⁴, —CONR⁵R⁶, —NR⁵COR⁶, —SO₂NR⁵R⁶ or cyano groups;
—X-aryl-Y-heterocyclyl (eg. —X-phenyl-Y-piperazinyl, —X-phenyl-Y-pyrrolidinyl or —X-phenyl-Y-morpholinyl) optionally substituted by one or two =O, halogen (eg. fluorine) or R⁴ groups;
—X-heteroaryl (eg. —X-pyridinyl, —X-pyrazinyl, —X-pyrimidinyl, —X-pyridazinyl, —X-quinolinyl, —X-pyrrolopyridinyl, —X-furopyridinyl, —X-naphthyridinyl, —X-thiazolyl or —X-thienyl) optionally substituted by one or two halogen (eg. bromine or iodine), $C_{1-6}$ alkyl (eg. methyl), $C_{1-6}$ alkoxy (eg. methoxy or ethoxy), cyano, nitro, —OR⁴, —COR⁴, —CO₂R⁴, —NR⁵R⁶, —NR⁵COR⁶, —CONR⁵R⁶ or =O groups;
—X-heteroaryl-Y-aryl (eg. —X-pyrazinyl-Y-phenyl) optionally substituted by a $C_{1-6}$ alkylsulfonyl (eg. —SO₂Me) or —NR⁵COR⁶ group;
—X-heteroaryl-Y-heteroaryl (eg. —X-pyridinyl-Y-pyrazolyl, —X-pyridinyl-Y-oxadiazolyl, —X-pyridinyl-Y-oxazolyl or —X-pyridinyl-Y-pyrazinyl) optionally substituted by a $C_{1-6}$ alkyl (eg. methyl) group;
—X-heteroaryl-Y-heterocyclyl (eg. —X-pyridinyl-Y-morpholinyl, —X-pyridinyl-Y-pyrrolidinyl, —X-pyridinyl-Y-piperidinyl, —X-pyridinyl-Y-thiomorpholinyl, —X-pyridinyl-Y-tetrahydropyranyl, —X-pyridinyl-Y-imidazolidinyl, —X-pyridinyl-Y-tetrahydro-oxazepinyl, —X-pyridinyl-Y-azetidinyl, —X-pyridinyl-Y-oxazolidinyl, —X-pyridinyl-Y-isothiazolidinyl, —X-pyrazinyl-Y-morpholinyl, —X-pyrazinyl-Y-piperidinyl, —X-pyrazinyl-Y-pyrrolidinyl, —X-pyrazinyl-Y-thiomorpholinyl, —X-pyrazinyl-Y-oxazolidinyl, —X-pyrazinyl-Y-azetidinyl, —X-pyrazinyl-Y-tetrahydropyranyl or —X-pyridazinyl-Y-morpholinyl) optionally substituted by one or two =O, $C_{1-6}$ alkyl (eg. methyl), —$OR^4$ or halogen (eg. chlorine or bromine) groups;
- —X-heterocyclyl (eg. —X-piperidinyl or —X-pyrrolidinyl) optionally substituted by a $C_{1-6}$ alkylsulfonyl (eg. —$SO_2Me$), $C_{1-6}$ alkoxycarbonyl (eg. —CO—$CH_2CH_2OMe$), —$CO_2R^4$, —$COR^4$ or —$COR^5R^6$ group;
- —X-heterocyclyl-Y-aryl (eg. —X-piperidinyl-Y-phenyl or —X-pyrrolidinyl-Y-phenyl) optionally substituted by a halogen (eg. fluorine), cyano, $C_{1-6}$ alkylsulfonyl (eg —$SO_2Me$), $R^4$ or —$CONR^5R^6$ group;
- —X-heterocyclyl-Y-heterocyclyl (eg. —X-piperidinyl-Y-tetrahydropyranyl, —X-pyrrolidinyl-Y-tetrahydropyranyl, —X-piperidinyl-Y-dihydrobenzofuranyl, —X-pyrrolidinyl-Y-morpholinyl, —X-piperidinyl-Y-morpholinyl, —X-piperidinyl-Y-thiomorpholinyl, —X-piperidinyl-Y-dihydroisoindole, —X-piperidinyl-Y-piperazinyl, —X-piperidinyl-Y-pyrrolidinyl, —X-piperidinyl-Y-piperidinyl or —X-piperidinyl-Y-dihydrobenzothiopyranyl) optionally substituted by one or two =O or $R^4$ groups;
- —X-heterocyclyl-Y—$C_{3-8}$ cycloalkyl (eg. —X-piperidinyl-Y-cyclohexyl, —X-piperidinyl-Y-cyclopropyl, —X-piperidinyl-Y-cyclobutyl or —X-piperidinyl-Y-cyclopentyl); or
- —X-heterocyclyl-Y-heteroaryl (eg. —X-piperidinyl-Y-isoquinolinyl, —X-piperidinyl-Y-quinolinyl, —X-piperidinyl-Y-isoxazolyl, —X-piperidinyl-Y-benzothiazolyl, —X-piperidinyl-Y-thiophenyl, —X-piperidinyl-Y-furanyl, —X-piperidinyl-Y-pyrazinyl, —X-piperidinyl-Y-pyridyl) optionally substituted by one or two $C_{1-6}$ alkyl (eg. methyl), =O, cyano or —$CONR^5R^6$ groups.

Preferably, X represents a bond or —$CH_2$—, most preferably X represents a bond.

Preferably, Y represents a bond, CO, $SO_2$ or —CO—CH=CH— most preferably Y represents a bond or CO, especially a bond.

Preferably, $R^4$ represents hydrogen, $C_{1-6}$ alkyl (eg. methyl, ethyl or t-butyl), —$C_{1-6}$ alkyl-$C_{3-8}$ cycloalkyl (eg. —$CH_2$cyclopropyl), aryl (eg. phenyl optionally substituted by a halogen atom (eg. fluorine), heterocyclyl (eg. morpholinyl) or heteroaryl (eg. pyridinyl or pyrazinyl) optionally substituted by a halogen (eg. fluorine) or $C_{1-6}$ alkoxy (eg. methoxy) group.

Preferably, $R^5$ and $R^6$ independently represent hydrogen, $C_{1-6}$ alkyl (eg. methyl, ethyl, isopropyl or propyl), —$C_{3-8}$ cycloalkyl (eg. cyclobutyl or cyclopentyl), —$C_{1-6}$ alkyl-$C_{3-8}$ cycloalkyl (eg. —$CH_2$-cyclopropyl), heterocyclyl (eg. pyrrolidinyl, piperidinyl, morpholinyl or tetrahydropyranyl) or aryl (eg. phenyl) optionally substituted by a halogen (eg. fluorine), cyano or $C_{1-6}$ alkoxy (eg. methoxy) group or —$NR^5R^6$ represents a nitrogen containing heterocyclyl group (eg. azetidinyl, morpholinyl, pyrrolidinyl or piperidinyl) optionally substituted by one or two =O groups.

More preferably, $R^5$ and $R^6$ independently represent hydrogen, $C_{1-6}$ alkyl (eg. methyl or ethyl), —$C_{3-8}$ cycloalkyl (eg. cyclobutyl or cyclopentyl) or —$C_{1-6}$ alkyl-$C_{3-8}$ cycloalkyl (eg. —$CH_2$-cyclopropyl).

Particularly preferably, $R^2$ represents
hydrogen;
- $C_{1-6}$ alkyl (eg. methyl or propyl) optionally substituted by a —$CO_2R^4$ (eg. —$CO_2Et$ or —$CO_2H$) or —$CONR^5R^6$ (eg. —CO N(Me)$_2$, —CO N(H)(Me), —CON(H)(cyclopentyl), —CO N(H)(phenyl), —CO-pyrrolidinyl, —CO-piperidinyl or —CO-morpholinyl) group;
- —X—$C_{3-8}$ cycloalkyl-Y-heterocyclyl (eg. -cyclohexyl-CO-morpholinyl);
- —X-aryl (eg. -phenyl or —$CH_2$-phenyl) optionally substituted by one or two halogen (eg. fluorine, iodine or chlorine), $C_{1-6}$ alkyl (eg. methyl), $C_{1-6}$ alkoxy (eg. methoxy), —$CO_2R^4$ (eg. —$CO_2H$ or —$CO_2Me$), —$CONR^5R^6$ (eg. —CON(H)(Me), —CON(Et)$_2$ (optionally substituted by a methoxy group), —CON(Me)(Pr) substituted by a cyano group) or —CON(H)(—$CH_2$-cyclopropyl), —$NR^5COR^6$ (eg. —NHCOMe), —$SO_2NR^5R^6$ (eg. —$SO_2N(Et)_2$) or cyano groups;
- —X-aryl-Y-heterocyclyl (eg. -phenyl-pyrrolidinyl, -phenyl-CO-pyrrolidinyl, -phenyl-CO-morpholinyl, -phenyl-$SO_2$-morpholinyl, —$CH_2$-phenyl-CO-pyrrolidinyl, —$CH_2$-phenyl-CO-morpholinyl or —$CH_2$-phenyl-CO-piperazinyl) optionally substituted by one or two =O, halogen (eg. fluorine) or $R^4$ (eg. phenyl (optionally substituted by a fluorine atom) or pyridyl) groups;
- —X-heteroaryl (eg. -pyridinyl, —$CH_2$-pyridinyl, -pyrazinyl, -pyrimidinyl, -pyridazinyl, -quinolinyl, —$CH_2$-quinolinyl, -pyrrolopyridinyl, -furopyridinyl, -naphthyridinyl, -thiazolyl or -thienyl) optionally substituted by one or two halogen (eg. bromine or iodine), $C_{1-6}$ alkyl (eg. methyl), $C_{1-6}$ alkoxy (eg. methoxy or ethoxy), cyano, nitro, —$OR^4$ (eg. hydroxy), —$CO_2R^4$ (eg. $CO_2H$ or $CO_2Me$), —$COR^4$ (eg. COMe), —$NR^5R^6$ (eg. —$NH_2$ or —N(H)(Me)), —$NR^5COR^6$ (eg. NHCOMe, NHCO-i-Pr, —NHCO-pyrrolidinyl, —NHCO-piperidinyl, —NHCO-morpholinyl or —NHCO-tetrahydropyranyl), —$CONR^5R^6$ (eg. —$CONH_2$, —$CON(Me)_2$, —CON(Me)(Et), —CON(H)(Me), —CON(H)(i-Pr), —CON(Et)$_2$ (optionally substituted by a methoxy group), —CON(H)(Et) (optionally substituted by a methoxy group), —CON(H)(—$CH_2$cyclopropyl), —CON(H)(cyclobutyl), —CON(H)(cyclopentyl), —CON(H)(cyclopropyl) or —CON(H)(tetrahydropyranyl)) or =O groups;
- —X-heteroaryl-Y-aryl (eg. -pyrazinyl-phenyl) optionally substituted by a $C_{1-6}$ alkylsulfonyl (eg. —$SO_2Me$) or —$NR^5COR^6$ (eg. —NHCOMe) group;
- —X-heteroaryl-Y-heteroaryl (eg. -pyridinyl-pyrazolyl, -pyridinyl-oxadiazolyl, -pyridinyl-oxazolyl or -pyridinyl-pyrazinyl) optionally substituted by a $C_{1-6}$ alkyl (eg. methyl) group;
- —X-heteroaryl-Y-heterocyclyl (eg. -pyridinyl-CO-morpholinyl, -pyridinyl-CO-pyrrolidinyl, -pyridinyl-CO-piperidinyl, -pyridinyl-CO-thiomorpholinyl, -pyridinyl-imidazolidinyl, -pyridinyl-CO-tetrahydro-oxazepinyl, -pyridinyl-CO-azetidinyl, -pyridinyl-oxazolidinyl, -pyridinyl-isothiazolidinyl, -pyrazinyl-morpholinyl, -pyrazinyl-CO-morpholinyl, -pyrazinyl-CO-piperidinyl, -pyrazinyl-CO-pyrrolidinyl, -pyrazinyl-thiomorpholinyl, -pyrazinyl-oxazolidinyl, -pyrazinyl-CO-azetidinyl, -pyrazinyl-piperidinyl, -pyrazinyl-pyrrolidinyl, -pyridinyl-pyrrolidinyl, -pyridinyl-piperidinyl, -pyridinyl-$SO_2$-morpholinyl or -pyridazinyl-CO-morpholinyl) optionally substituted by one or two =O, $C_{1-6}$ alkyl (eg. methyl), —$OR^4$ (eg. hydroxy) or halogen (eg. chlorine or bromine) groups;
- —X-heterocyclyl (eg. -piperidinyl, —$CH_2$-piperidinyl, -pyrrolidinyl or —$CH_2$-pyrrolidinyl) optionally substituted by a $C_{1-6}$ alkylsulfonyl (eg. —$SO_2Me$), $C_{1-6}$ alkoxycarbonyl (eg. —CO—$CH_2CH_2OMe$), —$CO_2R^4$ (eg. —$CO_2$-t-Bu)—$COR^4$ (eg. —$COCH_2$cyclopropyl)

or —COR⁵R⁶ (eg. —CON(i-Pr)₂, —CON(Et)₂, —CON(i-Pr)(Et) (substituted by a methoxy group), —CON(H)(i-Pr) or —CON(H)(4-fluorophenyl) group;

—X-heterocyclyl-Y-aryl (eg. -piperidinyl-CO-phenyl, -pyrrolidinyl-CO-phenyl, -piperidinyl-CO-phenyl, -piperidinyl-CO—CH═CH-phenyl, -piperidinyl-SO₂-phenyl, pyrrolidinyl-SO₂-phenyl, —CH₂-piperidinyl-CO-phenyl, —CH₂-pyrrolidinyl-CO-phenyl, —CH₂-piperidinyl-SO₂-phenyl or —CH₂-pyrrolidinyl-SO₂-phenyl) optionally substituted by a halogen (eg. fluorine), cyano, $C_{1-6}$ alkylsulfonyl (eg —SO₂Me), R⁴ (eg. phenyl or morpholinyl) or —CONR⁵R⁶ (eg. —CO-pyrrolidinyl substituted by an ═O group) group;

—X-heterocyclyl-Y-heterocyclyl (eg. -piperidinyl-CO-tetrahydropyranyl, —CH₂-piperidinyl-CO-tetrahydropyranyl, -pyrrolidinyl-CO-tetrahydropyranyl, —CH₂-pyrrolidinyl-CO-tetrahydropyranyl, -piperidinyl-CO-dihydrobenzofuranyl, -pyrrolidinyl-CO-morpholinyl, —CH₂-pyrrolidinyl-CO-morpholinyl, -piperidinyl-CO-morpholinyl, —CH₂-piperidinyl-CO-morpholinyl, -piperidinyl-CO-thiomorpholinyl, -piperidinyl-CO-dihydroisoindole, -piperidinyl-CO-piperazinyl, -piperidinyl-CO-pyrrolidinyl, -piperidinyl-CO-piperidinyl or -piperidinyl-CO-dihydrobenzothiopyranyl) optionally substituted by one or two ═O or R⁴ (eg. pyrazinyl) groups;

—X-heterocyclyl-Y-$C_{3-8}$ cycloalkyl (eg. -piperidinyl-CO-cyclohexyl, -piperidinyl-CO-cyclopropyl, -piperidinyl-CO-cyclobutyl or -piperidinyl-CO-cyclopentyl); or —X-heterocyclyl-Y-heteroaryl (eg. -piperidinyl-CO-isoquinolinyl, -piperidinyl-CO-quinolinyl, -piperidinyl-CO-isoxazolyl, -piperidinyl-SO₂-isoxazolyl, -piperidinyl-CO-benzothiazolyl, -piperidinyl-CO-thiophenyl, -piperidinyl-CO-furanyl, -piperidinyl-CO-pyrazinyl, -piperidinyl-pyrazinyl, -piperidinyl-CO-pyridinyl or -piperidinyl-pyridinyl) optionally substituted by one or two $C_{1-6}$ alkyl (eg. methyl), ═O, cyano or —CONR⁵R⁶ (eg. —CON(H)(Me), —CON(H)(—CH₂cyclopropyl), —CO-azetidinyl or —CO-morpholinyl) groups.

More preferably, R² represents

—X-aryl (eg. phenyl) optionally substituted by a CONR⁵R⁶ group;

—X-aryl-Y-heterocyclyl (eg. —X-phenyl-Y-morpholinyl or —X-phenyl-Y-pyrrolidinyl);

—X-heteroaryl (eg. pyrazinyl or pyridinyl) optionally substituted by a CONR⁵R⁶ group;

—X-heteroaryl-Y-heterocyclyl (eg. —X-pyridinyl-Y-morpholinyl, —X-pyridinyl-Y-pyrrolidinyl, —X-pyridinyl-Y-piperidinyl, —X-pyridinyl-Y-thiomorpholinyl, —X-pyrazinyl-Y-morpholinyl, —X-pyrazinyl-Y-piperidinyl or —X-pyrazinyl-Y-pyrrolidinyl) optionally substituted by one or two ═O groups; or —X-heterocyclyl-Y-heterocyclyl (eg. —X-piperidinyl-Y-tetrahydropyranyl, —X-piperidinyl-Y-morpholinyl or —X-pyrrolidinyl-Y-morpholinyl).

Yet more preferably, R² represents

—X-aryl (eg. -phenyl or —CH₂-phenyl) optionally substituted by one or two halogen (eg. fluorine, iodine or chlorine), $C_{1-6}$ alkyl (eg. methyl), $C_{1-6}$ alkoxy (eg. methoxy), —CO₂R⁴ (eg. —CO₂H or —CO₂Me), —CONR⁵R⁶ (eg. —CON(H)(Me), —CON(Et)₂ (optionally substituted by a methoxy group), —CON(Me)(Et) substituted by a cyano group) or —CON(H)(—CH₂-cyclopropyl), —NR⁵COR⁶ (eg. —NHCOMe), —SO₂NR⁵R⁶ (eg. —SO₂N(Et)₂) or cyano groups;

—X-aryl-Y-heterocyclyl (eg. -phenyl-pyrrolidinyl, -phenyl-CO-pyrrolidinyl, -phenyl-CO-morpholinyl, -phenyl-SO₂-morpholinyl, —CH₂-phenyl-CO-pyrrolidinyl, —CH₂-phenyl-CO-morpholinyl or —CH₂-phenyl-CO-piperazinyl) optionally substituted by one or two ═O, halogen (eg. fluorine) or R⁴ (eg. phenyl (optionally substituted by a fluorine atom) or pyridyl) groups;

—X-heteroaryl (eg. -pyridinyl, —CH₂-pyridinyl, -pyrazinyl, -pyrimidinyl, -pyridazinyl, -quinolinyl, —CH₂-quinolinyl, -pyrrolopyridinyl, -furopyridinyl, -naphthyridinyl, -thiazolyl or -thienyl) optionally substituted by one or two halogen (eg. bromine or iodine), $C_{1-6}$ alkyl (eg. methyl), $C_{1-6}$ alkoxy (eg. methoxy or ethoxy), cyano, nitro, —OR⁴ (eg. hydroxy), —CO₂R⁴ (eg. CO₂H or CO₂Me), —COR⁴ (eg. COMe), —NR⁵R⁶ (eg. —NH₂ or —N(H)(Me)), —NR⁵COR⁶ (eg. NHCOMe, NHCO-i-Pr, —NHCO-pyrrolidinyl, —NHCO-piperidinyl, —NHCO-morpholinyl or —NHCO-tetrahydropyranyl), —CONR⁵R⁶ (eg. —CONH₂, —CON(Me)₂, —CON(Me)(Et), —CON(H)(Me), —CON(H)(i-Pr), —CON(Et)₂ (optionally substituted by a methoxy group), —CON(H)(Et) (optionally substituted by a methoxy group), —CON(H)(—CH₂cyclopropyl), —CON(H)(cyclobutyl), —CON(H)(cyclopentyl), —CON(H)(cyclopropyl) or —CON(H)(tetrahydropyranyl)) or ═O groups;

—X-heteroaryl-Y-heterocyclyl (eg. -pyridinyl-CO-morpholinyl, -pyridinyl-CO-pyrrolidinyl, -pyridinyl-CO-piperidinyl, -pyridinyl-CO-thiomorpholinyl, -pyridinyl-imidazolidinyl, -pyridinyl-CO-tetrahydro-oxazepinyl, -pyridinyl-CO-azetidinyl, -pyridinyl-oxazolidinyl, -pyridinyl-isothiazolidinyl, -pyrazinyl-morpholinyl, -pyrazinyl-CO-morpholinyl, -pyrazinyl-CO-piperidinyl, -pyrazinyl-CO-pyrrolidinyl, -pyrazinyl-thiomorpholinyl, -pyrazinyl-oxazolidinyl, -pyrazinyl-CO-azetidinyl, -pyrazinyl-piperidinyl, -pyrazinyl-pyrrolidinyl, -pyridinyl-pyrrolidinyl, -pyridinyl-piperidinyl, -pyridinyl-SO₂-morpholinyl or -pyridazinyl-CO-morpholinyl) optionally substituted by one or two ═O, $C_{1-6}$ alkyl (eg. methyl), —OR⁴ (eg. hydroxy) or halogen (eg. chlorine or bromine) groups; or —X-heterocyclyl-Y-heterocyclyl (eg. -piperidinyl-CO-tetrahydropyranyl, —CH₂-piperidinyl-CO-tetrahydropyranyl, -pyrrolidinyl-CO-tetrahydropyranyl, —CH₂-pyrrolidinyl-CO-tetrahydropyranyl, -piperidinyl-CO-dihydrobenzofuranyl, -pyrrolidinyl-CO-morpholinyl, —CH₂-pyrrolidinyl-CO-morpholinyl, -piperidinyl-CO-morpholinyl, —CH₂-piperidinyl-CO-morpholinyl, -piperidinyl-CO-thiomorpholinyl, -piperidinyl-CO-dihydroisoindole, -piperidinyl-CO-piperazinyl, -piperidinyl-CO-pyrrolidinyl, -piperidinyl-CO-piperidinyl or -piperidinyl-CO-dihydrobenzothiopyranyl) optionally substituted by one or two ═O or R⁴ (eg. pyrazinyl) groups.

Most preferably, R² represents

—X-aryl (eg. -phenyl) optionally substituted by one or two halogen (eg. fluorine), $C_{1-6}$ alkoxy (eg. methoxy), —CONR⁵R⁶ (eg. —CON(H)(Me)), —NR⁵COR⁶ (eg. —NHCOMe) or cyano groups;

—X-aryl-Y-heterocyclyl (eg. -phenyl-pyrrolidinyl) optionally substituted by one or two ═O or halogen (eg. fluorine) groups;

unsubstituted —X-heterocyclyl-Y-heterocyclyl (eg. -piperidinyl-CO-morpholinyl);

—X-heteroaryl (eg. -2-pyridinyl or -2-pyrazinyl) optionally substituted by a —CONR⁵R⁶ (eg. CON(H)(Me)) group; or —X-heteroaryl-Y-heterocyclyl (eg. -2-pyridinyl-N-pyrrolidinyl) wherein said heterocyclyl group is optionally substituted by an =O group (eg. -2-pyridinyl-N-pyrrolidinone).

Especially preferably, $R^2$ represents —X-heteroaryl (eg. -2-pyridinyl) substituted by a —$CONR^5R^6$ group (eg. 4-methylaminocarbonylpyridin-2-yl).

Preferably, n represents 0 or 1, more preferably 0.

When n represents 1, $R^3$ is preferably a halogen (eg. iodine) atom or a cyano group.

Preferred compounds according to the invention include examples E1-E288 as shown below, or a pharmaceutically acceptable salt thereof.

More preferred compounds according to the invention include:

5-(3-Cyclobutyl-2,3,4,5-tetrahydro-1H-benzo[d]azepin-7-yloxy)-pyrazine-2-carboxylic acid methyl amide; and 1-{6-[(3-Cyclobutyl-2,3,4,5-tetrahydro-1H-3-benzazepin-7-yl)oxy]-3-pyridinyl}-2-pyrrolidinone or a pharmaceutically acceptable salt thereof.

An especially preferred compound according to the invention is 6-(3-cyclobutyl-2,3,4,5-tetrahydro-1H-benzo[d]azepin-7-yloxy)-N-methyl-nicotinamide or a pharmaceutically acceptable salt thereof.

Compounds of formula (I) may form acid addition salts with acids, such as conventional pharmaceutically acceptable acids, for example maleic, hydrochloric, hydrobromic, phosphoric, acetic, fumaric, salicylic, sulphate, citric, lactic, mandelic, tartaric and methanesulphonic. Salts, solvates and hydrates of compounds of formula (I) therefore form an aspect of the invention.

Certain compounds of formula (I) are capable of existing in stereoisomeric forms. It will be understood that the invention encompasses all geometric and optical isomers of these compounds and the mixtures thereof including racemates. Tautomers also form an aspect of the invention.

The present invention also provides a process for the preparation of a compound of formula (I) or a pharmaceutically acceptable salt thereof, which process comprises:

(a) reacting a compound of formula (II)

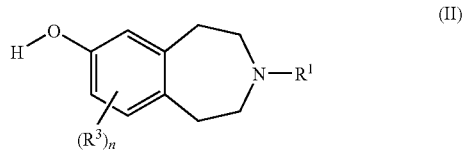

(II)

wherein $R^1$, $R^3$ and n are as defined above, with a compound of formula $R^{2'}$-$L^1$, wherein $R^{2'}$ is as defined above for $R^2$ or a group convertible thereto and $L^1$ represents a suitable leaving group such as a halogen atom (eg. bromine or iodine) or an optionally activated hydroxyl group;

(b) reacting a compound of formula (III)

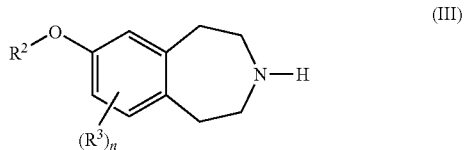

(III)

wherein $R^2$, $R^3$ and n are as defined above, with a compound of formula $R^{1'}$-$L^2$, wherein $R^{1'}$ is as defined above for $R^1$ or a group convertible thereto and $L^2$ represents a suitable leaving group such as a halogen atom (eg. bromine, iodine or tosylate); or (c) reacting a compound of formula (III) as defined above, with a ketone of formula $R^{1'}$=O, wherein $R^{1'}$ is as defined above for $R^1$ or a group convertible thereto; or (d) deprotecting a compound of formula (I) which is protected; and (e) interconversion to other compounds of formula (I).

When the leaving group $L^1$ is attached to an $sp^3$ hybridised carbon, for example, $R^{2'}$-$L^1$ is an alkyl halide, process (a) typically comprises the use of a suitable base, such as potassium carbonate in an appropriate solvent such as 2-butanone optionally in the presence of a catalyst such as potassium iodide at an appropriate temperature such as reflux.

When the leaving group $L^1$ is attached to an $sp^2$ hybridised carbon, for example, $R^{2'}$-$L^1$ is an aryl halide, process (a) typically comprises the use of a copper(I) salt, such as copper (I) iodide, in the presence of a base such as sodium hydride, in an appropriate solvent such as pyridine, at an appropriate temperature such as reflux.

When the leaving group $L^1$ is attached to an activated $sp^2$ hybridised carbon for example, $R^{2'}$-$L^1$ is a heteroaryl halide such as a 2-chloropyridine or 2-chloropyrazine, process (a) typically comprises the use of a suitable base, such as sodium hydride in an appropriate solvent such as dimethylformamide or dimethyl sulfoxide, at an appropriate temperature. Alternatively, potassium tert-butoxide in tert-butanol at an appropriate temperature may also be employed.

When the leaving group $L^1$ is attached to an activated $sp^2$ hybridised carbon, for example $R^{2'}$-$L^1$ is an aryl halide such as 3,4-difluoro-benzonitrile, process (a) typically comprises the use of a suitable base, potassium carbonate, in a suitable solvent, such as dimethyl sulfoxide, at a suitable temperature.

When $L^1$ is a hydroxyl group attached to an $sp^3$ hybridised carbon, for example, $R^{2'}$-$L^1$ is an alcohol, process (a) typically comprises the use of a phosphine such as triphenylphosphine in a suitable solvent such as tetrahydrofuran, followed by addition of an azodicarboxylate such as diethylazodicarboxylate at a suitable temperature such as room temperature.

Process (b) typically comprises the use of a suitable base, such as potassium carbonate in an appropriate solvent such as 2-butanone optionally in the presence of a catalyst such as potassium iodide at an appropriate temperature such as reflux.

Process (c) typically comprises the use of reductive conditions (such as treatment with a borohydride eg. sodium triacetoxyborohydride), optionally in the presence of an acid, such as acetic acid, in an appropriate solvent such as dichloromethane at a suitable temperature such as room temperature.

In process (d), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxan or trifluoroacetic acid in dichloromethane) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—$COCF_3$) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid.

Process (e) may be performed using conventional interconversion procedures such as epimerisation, oxidation, reduction, alkylation, nucleophilic or electrophilic aromatic substitution, ester hydrolysis, amide bond formation or transition metal mediated coupling reactions. Examples of transition metal mediated coupling reactions useful as interconversion procedures include the following: Palladium catalysed coupling reactions between organic electrophiles, such as aryl halides, and organometallic reagents, for example boronic acids (Suzuki cross-coupling reactions); Palladium catalysed amination and amidation reactions between organic electrophiles, such as aryl halides, and nucleophiles, such as amines and amides; Copper catalysed amidation reactions between organic electrophiles (such as aryl halides) and nucleophiles such as amides; and Copper mediated coupling reactions between phenols and boronic acids.

Compounds of formula (II) and (III) may be prepared in accordance with the following scheme

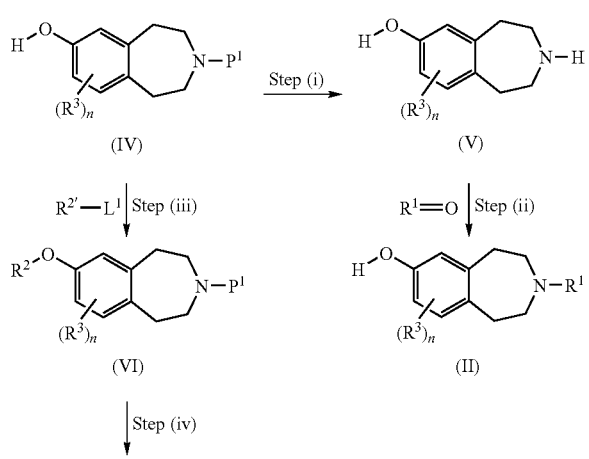

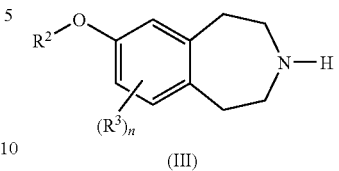

wherein $R^1$, $R^2$, $R^{2'}$, $R^3$, n and $L^1$ are as defined above and $P^1$ represents a suitable protecting group such as Boc.

Step (i) typically comprises a deprotection reaction, for example, when $P^1$ represents Boc the deprotection reaction comprises reaction of a compound of formula (IV) with an acid, for example hydrochloric acid in dioxan or trifluoroacetic acid in dichloromethane.

Step (ii) may be performed under reducing conditions in an analogous manner to that described for process (c).

Step (iii) may be performed in an analogous manner to that described for process (a).

Step (iv) typically comprises a deprotection reaction to provide a compound of formula (III) and can be performed as described in step (i).

Compounds of formula (VI) wherein $R^2$ represents —X-aryl, —X-heteroaryl, —X-aryl-Y—$C_{3-8}$ cycloalkyl, —X-aryl-Y-aryl, —X-aryl-Y-heteroaryl, —X-aryl-Y-heterocyclyl, —X-heteroaryl-Y—$C_{3-8}$ cycloalkyl, —X-heteroaryl-Y-aryl, —X-heteroaryl-Y-heteroaryl or —X-heteroaryl-Y-heterocyclyl and X represents a bond may also be prepared in accordance with the following scheme

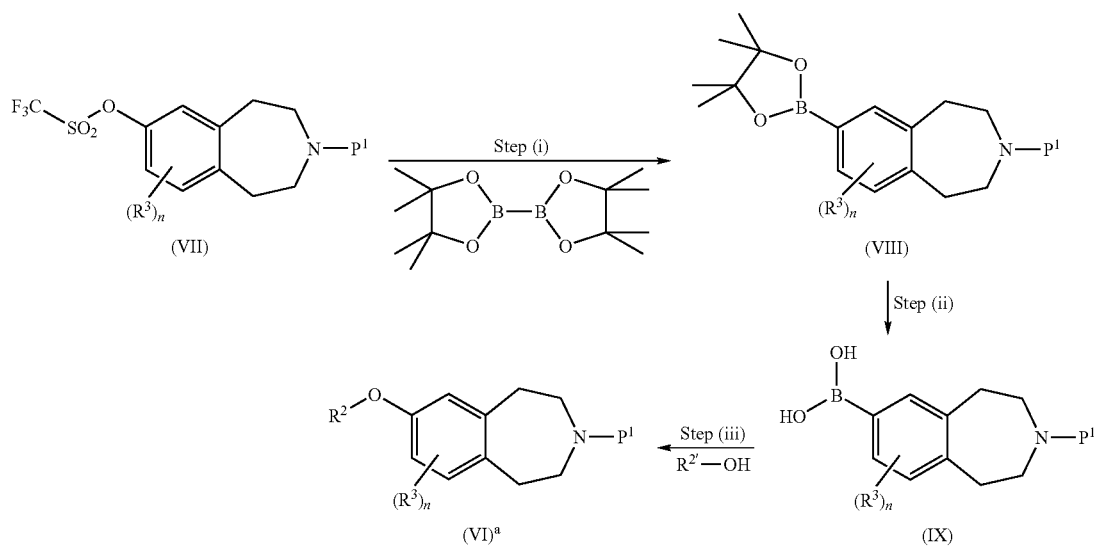

wherein $R^2$, $R^{2'}$, $R^3$ and n are as defined above and $P^1$ represents a suitable protecting group such as Boc.

Step (i) may be performed under palladium catalysed cross-coupling conditions, for example using bis(diphenylphosphino)ferrocenedichloropalladium (II) complex and 1,1'-bis(diphenylphosphino)ferrocene as the catalyst system, in combination with a suitable base, such as potassium acetate, in a suitable solvent, for example dioxane, at a suitable temperature, for example reflux.

Step (ii) may be performed under oxidising conditions, for example using sodium periodate in the presence of ammonium acetate, in a suitable solvent system, such as acetone and water, at a suitable temperature, for example room temperature.

Step (iii) may be performed in the presence of a copper salt, for example copper acetate, in combination with a suitable base, such as triethylamine, together with molecular sieves, in a suitable solvent, for example dichloromethane, at a suitable temperature, for example room temperature.

Compounds of formula (IV) may be prepared in an analogous manner to those described in Description 3 of WO 02/40471.

Compounds of formula (VII) may be prepared as outlined in Bioorg. Med. Chem. Lett.; 10; 22; 2000; 2553-2556.

Compounds of formula (I) and their pharmaceutically acceptable salts have affinity for and are antagonists and/or inverse agonists of the histamine H3 receptor and are believed to be of potential use in the treatment of neurological diseases including Alzheimer's disease, dementia, age-related memory dysfunction, mild cognitive impairment, cognitive deficit, epilepsy, neuropathic pain, inflammatory pain, migraine, Parkinson's disease, multiple sclerosis, stroke and sleep disorders including narcolepsy; psychiatric disorders including schizophrenia (particularly cognitive deficit of schizophrenia), attention deficit hypereactivity disorder, depression and addiction; and other diseases including obesity, asthma, allergic rhinitis, nasal congestion, chronic obstructive pulmonary disease and gastrointestinal disorders.

Thus the invention also provides a compound of formula (I) or a pharmaceutically acceptable salt thereof, for use as a therapeutic substance in the treatment or prophylaxis of the above disorders, in particular cognitive impairments in diseases such as Alzheimer's disease and related neurodegenerative disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt thereof and a pharmaceutically acceptable carrier.

The present invention further provides a pharmaceutical composition which comprises the compound of formula (I) or a pharmaceutically acceptable salt thereof and a pharmaceutically acceptable carrier.

Compounds of formula (I) may be used in combination with other therapeutic agents, for example histamine H1 antagonists or medicaments claimed to be useful as either disease modifying or symptomatic treatments of Alzheimer's disease. Suitable examples of such other therapeutic agents may be agents known to modify cholinergic transmission such as 5-$HT_6$ antagonists, M1 muscarinic agonists, M2 muscarinic antagonists or acetylcholinesterase inhibitors. When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable derivative thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable derivative thereof is used in combination with a second therapeutic agent active against the same disease state the dose of each compound may differ from that when the compound is used alone. Appropriate doses will be readily appreciated by those skilled in the art.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

The following Descriptions and Examples illustrate the preparation of compounds of the invention.

Description 1

7-Benzyloxy-1,2,4,5-tetrahydro-benzo[d]azepine-3-carboxylic acid tert-butyl ester (D1)

7-Hydroxy-1,2,4,5-tetrahydro-benzo[d]azepine-3-carboxylic acid tert-butyl ester (PCT Int. Appl. (2002), WO 02/40471) (790 mg, 3 mmol), potassium carbonate (1.24 g, 9 mmol) and catalytic potassium iodide were suspended in 2-butanone (20 ml). Benzyl bromide (536 μL, 4.5 mmol) was added and the mixture heated at reflux for 24 hours. The solids were filtered and then washed with acetone. The filtrate was concentrated in vacuo and the crude oil purified by column chromatography, eluting with a mixture of ethyl acetate and hexane (1:4) to afford the title compound (D1) (1.06 g, 100%), $^1$H NMR (CDCl$_3$) 7.44 (5H, m), 7.03 (1H, d, J=8.1 Hz), 6.77 (1H, s), 6.74 (1H, dd, J 8.1 & 2.4 Hz), 3.49 (4H, m), 2.84 (4H, m), 1.48 (9H, s).

Description 2

7-Benzyloxy-1,2,4,5-tetrahydro-benzo[d]azepine (D2)

7-Benzyloxy-1,2,4,5-tetrahydro-benzo[d]azepine-3-carboxylic acid tert-butyl ester (D1) (1.06 g, 3 mmol) was dissolved in dichloromethane (15 ml) and treated with trifluoroacetic acid (15 ml). The solution was stirred at room temperature for 2 hours, concentrated in vacuo and then twice co-evaporating with dichloromethane. The residue was dissolved in methanol and applied to a SCX ion exchange column (Varian bond-elute, 10 g) and washed with methanol and then a mixture of 0.880 ammonia/methanol. The combined basic fractions were reduced in vacuo and the residue purified by column chromatography, eluting with a mixture of 0.880 ammonia:ethanol:dichloromethane (1:9:90) to afford the title compound (D2) (702 mg, 93%), MS (ES+) m/e 254 [M+H]$^+$.

Description 3

7-(4-Methoxycarbonyl-benzyloxy)-1,2,4,5-tetrahydro-benzo[d]azepine-3-carboxylic acid tert-butyl ester (D3)

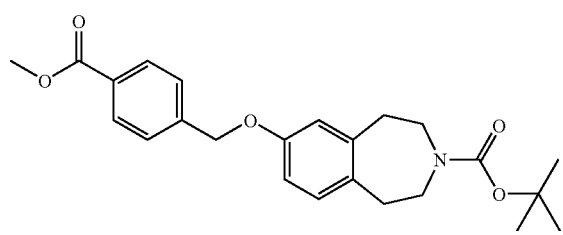

7-Hydroxy-1,2,4,5-tetrahydro-benzo[d]azepine-3-carboxylic acid tert-butyl ester (WO 02/40471) (5.27 g, 20.0 mmol), potassium carbonate (8.30 g, 60.0 mmol) and catalytic potassium iodide were suspended in butanone (100 ml). Methyl 4-(bromomethyl)benzoate (5.5 g, 24.0 mmol) dissolved in butanone (50 ml) was added dropwise after which the reaction mixture was stirred at reflux for 24 hours. The reaction mixture was cooled, the solids were filtered and then washed with acetone. The filtrate was concentrated in vacuo and the crude mixture was purified by column chromatography eluting with a mixture of ethyl acetate:hexane (1:4) to afford the title compound (D3). MS (ES+) m/e 344 [(M+H)—CO$_2{}^t$Bu]$^+$.

Description 4

4-(2,3,4,5-Tetrahydro-1H-benzo[d]azepin-7-yloxymethyl)-benzoic acid methyl ester (D4)

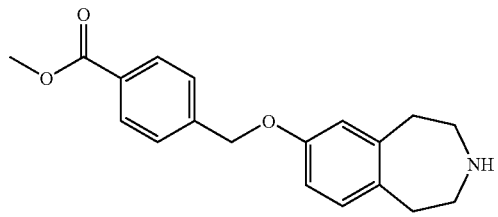

7-(4-Methoxycarbonyl-benzyloxy)-1,2,4,5-tetrahydro-benzo[d]azepine-3-carboxylic acid tert-butyl ester (D3) (6.35 g) was dissolved in dichloromethane (30 ml) and treated with trifluoroacetic acid (30 ml). The solution was stirred at room temperature for 2 hours, concentrated in vacuo and then twice co-evaporated with dichloromethane. The residue was dissolved in dichloromethane and washed with 10% aqueous sodium hydroxide, water and brine. The organic layer was dried over magnesium sulfate, filtered and concentrated in vacuo to afford the title compound (D4).

Description 5

1-(6-Chloro-pyridin-3-yl)-1-morpholin-4-yl-methanone (D5)

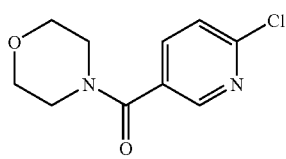

Morpholine (0.2 ml, 2.2 mmol) was added to stirred solution of 6-chloronicotinoyl chloride (250 mg, 1.4 mmol) in dichloromethane (10 ml). After 2 hours the reaction was allowed to cool and the crude mixture was applied to a SCX ion exchange cartridge (Varian bond-elute, 10 g) and washed with methanol. The methanolic fractions were concentrated in vacuo to afford the title compound (D5).

Descriptions 6-31

Descriptions 6-31 (D6-D31) were prepared and used without further characterisation using the method described for Description 5 (D5) from the appropriate aryl halide and amine indicated in the table:

| Description | Aryl Halide | Amine |
| --- | --- | --- |
| 1-(6-Chloro-pyridin-3-yl)-1-pyrrolidin-1-yl-methanone (D6) | 6-Chloronicotinoyl chloride | Pyrrolidine |
| 6-Chloro-nicotinamide (D7) | 6-Chloronicotinoyl chloride | Ammonia |
| 6-Chloro-N,N-dimethyl-nicotinamide (D8) | 6-Chloronicotinoyl chloride | Dimethylamine |
| 6-Chloro-N-ethyl-N-methyl-nicotinamide (D9) | 6-Chloronicotinoyl chloride | N-Ethylmethyl-amine |
| 6-Chloro-N-methyl-nicotinamide (D10) | 6-Chloronicotinoyl chloride | Methylamine |
| 6-Chloro-N-cyclopentyl-nicotinamide (D11) | 6-Chloronicotinoyl chloride | Cyclopentylamine |
| 1-(6-Chloro-pyridin-3-yl)-1-piperidin-1-yl-methanone (D12) | 6-Chloronicotinoyl chloride | Piperidine |
| 1-(2-Chloro-pyridin-4-yl)-1-piperidin-1-yl-methanone (D13) | 2-Chloro-isonicotinoyl chloride | Piperidine |
| 1-(2-Chloro-pyridin-4-yl)-1-pyrrolidin-1-yl-methanone (D14) | 2-Chloro-isonicotinoyl chloride | Pyrrolidine |
| 1-(2-Chloro-pyridin-4-yl)-1-morpholin-4-yl-methanone (D15) | 2-Chloro-isonicotinoyl chloride | Morpholine |
| 1-(6-Chloro-pyridin-2-yl)-1-piperidin-1-yl-methanone (D16) | 6-Chloro-pyridine-2-carbonyl chloride | Piperidine |
| 1-(6-Chloro-pyridin-2-yl)-1-(1,1-dioxothiomorpholin-4-yl)-methanone (D17) | 6-Chloro-pyridine-2-carbonyl chloride | Thiomorpholine 1,1-dioxide |
| 1-(6-Chloro-pyridin-2-yl)-1-pyrrolidin-1-yl-methanone (D18) | 6-Chloro-pyridine-2-carbonyl chloride | Pyrrolidine |
| 1-(6-Chloro-pyridin-2-yl)-1-morpholin-4-yl-methanone (D19) | 6-Chloro-pyridine-2-carbonyl chloride | Morpholine |
| 1-(2-Chloro-pyridin-3-yl)-1-morpholin-4-yl-methanone (D20) | 2-Chloro-nicotinoyl chloride | Morpholine |
| 1-(2-Chloro-pyridin-3-yl)-1-piperidin-1-yl-methanone (D21) | 2-Chloro-nicotinoyl chloride | Piperidine |
| 1-(4-Iodo-phenyl)-1-morpholin-4-yl-methanone (D22) | 4-Iodo-benzoyl chloride | Morpholine |
| 4-Iodo-N-cyclopropylmethyl-benzamide (D23) | 4-Iodo-benzoyl chloride | Cyclopropylmethyl-amine |
| 1-(4-Iodo-phenyl)-1-pyrrolidin-1-yl-methanone (D24) | 4-Iodo-benzoyl chloride | Pyrrolidine |
| 4-Iodo-N-cyclobutyl-benzamide (D25) | 4-Iodo-benzoyl chloride | Cyclobutylamine |
| 4-Iodo-N,N-diethyl-benzamide (D26) | 4-Iodo-benzoyl chloride | Diethylamine |
| 4-Iodo-N-(2-cyano-ethyl)-N-methyl-benzamide (D27) | 4-Iodo-benzoyl chloride | 3-Methylamino-propionitrile |
| 1-(3-Iodo-phenyl)-1-morpholin-4-yl-methanone (D28) | 3-Iodo-benzoyl chloride | Morpholine |
| 3-Iodo-N-cyclopropylmethyl-benzamide (D29) | 3-Iodo-benzoyl chloride | Cyclopropylmethyl-amine |
| 4-(4-Iodo-benzenesulfonyl)-morpholine (D30) | 4-Iodo-benzenesulfonyl chloride | Morpholine |
| 4-Iodo-N,N-diethyl-benzenesulfonamide (D31) | 4-Iodo-benzenesulfonyl chloride | Diethylamine |

Description 32

5-Bromo-2-(1-piperidinyl)pyrimidine (D32)

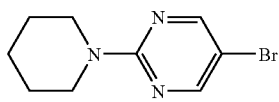

Piperidine (5.1 ml, 51.6 mmol) was added to a stirred solution of 5-bromo-2-chloropyrimidine (5 g, 25.8 mmol) and triethylamine (9.0 ml, 64.5 mmol) in toluene (30 ml). After stirring at room temperature for 24 hours the reaction mixture was diluted with ethyl acetate and washed with 2N hydrochloric acid, brine and dried (magnesium sulfate). The organic layer was filtered, concentrated in vacuo and the resulting residue was purified by column chromatography eluting with ethyl acetate to afford the title compound (D32).

Descriptions 33-35

Descriptions 33-35 (D33-D35) were prepared using an analogous method to that described for Description 32 (D32) substituting piperidine for the appropriate amine indicated in the table:

| Description | Amine |
|---|---|
| 5-Bromo-2-(1-pyrrolidinyl)pyrimidine (D33) | Pyrrolidine |
| 4-(5-Bromo-2-pyrimidinyl)thiomorpholine 1,1-dioxide (D34) | Thiomorpholine 1,1-dioxide |
| 5-Bromo-N-methyl-2-pyrimidinamine (D35) | Methylamine |

Descriptions 36-37

Descriptions 36-37 (D36-D37) were prepared using an analogous method to that described for Description 5 (D5), substituting morpholine for the appropriate amine indicated in the table:

| Description | Amine |
|---|---|
| 6-Chloro-N-(cyclopropylmethyl)-3-pyridinecarboxamide (D36) | Cyclopropylmethylamine |
| 5-(1-Azetidinylcarbonyl)-2-chloropyridine (D37) | Azetidine |

Description 38

5-Bromo-2-pyrimidinecarbonitrile (D38)

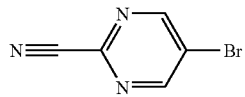

Sodium cyanide (2.30 g, 46.6 mmol) was dissolved in dimethylformamide (60 ml) and treated with 5-bromo-2-chloropyrimidine (6.0 g, 31.1 mmol). The resulting mixture was stirred at room temperature for 18 hours, diluted with water and extracted with dichloromethane. The dichloromethane extracts were combined, washed with water, dried (magnesium sulphate), filtered and concentrated in vacuo. The crude product was purified by column chromatography eluting with a mixture of ethyl acetate:hexane (1:4) to afford the title compound (D38).

Description 39

1,1-Dimethylethyl 7-({5-[(methylamino)carbonyl]-2-pyridinyl}oxy)-1,2,4,5-tetrahydro-3H-3-benzazepine-3-carboxylate (D39)

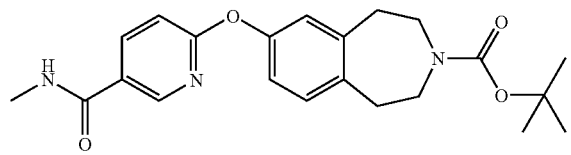

7-Hydroxy-1,2,4,5-tetrahydro-benzo[d]azepine-3-carboxylic acid tert-butyl ester (PCT Int. Appl. (2002), WO 02/40471) (8.7 g, 33 mmol) was dissolved in tert-butanol and treated with potassium-tert-butoxide (4 g, 36 mmol). After stirring for 30 minutes at room temperature, 6-chloro-N-methyl-nicotinamide (D10) (5.1 g, 30 mmol) was added and the reaction mixture was stirred at reflux for 20 hours. The reaction mixture was cooled to room temperature and concentrated in vacuo. Ice/water was added to the crude residue resulting in a precipitate which was collected by filtration. The solid precipitate was dissolved in ethyl acetate, washed with brine and dried (magnesium sulfate). The organic layer was filtered, concentrated in vacuo and the resulting residue was purified by column chromatography eluting with a mixture of ethyl acetate:hexane (1:1) to afford the title compound (D39). NMR (CDCl$_3$) 8.52 (1H, d, J= 2.4), 8.12 (1H, dd, J=8.8), 7.16 (1H, m), 6.95-6.81 (3H, m), 6.02 (1H, br), 3.57 (4H, br), 3.02 (3H, d, J=2.4), 2.89 (4H, br), 1.49 (9H, s).

Description 40

N-Methyl-6-(2,3,4,5-tetrahydro-1H-3-benzazepin-7-yloxy)-3-pyridinecarboxamide (D40)

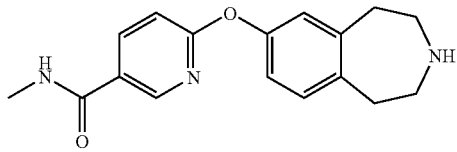

1,1-Dimethylethyl 7-({5-[(methylamino)carbonyl]-2-pyridinyl}oxy)-1,2,4,5-tetrahydro-3H-3-benzazepine-3-carboxylate (D39) (3.98 g, 10 mmol) was dissolved in dioxane (40 ml) and treated with a solution of 4M hydrogen chloride in dioxane (35 ml). The reaction mixture was allowed to stir at room temperature for 6 hours and then concentrated in vacuo to afford the title compound (D40); MS (ES+) m/e 298 [M+H]$^+$.

Description 41

1,1-Dimethylethyl 7-hydroxy-8-iodo-1,2,4,5-tetrahydro-3H-3-benzazepine-3-carboxylate (D41)

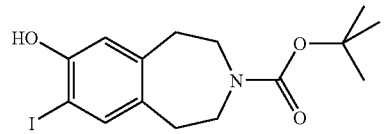

A solution of 7-hydroxy-1,2,4,5-tetrahydro-3H-benzo[d]azepine-3-carboxylic acid tert-butyl ester (PCT Int. Appl. (2002), WO 02/40471) (5.2 g, 20 mmol) in 33% methylamine in ethanol (30 ml) was stirred at 0° C. A solution of sodium iodide (4.6 g, 30 mmol) and iodine (5.2 g, 20 mmol) in water (30 ml) was added below the surface of the reaction mixture. After stirring at 0° C. for 1 hour the mixture was concentrated in vacuo. The residue was diluted with ethyl acetate and water. The organic layer was separated, washed with water and brine. The organic layer was dried over magnesium sulfate, filtered and concentrated in vacuo to afford the title compound (D41); (7.0 g, 90%), $^1$H NMR (d$_6$-DMSO) 10.0 (1H, br s), 7.41 (1H, s), 6.65 (1H, s), 3.40 (4H, m), 2.70 (4H, m), 1.40 (9H, s).

Description 42

1,1-Dimethylethyl 7-iodo-8-({5-[(methylamino)carbonyl]-2-pyridinyl}oxy)-1,2,4,5-tetrahydro-3H-3-benzazepine-3-carboxylate (D42)

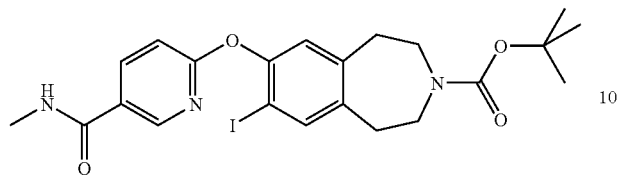

Sodium hydride (60% disp. in mineral oil, 240 mg, 6 mmol) was added to a stirred solution of 1,1-dimethylethyl 7-hydroxy-8-iodo-1,2,4,5-tetrahydro-3H-3-benzazepine-3-carboxylate (D41) (1.94 g, 5 mmol) in dimethyl sulfoxide (10 ml). After 10 minutes, 6-chloro-N-methyl-nicotinamide (D10) (850 mg, 5 mmol) was added and the reaction mixture was heated to 100° C. for 20 hours. After cooling to room temperature the reaction mixture was diluted with water and dichloromethane. The organic layer was separated, washed with water and brine, dried over magnesium sulfate, filtered and concentrated in vacuo. The residue was purified by column chromatography (1:1 ethyl acetate:hexanes) to afford the title product (D42).

Description 43

N-Methyl-6-(8-iodo-2,3,4,5-tetrahydro-1H-3-benzazepin-7-yloxy)-3-pyridinecarboxamide (D43)

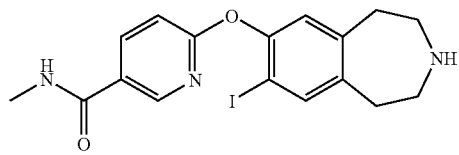

Description 43 (D43) was prepared from 1,1-dimethylethyl 7-iodo-8-({5-[(methylamino)carbonyl]-2-pyridinyl}oxy)-1,2,4,5-tetrahydro-3H-3-benzazepine-3-carboxylate (D42) using an analogous method to that described for Description 2 (D2); MS (ES+) m/e 424 [M+H]$^+$.

Description 44

1,1-Dimethylethyl 7-iodo-8-[(phenyl methyl)oxy]-1,2,4,5-tetrahydro-3H-3-benzazepine-3-carboxylate (D44)

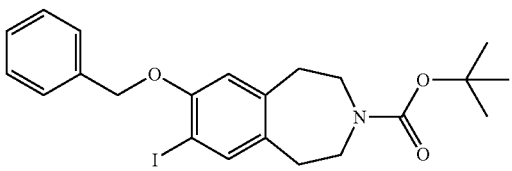

Sodium hydride (60% disp. in mineral oil, 576 mg, 14.4 mmol) was added to a stirred solution of 1,1-dimethylethyl 7-hydroxy-8-iodo-1,2,4,5-tetrahydro-3H-3-benzazepine-3-carboxylate (D41) (4.67 g, 12 mmol) in dimethylformamide (30 ml). After 15 minutes, benzyl bromide (2.04 g, 1.4 ml, 12 mmol) was added and the mixture stirred for 2 hours. The mixture was diluted with water and ethyl acetate, the organic layer was separated, washed with water and brine, dried over magnesium sulfate, filtered and concentrated in vacuo. The residue was purified by column chromatography eluting with a mixture of ethyl acetate:hexanes (1:10) to afford the title product (D44).

Description 45

7-Iodo-8-[(phenylmethyl)oxy]-2,3,4,5-tetrahydro-1H-3-benzazepine (D45)

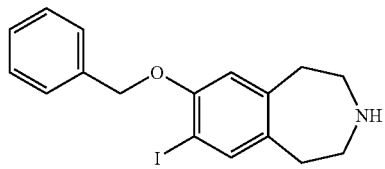

Description D45 (D45) was prepared from 1,1-dimethylethyl 7-iodo-8-[(phenylmethyl)oxy]-1,2,4,5-tetrahydro-3H-3-benzazepine-3-carboxylate (D44) using the analogous method to that described for Description 2 (D2); MS (ES+) m/e 380 [M+H]$^+$.

Description 46

1-(3-Chloro-2-pyrazinyl)-2-pyrrolidinone (D46)

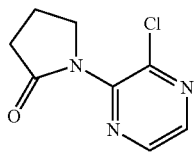

Step 1: 3-Chloropyrazine 1-oxide

A mixture of chloropyrazine (9.6 g, 83.3 mmol) and hydrogen peroxide solution (30%, 16 ml) in glacial acetic acid (26 ml) was heated at 70° C. for 18 hours. The mixture was allowed to cool to room temperature, poured into water (250 ml) and extracted with dichloromethane (3×100 ml). The dichloromethane extracts were combined, washed with saturated sodium bicarbonate solution (2×70 ml), water (3×100 ml) and brine (100 ml). The organic portion was dried under sodium sulfate and evaporated in vacuo to give a white solid which was recrystallised from absolute ethanol to give the title compound (0.45 g). $^1$H NMR (CDCl$_3$) 8.27-8.26 (1H, d), 8.15 (1H, s), 8.03-8.02 (1H, dd).

Step 2: 2,3-Dichloropyrazine

3-Chloropyrazine 1-oxide (D46, Step 1) (2.2 g, 16.9 mmol) was added slowly to phosphorus oxychloride (10 ml) at 60° C. When the addition was complete the mixture was heated at reflux for 60 minutes. The mixture was allowed to cool and poured into ice and solid sodium acetate (5 g). This was stirred until the ice had melted and then extracted with dichloromethane. The dichloromethane extracts were combined, washed with saturated sodium bicarbonate solution, water and brine. The organic portion was dried under sodium sulfate and evaporated in vacuo. The resulting residue was purified by column chromatography eluting with a mixture of ethyl acetate:hexane (1:20) to afford the title compound (0.86 g). $^1$H NMR (CDCl$_3$) 8.32 (2H, s).

Step 3: 1-(3-Chloro-2-pyrazinyl)-2-pyrrolidinone

Sodium hydride (60% in mineral oil, 67 mg, 1.62 mmol) was added to a solution of pyrrolidinone (0.12 ml, 1.54 mmol) in dry dimethylformamide (5 ml) under argon at 0° C. The mixture was allowed to warm to room temperature over 1.5 hours. A solution of 2,3-dichloropyrazine (D46, Step 2) (250 mg, 1.69 mmol) in dry dimethylformamide (2 ml) was added and the mixture stirred at room temperature under argon for 2 hours. The mixture was poured onto water (30 ml) and was extracted with ethyl acetate (×3). The ethyl acetate extracts were combined, washed with brine, dried under magnesium sulfate and evaporated in vacuo. The resulting residue was purified by column chromatography eluting with a mixture of ethyl acetate:pentane (1:1) to afford the title compound (0.10 g); MS (ES+) m/e 198 [M+H]$^+$.

Description 47

2,5-Dichloropyrazine (D47)

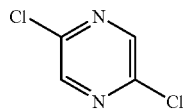

Step 1: 5-Chloro-2-pyrazinamine

Aminopyrazine (10 g, 10.5 mmol) was dissolved in dry dimethylformamide (60 ml) and was treated with N-chlorosuccinimide (15.36 g, 11.5 mmol) under argon at 0° C. The mixture was stirred for 30 minutes and then allowed to warm to room temperature. The mixture was poured onto water and extracted with diethyl ether. The diethyl ether layers were combined and evaporated in vacuo. The resulting residue was purified by column chromatography eluting with a mixture of ethyl acetate:pentane (1:9) to afford the title compound (1.40 g); $^1$H NMR (CDCl$_3$) 8.02 (1H, s), 7.76 (1H, s), 4.61 (2H, s).

Step 2: 2,5-Dichloropyrazine

5-Chloro-2-pyrazinamine (D47, Step 1) (2.41 g, 18.6 mmol) was dissolved in concentrated hydrochloric acid (24 ml), cooled in an ice-acetone bath and treated with a solution of sodium nitrite (2.63 g, 38.1 mmol) in water (18 ml) dropwise over a period of 1 hour. The mixture was cooled in an ice-water bath and left to stir for 1 hour. The mixture was allowed to warm to room temperature over 1 hour, neutralised by addition of sodium hydroxide solution (2M) and extracted with dichloromethane. The dichloromethane layers were combined, dried under magnesium sulfate and evaporated in vacuo. The resulting residue was purified by column chromatography eluting with a mixture of ethyl acetate:pentane (1:9) to afford the title compound (0.33 g); $^1$H NMR (CDCl$_3$) 8.40 (2H, s).

Description 48

2,5-Dibromopyrazine (D48)

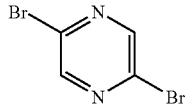

Step 1: 5-Bromo-2-pyrazinamine

Aminopyrazine (5.0 g, 52.6 mmol) was dissolved in chloroform (150 ml) and pyridine (5.11 ml, 63.2 mmol) was added. A solution of bromine (3.24 ml, 63.2 mmol) in chloroform (50 ml) was added dropwise over 1 hour. The mixture was allowed to stir for 30 minutes, diluted with water (50 ml) and allowed to stir for 10 minutes. The organic layer was separated, washed with water (50 ml), dried under magnesium sulfate and evaporated in vacuo. The resulting residue was purified by column chromatography eluting with a mixture of ethyl acetate:pentane (1:4) to afford the title compound (0.32 g); MS (ES+) m/e 175 [M+H]$^+$.

Step 2: 2,5-Dibromopyrazine

5-Bromo-2-pyrazinamine (D48, Step 1) (317 mg, 1.82 mmol) was added to a cooled (ice-acetone bath) solution of hydrobromic acid (48% aqueous) (2 ml). After stirring for 5 minutes, bromine (0.28 ml, 5.46 mmol) was added followed by a solution of sodium nitrite (314 mg, 4.55 mmol) in water dropwise over 15 minutes. The mixture was stirred for 30 minutes and allowed to warm to room temperature over 30 minutes. A solution of sodium hydroxide (2.6 g) in water (7 ml) was added and the mixture stirred for 1 hour. The mixture was extracted with dichloromethane. The dichloromethane layers were combined and evaporated in vacuo to afford the title compound (60 mg). $^1$H NMR (CDCl$_3$) 8.49 (2H, s).

Description 49

N-Methyl-5-(2,3,4,5-tetrahydro-1H-3-benzazepin-7-yloxy)-2-pyrazinecarboxamide (D49)

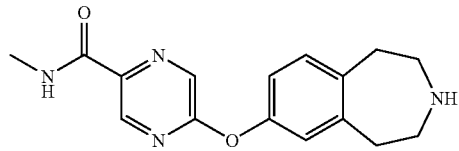

Step 1: 1,1-Dimethylethyl 7-({5-[(methyloxy)carbonyl]-2-pyrazinyl}oxy)-1,2,4,5-tetrahydro-3H-3-benzazepine-3-carboxylate Sodium hydride (60% dispersion in mineral oil) (6.4 g, 0.16 mol) was added portionwise to a solution of 7-hydroxy-1,2,4,5-tetrahydro-benzo[d]azepine-3-carboxylic acid tert-butyl ester (PCT Int. Appl. (2002), WO 02/40471) (40 g, 0.15 mol) in dry dimethylformamide (200 ml) cooled to 5° C. over 15 minutes. After 15 minutes, the mixture was allowed to warm to room temperature and stirred for 60 minutes. The mixture was cooled in an ice-water bath and methyl 5-chloro-2-pyrazinecarboxylate (31.2 g, 0.18 mol) was added portionwise. The mixture was allowed to warm to room temperature and stirred for 18 hours. The mixture was poured onto water (500 ml) and ice (500 ml) and stirred until the ice had melted. The resulting solid was collected by filtration, washed with water and dissolved in ethyl acetate (1500 ml). The ethyl acetate layer was washed with brine (200 ml), dried under sodium sulfate and evaporated in vacuo. The crude product was purified by column chromatography eluting with a mixture of ethyl acetate:hexane (1:2) to afford the title compound (35.07 g).

Step 2: 5-[(3-{[(1,1-Dimethylethyl)oxy]carbonyl}-2,3,4,5-tetrahydro-1H-3-benzazepin-7-yl)oxy]-2-pyrazinecarboxylic acid 2M Sodium hydroxide solution (110 ml) was added to a solution of 1,1-dimethylethyl 7-({5-[(methyloxy)carbonyl]-2-pyrazinyl}oxy)-1,2,4,5-tetrahydro-3H-3-benzazepine-3-carboxylate (D49, Step 1) (29.38 g, 73.6 mmol) in acetone (480 ml) and the resulting mixture was stirred at room temperature for 25 minutes. The mixture was acidified with 2M hydrochloric acid and then poured into water (2 L). The resulting white solid was collected by filtration, washed with water and dissolved in ethyl acetate (1 L). This solution was dried under sodium sulfate and evaporated in vacuo to give the title compound (27.3 g); MS (ES+) m/e 384 [M−H]+.

Step 3: 1,1-Dimethylethyl 7-({5-[(methylamino)carbonyl]-2-pyrazinyl}oxy)-1,2,4,5-tetrahydro-3H-3-benzazepine-3-carboxylate 1,1'-Carbonyldiimidazole (16.6 g, 102 mmol) was added to a solution of 5-[(3-{[(1,1-dimethylethyl)oxy]carbonyl}-2,3,4,5-tetrahydro-1H-3-benzazepin-7-yl)oxy]-2-pyrazinecarboxylic acid (D49, Step 2) (37.5 g, 97 mmol) in dry dichloromethane (400 ml) and the resulting mixture was stirred at room temperature for 18 hours. Methylamine (2M solution in tetrahydrofuran) (100 ml) was added and the mixture stirred for 2 hours. The solvent was removed in vacuo and the residue was purified by column chromatography eluting with a mixture of ethyl acetate:chloroform (1:1) to afford the title compound (25.8 g); MS (ES+) m/e 399 [M+H]+.

Step 4: N-Methyl-5-(2,3,4,5-tetrahydro-1H-3-benzazepin-7-yloxy)-2-pyrazinecarboxamide A solution of 1,1-dimethylethyl 7-({5-[(methylamino)carbonyl]-2-pyrazinyl}oxy)-1,2,4,5-tetrahydro-3H-3-benzazepine-3-carboxylate (D49, Step 3) (44.26 g, 0.11 mol) in dichloromethane (800 ml) was added dropwise to a stirring solution of 4M hydrogen chloride in dioxane (270 ml, 1.1 mol). The resulting mixture was stirred at room temperature for 60 minutes. A further quantity of 4M hydrogen chloride in dioxane (30 ml, 0.12 mol) was added and the mixture stirred for 60 minutes. The resulting white solid was collected by filtration and washed with dichloromethane. The solid was dissolved in water (2 L) and basified by addition of saturated sodium carbonate solution. The water layer was extracted with dichloromethane and the extracts filtered through celite. The celite was washed with methanol and the combined dichloromethane and methanol washings were evaporated in vacuo to give the title compound (25.1 g); MS (ES+) m/e 299 [M+H]+.

Descriptions 50-52

Descriptions 50-52 (D50-D52) were prepared and used without further characterisation using the method described for Description 5 (D5) from the appropriate aryl halide and amine indicated in the table:

Description 53

(2E)-1-{6-[(3-Cyclobutyl-2,3,4,5-tetrahydro-1H-3-benzazepin-7-yl)oxy]-3-pyridinyl}-3-(dimethylamino)-2-propen-1-one (D53)

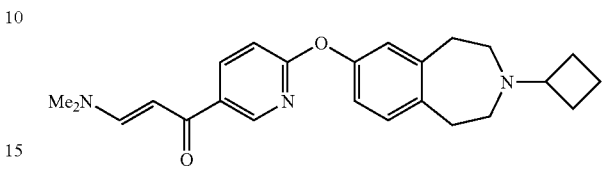

A mixture of 1-{6-[(3-cyclobutyl-2,3,4,5-tetrahydro-1H-3-benzazepin-7-yl)oxy]-3-pyridinyl}ethanone (E214) (186 mg, 0.55 mmol), dimethylformamide dimethyl acetyl (0.25 ml) and xylene (4 ml) was heated at reflux for 8 hours. The residue was diluted with toluene and concentrated in vacuo to afford the title compound (D53); MS (ES+) m/e 392 [M+H]+.

Description 54

6-[(3-Cyclobutyl-2,3,4,5-tetrahydro-1H-3-benzazepin-7-yl)oxy]-3-pyridinecarbohydrazide (D54)

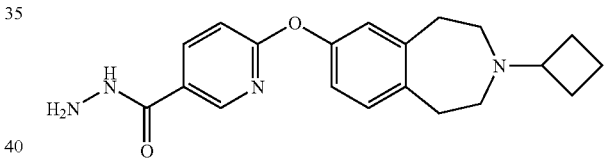

A mixture of thionyl chloride (2 ml) and 6-[(3-cyclobutyl-2,3,4,5-tetrahydro-1H-3-benzazepin-7-yl)oxy]-3-pyridinecarboxylic acid (E196b) (200 mg, 0.59 mmol) was stirred at reflux for 1 hour. The reaction mixture was concentrated in vacuo to afford a crude residue. The residue was dissolved in tetrahydrofuran (5 ml), cooled to 0° C. and hydrazine hydrate (1.5 ml) in tetrahydrofuran (1.5 ml) was added dropwise. The reaction mixture was allowed to warm to room temperature and stirred for 1 hour. The reaction mixture was then diluted with ethyl acetate and washed with a saturated solution of sodium carbonate, water, brine and dried (magnesium sulfate). The organic layer was filtered and concentrated in vacuo to afford the title compound (D54); MS (ES+) m/e 361 [M+H]+.

| Description | Aryl Halide | Amine |
|---|---|---|
| N-Ethyl-4-iodo-N-[2-(methyloxy)ethyl]benzamide (D50) | 4-Iodobenzoyl chloride | 2-Methoxyethyl ethylamine |
| 4-Iodo-N-methylbenzamide (D51) | 4-Iodobenzoyl chloride | Methylamine |
| 1-[(3-Iodophenyl)carbonyl]pyrrolidine (D52) | 3-Iodobenzoyl chloride | Pyrrolidine |

Description 55 cis-4-(4-Morpholinylcarbonyl)cyclohexanol (D55)

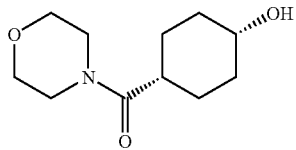

A solution of cis-4-hydroxycyclohexanecarboxylic acid (720 mg, 0.5 mmol), 1-(3-dimethylaminopropyl)-3-ethylcarbodiimide hydrochloride (1.33 g, 6 mmol) and 1-hydroxy-7-azabenzotriazole (816 mg, 6 mmol) in dichloromethane (6 ml) was treated with morpholine 1.3 ml, 15 mmol). After stirring at room temperature for 18 hours, the crude reaction was applied to a SCX ion exchange cartridge (Varian bond-elute, 5 g) and washed with methanol and then a mixture of 0.880 ammonia:methanol (1:9). The combined basic fractions were concentrated in vacuo, and the resulting residue was purified by column chromatography eluting with a mixture of 0.880 ammonia:ethanol:dichloromethane (1:9:90) to afford the title compound (D55); MS (ES+) m/e 214 [M+H]$^+$.

Description 56

2-Chloro-6-[4-(methylsulfonyl)phenyl]pyrazine (D56)

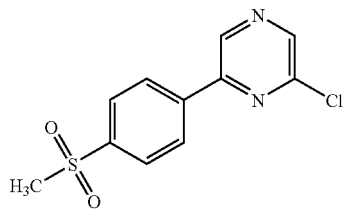

2,6-Dichloropyrazine (2.98 g, 20.0 mmol), [4-(methylsulfonyl)phenyl]boronic acid (2 g, 10.0 mmol), tetrakis(triphenylphospine)palladium (1.15 g, 1.0 mmol), potassium phosphate (10.2 g, 48 mmol) and dimethylformamide (90 ml) were heated to 80° C. for 16 hours. The solvent was removed in vacuo and the product was dissolved in chloroform and filtered through celite. The filtrate was washed with water then separated. The residue was purified by column chromatography eluting with a mixture of ethylacetate:hexane (4:6) to afford the title compound. MS (ES+) m/e 270 [M+H]$^+$.

Example 1

7-Benzyloxy-3-cyclobutyl-2,3,4,5-tetrahydro-1H-benzo[d]azepine (E1)

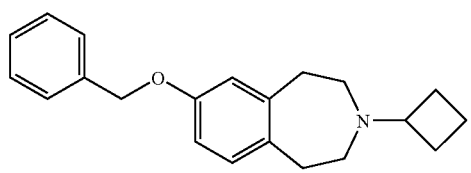

7-Benzyloxy-1,2,4,5-tetrahydro-benzo[d]azepine (D2) (25.3 g, 100 mmol) was dissolved in 2.5% acetic acid in dichloromethane (400 ml) at 0° C. and treated dropwise with cyclobutanone (11.2 ml, 150 mmol). The mixture was stirred for 30 minutes and then sodium triacetoxyborohydride (31.8 g, 150 mmol) was added portion wise. The reaction mixture was stirred at room temperature for 4 hours, basified with saturated sodium carbonate solution and extracted with dichloromethane. The combined extracts were washed with water, brine, dried over anhydrous sodium sulfate and concentrated in vacuo. The crude residue was triturated with hexane and filtered to afford the title product (E1). MS (ES+) m/e 308 [M+H]$^+$.

Example 2

7-Benzyloxy-3-cyclopentyl-2,3,4,5-tetrahydro-1H-benzo[d]azepine (E2)

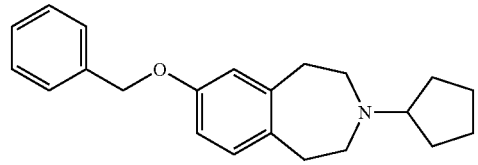

Title compound (E2) was prepared from 7-benzyloxy-1,2,4,5-tetrahydro-benzo[d]azepine (D2) and cyclopentanone using the method described for Example 1; MS (ES+) m/e 322 [M+H]$^+$.

Example 3

3-Cyclobutyl-2,3,4,5-tetrahydro-1H-benzo[d]azepin-7-ol (E3)

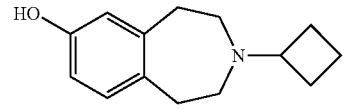

7-Benzyloxy-3-cyclobutyl-2,3,4,5-tetrahydro-1H-benzo[d]azepine (E1) (9.22 g, 30 mmol) was dissolved in ethanol (150 ml) and tetrahydrofuran (50 ml). Palladium (1.5 g, 10% on charcoal paste) was added and the reaction mixture was stirred at room temperature under hydrogen (1 atmosphere) for 5 hours. The reaction mixture was filtered through celite and the filtrate concentrated in vacuo. The crude residue was triturated with diethyl ether and filtered to afford the title product (E3); MS (ES+) m/e 218 [M+H]$^+$.

Example 4

3-Cyclopentyl-2,3,4,5-tetrahydro-1H-benzo[d]azepin-7-ol (E4)

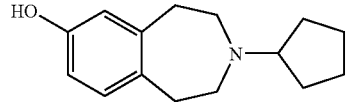

Title compound (E4) was prepared from 7-benzyloxy-3-cyclopentyl-2,3,4,5-tetrahydro-1H-benzo[d]azepine (E2) using the method described for Example 3 (E3); ¹H NMR (DMSO, d6) 9.08 (1H, brs), 6.70 (1H, d), 6.53-6.47 (2H, m), 3.31-2.50 (9H, m) 1.88-1.43 (8H, m).

Example 5a 4-(3-Cyclopentyl-2,3,4,5-tetrahydro-1H-benzo[d]azepin-7-yloxy)-piperidine-1-carboxylic acid-tert-butyl ester (E5a)

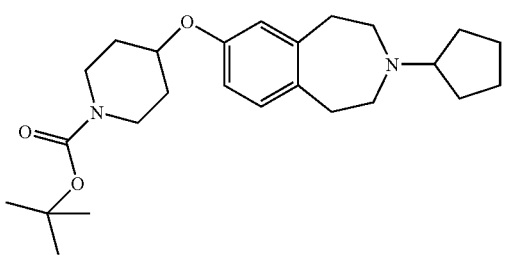

3-Cyclopentyl-2,3,4,5-tetrahydro-1H-benzo[d]azepin-7-ol (E4) (1.1 g, 4.8 mmol), 4-hydroxy-piperidine-1-carboxylic acid tert-butyl ester (1.15 g, 5.7 mmol), di-tert-butyl azodicarboxylate (1.31 g, 5.7 mmol) and triphenylphosphine (1.5 g, 5.7 mmol) were stirred at room temperature for 16 hours in tetrahydrofuran (20 ml). The mixture was acidified with acetic acid and applied to a SCX ion exchange cartridge (Varian bond-elute, 10 g) and washed with methanol and then a mixture of 0.880 ammonia:methanol (1:9). The combined basic fractions were concentrated in vacuo and the resulting residue was purified by column chromatography eluting with a mixture of 0.880 ammonia:methanol:dichloromethane (1:9:90) to afford the title product (E5a); MS (ES+) m/e 415 [M+H]⁺.

Example 5

3-Cyclopentyl-7-(piperidin-4-yloxy)-2,3,4,5-tetrahydro-1H-benzo[d]azepine (E5)

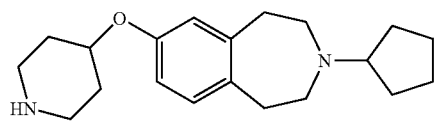

4-(3-Cyclopentyl-2,3,4,5-tetrahydro-1H-benzo[d]azepin-7-yloxy)-piperidine-1-carboxylic acid-tert-butyl ester (E5a) (593 mg, 1.43 mmol) was dissolved in dichloromethane (5 ml) and treated with trifluoroacetic acid (3 ml). The solution was stirred at room temperature for 1 hour, concentrated in vacuo and applied to a SCX ion exchange cartridge (Varian bond-elute, 5 g) and washed with methanol and then a mixture of 0.880 ammonia:methanol (1:9). The combined basic fractions were concentrated in vacuo and the resulting residue was purified by column chromatography eluting with a mixture of 0.880 ammonia:methanol:dichloromethane (1:9:90) to afford the title product (E5). MS (ES+) m/e 315 [M+H]⁺.

Examples 6-12

Examples 6-12 (E6-12) were prepared from either 3-cyclobutyl-2,3,4,5-tetrahydro-1H-benzo[d]azepin-7-ol (E3) or 3-cyclopentyl-2,3,4,5-tetrahydro-1H-benzo[d]azepin-7-ol (E4) and the appropriate alcohol indicated in the table using an analogous method to that described for Example 5a (E5a) followed by the method described for the preparation of Example 5 (E5).

| Example | Starting Material | Alcohol | LC/MS (M + H⁺) |
|---|---|---|---|
| 3-Cyclobutyl-7-(piperidin-4-yloxy)-2,3,4,5-tetrahydro-1H-benzo[d]azepine (E6) | E3 | 4-Hydroxy-piperidine-1-carboxylic acid tert-butyl ester | 301 |
| 3-Cyclobutyl-7-(piperidin-4-ylmethoxy)-2,3,4,5-tetrahydro-1H-benzo[d]azepine (E7) | E3 | 4-Hydroxymethyl-piperidine-1-carboxylic acid tert-butyl ester | 315 |
| 3-Cyclobutyl-7-((R)-1-pyrrolidin-2-ylmethoxy)-2,3,4,5-tetrahydro-1H-benzo[d]azepine (E8) | E3 | (R)-2-Hydroxymethyl-pyrrolidine-1-carboxylic acid tert-butyl ester | 301 |
| 3-Cyclobutyl-7-((R)-pyrrolidin-3-yloxy)-2,3,4,5-tetrahydro-1H-benzo[d]azepine (E9) | E3 | (R)-3-Hydroxy-pyrrolidine-1-carboxylic acid tert-butyl ester | 287 |
| 3-Cyclobutyl-7-((S)-pyrrolidin-3-yloxy)-2,3,4,5-tetrahydro-1H-benzo[d]azepine (E10) | E3 | (S)-3-Hydroxy-pyrrolidine-1-carboxylic acid tert-butyl ester | 287 |
| 3-Cyclobutyl-7-((S)-1-pyrrolidin-2-ylmethoxy)-2,3,4,5-tetrahydro-1H-benzo[d]azepine (E11) | E3 | (S)-2-Hydroxymethyl-pyrrolidine-1-carboxylic acid tert-butyl ester | 301 |
| 3-Cyclopentyl-7-(piperidin-4-ylmethoxy)-2,3,4,5-tetrahydro-1H-benzo[d]azepine (E12) | E4 | 4-Hydroxymethyl-piperidine-1-carboxylic acid tert-butyl ester | 329 |

Example 13

4-{1-[4-(3-Cyclobutyl-2,3,4,5-tetrahydro-1H-benzo[d]azepin-7-yloxy)-piperidin-1-yl]-methanoyl}-benzonitrile (E13)

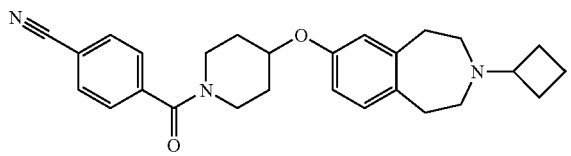

4-Cyanobenzoic acid (147 mg, 1 mmol), 1-hydroxy benzotriazole hydrate (154 mg, 1 mmol) and N-cyclohexylcarbodiimide N'-methyl polystyrene (1.8 mmol/g, 555 mg, 1 mmol) were stirred at room temperature in dichloromethane (5 ml) for 15 minutes. 3-cyclobutyl-7-(piperidin-4-yloxy)-2,3,4,5-tetrahydro-1H-benzo[d]azepine (E6) (150 mg, 0.5 mmol) was added and stirring continued for 16 hours. The reaction mixture was applied to a SCX ion exchange cartridge (Varian bond-elute, 5 g) and washed with methanol and then a mixture of 0.880 ammonia:methanol (1:9). The combined basic fractions were concentrated in vacuo and the resulting residue was purified by column chromatography eluting with dichloromethane then a mixture of 0.880 ammonia:ethanol:dichloromethate (1:9:90) to afford the title product (E13). MS (ES+) m/e 430 [M+H]$^+$.

Examples 14-42

Examples 14-42 (E14-E42) were prepared using an analogous method to that described for Example 13 (E13) from the appropriate amine and acid as indicated in the table:

| Example | Amine | Acid | LC/MS (M + H$^+$) |
|---|---|---|---|
| 1-[4-(3-Cyclobutyl-2,3,4,5-tetrahydro-1H-benzo[d]azepin-7-yloxy)-piperidin-1-yl]-1-(tetrahydro-pyran-4-yl)-methanone (E14) | 3-Cyclobutyl-7-(piperidin-4-yloxy)-2,3,4,5-tetrahydro-1H-benzo[d]azepine (E6) | Tetrahydro-pyran-4-carboxylic acid | 413 |
| 1-[4-(3-Cyclobutyl-2,3,4,5-tetrahydro-1H-benzo[d]azepin-7-yloxy)-piperidin-1-yl]-1-cyclohexyl-methanone (E15) | 3-Cyclobutyl-7-(piperidin-4-yloxy)-2,3,4,5-tetrahydro-1H-benzo[d]azepine (E6) | Cyclohexane carboxylic acid | 411 |
| 1-[4-(3-Cyclobutyl-2,3,4,5-tetrahydro-1H-benzo[d]azepin-7-yloxy)-piperidin-1-yl]-1-isoquinolin-1-yl-methanone (E16) | 3-Cyclobutyl-7-(piperidin-4-yloxy)-2,3,4,5-tetrahydro-1H-benzo[d]azepine (E6) | Isoquinoline-1-carboxylic acid | 456 |
| 4-{(E)-3-[4-(3-Cyclobutyl-2,3,4,5-tetrahydro-1H-benzo[d]azepin-7-yloxy)-piperidin-1-yl]-3-oxo-propenyl}-benzonitrile (E17) | 3-Cyclobutyl-7-(piperidin-4-yloxy)-2,3,4,5-tetrahydro-1H-benzo[d]azepine (E6) | (E)-3-(4-Cyano-phenyl)-acrylic acid | 456 |
| 1-[4-(3-Cyclobutyl-2,3,4,5-tetrahydro-1H-benzo[d]azepin-7-yloxy)-piperidin-1-yl]-1-isoquinolin-6-yl-methanone (E18) | 3-Cyclobutyl-7-(piperidin-4-yloxy)-2,3,4,5-tetrahydro-1H-benzo[d]azepine (E6) | Isoquinoline-6-carboxylic acid | 456 |
| 1-[4-(3-Cyclobutyl-2,3,4,5-tetrahydro-1H-benzo[d]azepin-7-yloxy)-piperidin-1-yl]-1-(5-methyl-isoxazol-3-yl)-methanone (E19) | 3-Cyclobutyl-7-(piperidin-4-yloxy)-2,3,4,5-tetrahydro-1H-benzo[d]azepine (E6) | 5-Methyl-isoxazole-3-carboxylic acid | 410 |
| 1-Benzothiazol-6-yl-1-[4-(3-cyclobutyl-2,3,4,5-tetrahydro-1H-benzo[d]azepin-7-yloxy)-piperidin-1-yl]-methanone (E20) | 3-Cyclobutyl-7-(piperidin-4-yloxy)-2,3,4,5-tetrahydro-1H-benzo[d]azepine (E6) | Benzothiazole-6-carboxylic acid | 462 |
| 1-[4-(3-Cyclobutyl-2,3,4,5-tetrahydro-1H-benzo[d]azepin-7-yloxy)-piperidin-1-yl]-1-pyridin-4-yl-methanone (E21) | 3-Cyclobutyl-7-(piperidin-4-yloxy)-2,3,4,5-tetrahydro-1H-benzo[d]azepine (E6) | Isonicotinic acid | 406 |
| 1-[4-(3-Cyclobutyl-2,3,4,5-tetrahydro-1H-benzo[d]azepin-7-yloxy)-piperidin-1-yl]-1-[4-(1-pyrrolidin-1-yl-methanoyl)-phenyl]-methanone (E22) | 3-Cyclobutyl-7-(piperidin-4-yloxy)-2,3,4,5-tetrahydro-1H-benzo[d]azepine (E6) | 4-(1-Pyrrolidin-1-yl-methanoyl)-benzoic acid (WO 03/04468) | 502 |
| 1-[4-(3-Cyclobutyl-2,3,4,5-tetrahydro-1H-benzo[d]azepin-7-yloxy)-piperidin-1-yl]-1-thiophen-3-yl-methanone (E23) | 3-Cyclobutyl-7-(piperidin-4-yloxy)-2,3,4,5-tetrahydro-1H-benzo[d]azepine (E6) | Thiophene-3-carboxylic acid | 411 |
| 1-[4-(3-Cyclobutyl-2,3,4,5-tetrahydro-1H-benzo[d]azepin-7- | 3-Cyclobutyl-7-(piperidin-4-yloxy)- | Furan-3-carboxylic acid | 395 |

-continued

| Example | Amine | Acid | LC/MS (M + H⁺) |
|---|---|---|---|
| yloxy)-piperidin-1-yl]-1-furan-3-yl-methanone (E24) | 2,3,4,5-tetrahydro-1H-benzo[d]azepine (E6) | | |
| 1-[4-(3-Cyclobutyl-2,3,4,5-tetrahydro-1H-benzo[d]azepin-7-yloxymethyl)-piperidin-1-yl]-1-tetrahydro-pyran-4-yl)-methanone (E25) | 3-Cyclobutyl-7-(piperidin-4-ylmethoxy)-2,3,4,5-tetrahydro-1H-benzo[d]azepine (E7) | Tetrahydro-pyran-4-carboxylic acid | 427 |
| 1-[(R)-2-(3-Cyclobutyl-2,3,4,5-tetrahydro-1H-benzo[d]azepin-7-yloxymethyl)-pyrrolidin-1-yl]-1-(tetrahydro-pyran-4-yl)-methanone (E26) | 3-Cyclobutyl-7-((R)-1-pyrrolidin-2-ylmethoxy)-2,3,4,5-tetrahydro-1H-benzo[d]azepine (E8) | Tetrahydro-pyran-4-carboxylic acid | 413 |
| 1-[(R)-3-(3-Cyclobutyl-2,3,4,5-tetrahydro-1H-benzo[d]azepin-7-yloxy)-pyrrolidin-1-yl]-1-(tetrahydro-pyran-4-yl)-methanone (E27) | 3-Cyclobutyl-7-((R)-pyrrolidin-3-yloxy)-2,3,4,5-tetrahydro-1H-benzo[d]azepine (E9) | Tetrahydro-pyran-4-carboxylic acid | 399 |
| 1-[(S)-3-(3-Cyclobutyl-2,3,4,5-tetrahydro-1H-benzo[d]azepin-7-yloxy)-pyrrolidin-1-yl]-1-(tetrahydro-pyran-4-yl)-methanone (E28) | 3-Cyclobutyl-7-((S)-pyrrolidin-3-yloxy)-2,3,4,5-tetrahydro-1H-benzo[d]azepine (E10) | Tetrahydro-pyran-4-carboxylic acid | 399 |
| 1-[(S)-2-(3-Cyclobutyl-2,3,4,5-tetrahydro-1H-benzo[d]azepin-7-yloxymethyl)-pyrrolidin-1-yl]-1-(tetrahydro-pyran-4-yl)-methanone (E29) | 3-Cyclobutyl-7-((S)-1-pyrrolidin-2-ylmethoxy)-2,3,4,5-tetrahydro-1H-benzo[d]azepine (E11) | Tetrahydro-pyran-4-carboxylic acid | 413 |
| 1-[4-(3-Cyclobutyl-2,3,4,5-tetrahydro-1H-benzo[d]azepin-7-yloxy)-piperidin-1-yl]-1-(methanesulfonyl-phenyl)-methanone (E30) | 3-Cyclobutyl-7-(piperidin-4-yloxy)-2,3,4,5-tetrahydro-1H-benzo[d]azepine (E6) | 4-Methanesulfonyl-benzoic acid | 483 |
| 1-[4-(3-Cyclobutyl-2,3,4,5-tetrahydro-1H-benzo[d]azepin-7-yloxy)-piperidin-1-yl]-1-pyrazin-2-yl-methanone (E31) | 3-Cyclobutyl-7-(piperidin-4-yloxy)-2,3,4,5-tetrahydro-1H-benzo[d]azepine (E6) | 2-Pyrazine carboxylic acid | 407 |
| 5-{1-[4-(3-Cyclobutyl-2,3,4,5-tetrahydro-1H-benzo[d]azepin-7-yloxy)-piperidin-1-yl]-methanoyl}-1H-pyridone (E32) | 3-Cyclobutyl-7-(piperidin-4-yloxy)-2,3,4,5-tetrahydro-1H-benzo[d]azepine (E6) | 6-Hydroxy nicotinic acid | 422 |
| 1-[4-(3-Cyclobutyl-2,3,4,5-tetrahydro-1H-benzo[d]azepin-7-yloxy)-piperidin-1-yl]-1-(2,3-dihydro-benzofuran-5-yl)-methanone (E33) | 3-Cyclobutyl-7-(piperidin-4-yloxy)-2,3,4,5-tetrahydro-1H-benzo[d]azepine (E6) | 2,3-Dihydro-benzofuran-5-carboxylic acid | 447 |
| 1-[4-(3-Cyclobutyl-2,3,4,5-tetrahydro-1H-benzo[d]azepin-7-yloxy)-piperidin-1-yl]-3-methoxy-propan-1-one (E34) | 3-Cyclobutyl-7-(piperidin-4-yloxy)-2,3,4,5-tetrahydro-1H-benzo[d]azepine (E6) | 3-Methoxy-propionic acid | 387 |
| 1-[4-(3-Cyclobutyl-2,3,4,5-tetrahydro-1H-benzo[d]azepin-7-yloxy)-piperidin-1-yl]-(2,3-dihydro-benzofuran-7-yl)-methanone (E35) | 3-Cyclobutyl-7-(piperidin-4-yloxy)-2,3,4,5-tetrahydro-1H-benzo[d]azepine (E6) | 2,3-Dihydro-benzofuran-7-carboxylic acid | 447 |
| 4-{1-{4-(3-Cyclopentyl-7-(piperidin-4-ylmethoxy)-2,3,4,5-tetrahydro-1H-benzo[d]azepin-7-yloxymethyl)piperidin-1-yl]-methanoyl}-benzonitrile (E36) | 3-Cyclopentyl-7-(piperidin-4-ylmethoxy)-2,3,4,5-tetrahydro-1H-benzo[d]azepine (E12) | 4-Cyano-benzoic acid | 458 |
| 1-[4-(3-Cyclopentyl-2,3,4,5-tetrahydro-1H-benzo[d]azepin-7-yloxymethyl)-piperidin-1-yl]-1-[4-(1-pyrrolidin-1-yl-methanoyl)-phenyl]-methanone (E37) | 3-Cyclopentyl-7-(piperidin-4-ylmethoxy)-2,3,4,5-tetrahydro-1H-benzo[d]azepine (E12) | 4-(1-Pyrrolidin-1-yl-methanoyl)-benzoic acid (WO 03/04468A1) | 530 |
| 4-{1-[4-(3-Cyclopentyl-2,3,4,5-tetrahydro-1H-benzo[d]azepin-7-yloxy)-piperidin-1-yl]-methanoyl}-benzonitrile (E38) | 3-Cyclopentyl-7-(piperidin-4-yloxy)-2,3,4,5-tetrahydro-1H-benzo[d]azepine (E5) | 4-Cyano-benzoic acid | 444 |

| Example | Amine | Acid | LC/MS (M + H+) |
|---|---|---|---|
| 1-[4-(3-Cyclopentyl-2,3,4,5-tetrahydro-1H-benzo[d]azepin-7-yloxy)-piperidin-1-yl]-1-pyridin-4-yl-methanone (E39) | 3-Cyclopentyl-7-(piperidin-4-yloxy)-2,3,4,5-tetrahydro-1H-benzo[d]azepine (E5) | Isonicotinic acid | 420 |
| 1-[4-(3-Cyclopentyl-2,3,4,5-tetrahydro-1H-benzo[d]azepin-7-yloxy)-piperidin-1-yl]-1-quinolin-6-yl-methanone (E40) | 3-Cyclopentyl-7-(piperidin-4-yloxy)-2,3,4,5-tetrahydro-1H-benzo[d]azepine (E5) | Quinoline-6-carboxylic acid | 470 |
| 1-[4-(3-Cyclopentyl-2,3,4,5-tetrahydro-1H-benzo[d]azepin-7-yloxy)-piperidin-1-yl]-1-[4-(1-pyrrolidin-1-yl-methanoyl)-phenyl]methanone (E41) | 3-Cyclopentyl-7-(piperidin-4-yloxy)-2,3,4,5-tetrahydro-1H-benzo[d]azepine (E5) | 4-(1-Pyrrolidin-1-yl-methanoyl)-benzoic acid (WO 03/04468A1) | 516 |
| 1-Biphenyl-4-yl-1-[4-(3-cyclopentyl-2,3,4,5-tetrahydro-1H-benzo[d]azepin-7-yloxy)-piperidin-1-yl]-methanone (E42) | 3-Cyclopentyl-7-(piperidin-4-yloxy)-2,3,4,5-tetrahydro-1H-benzo[d]azepine (E5) | 4-Biphenyl carboxylic acid | 495 |

Example 43

1-[4-(3-Cyclobutyl-2,3,4,5-tetrahydro-1H-benzo[d]azepin-7-yloxy)-piperidin-1-yl]-1-cyclopentyl-methanone (E43)

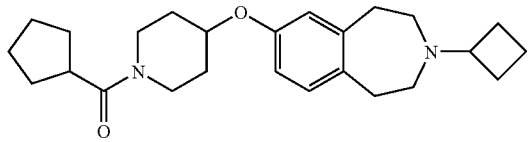

3-Cyclobutyl-7-(piperidin-4-yloxy)-2,3,4,5-tetrahydro-1H-benzo[d]azepine (E6) (150 mg, 0.5 mmol) was stirred in dichloromethane (5 ml) with diethylaminomethyl polystyrene (3.2 mmol/g, 625 mg, 2 mmol). Cyclopentane carbonyl chloride (80 μl, 0.6 mmol) was added and the mixture stirred at room temperature for 16 hours. The resin was filtered, washed with dichloromethane and the filtrate concentrated in vacuo. The residue was purified by column chromatography eluting with dichloromethane then a mixture of 0.880 ammonia:ethanol:dichloromethane (1:9:90) to afford the title product (E43); MS (ES+) m/e 397 [M+H]+.

Examples 44-51

Examples 44-51 (E44-E51) were prepared using an analogous method to that described for Example 43 (E43) from the appropriate amine and carbonyl chloride as indicated in the table:

| Example | Amine | Carbonyl chloride | LC/MS (M + H+) |
|---|---|---|---|
| 4-{1-[4-(3-Cyclobutyl-2,3,4,5-tetrahydro-1H-benzo[d]azepin-7-yloxymethyl)-piperidin-1-yl]-methanoyl}-benzonitrile (E44) | 3-Cyclobutyl-7-(piperidin-4-ylmethoxy)-2,3,4,5-tetrahydro-1H-benzo[d]azepine (E7) | 4-Cyano benzoyl chloride | 444 |
| 4-{1-[(R)-2-(3-Cyclobutyl-2,3,4,5-tetrahydro-1H-benzo[d]azepin-7-yloxymethyl)-pyrrolidin-1-yl]-methanoyl}-benzonitrile (E45) | 3-Cyclobutyl-7-((R)-1-pyrrolidin-2-ylmethoxy)-2,3,4,5-tetrahydro-1H-benzo[d]azepine (E8) | 4-Cyano benzoyl chloride | 430 |
| 4-{1-[(R)-3-(3-Cyclobutyl-2,3,4,5-tetrahydro-1H-benzo[d]azepin-7-yloxy)-pyrrolidin-1-yl]-methanoyl}-benzonitrile (E46) | 3-Cyclobutyl-7-((R)-pyrrolidin-3-yloxy)-2,3,4,5-tetrahydro-1H-benzo[d]azepine (E9) | 4-Cyano-benzoyl chloride | 416 |
| 4-{1-[(S)-3-(3-Cyclobutyl-2,3,4,5-tetrahydro-1H-benzo[d]azepin-7-yloxy)-pyrrolidin-1-yl]-methanoyl}-benzonitrile (E47) | 3-Cyclobutyl-7-((S)-pyrrolidin-3-yloxy)-2,3,4,5-tetrahydro-1H-benzo[d]azepine (E10) | 4-Cyano-benzoyl chloride | 416 |
| 4-{1-[(S)-2-(3-Cyclobutyl-2,3,4,5-tetrahydro-1H-benzo[d]azepin-7-yloxy)-pyrrolidin-1-yl]-methanoyl}-benzonitrile (E48) | 3-Cyclobutyl-7-((S)-1-pyrrolidin-2-ylmethoxy)-2,3,4,5-tetrahydro-1H-benzo[d]azepine (E11) | 4-Cyano-benzoyl chloride | 430 |

| Example | Amine | Carbonyl chloride | LC/MS (M + H⁺) |
|---|---|---|---|
| 1-[4-(3-Cyclobutyl-2,3,4,5-tetrahydro-1H-benzo[d]azepin-7-yloxy)-piperidin-1-yl]-2,2-dimethyl-propan-1-one (E49) | 3-Cyclobutyl-7-(piperidin-4-yloxy)-2,3,4,5-tetrahydro-1H-benzo[d]azepine (E6) | 2,2-Dimethyl-propionyl chloride | 385 |
| 1-[4-(3-Cyclobutyl-2,3,4,5-tetrahydro-1H-benzo[d]azepin-7-yloxy)-piperidin-1-yl]-1-cyclopropyl-methanone (E50) | 3-Cyclobutyl-7-(piperidin-4-yloxy)-2,3,4,5-tetrahydro-1H-benzo[d]azepine (E6) | Cyclopropane carbonyl chloride | 369 |
| 1-Cyclobutyl-1-[4-(3-cyclobutyl-2,3,4,5-tetrahydro-1H-benzo[d]azepin-7-yloxy)-piperidine-1-yl]-methanone (E51) | 3-Cyclobutyl-7-(piperidin-4-yloxy)-2,3,4,5-tetrahydro-1H-benzo[d]azepine (E6) | Cyclobutane carbonyl chloride | 383 |

Example 52

4-{1-{4-(3-Cyclobutyl-2,3,4,5-tetrahydro-1H-benzo[d]azepin-7-yloxy)-piperidin-1-yl]-1-morpholin-4-yl-methanone (E52)

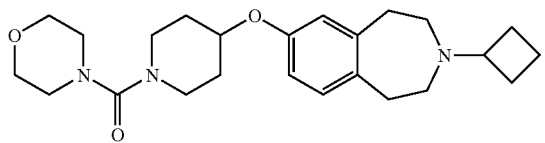

3-Cyclobutyl-7-(piperidin-4-yloxy)-2,3,4,5-tetrahydro-1H-benzo[d]azepine (E6) (150 mg, 0.5 mmol) was stirred in dichloromethane (5 ml) with diethylaminomethyl polystyrene (3.2 mmol/g, 625 mg, 2 mmol). Morpholine carbamoyl chloride (70 µL, 0.6 mmol) was added and the mixture stirred at room temperature for 16 hours. The resin was filtered, washed with dichloromethane and the filtrate concentrated in vacuo. The residue was purified by column chromatography eluting with dichloromethane then a mixture of 0.880 ammonia:ethanol:dichloromethane (1:9:90) to afford the title product (E52). MS (ES+) m/e 414 [M+H]⁺.

Examples 53-60

Examples 53-60 (E53-E60) were prepared using an analogous method to that described for Example 52 (E52) from the appropriate amine and carbonyl chloride indicated in the table:

| Example | Amine | Carbonyl Chloride | LC/MS (M + H⁺) |
|---|---|---|---|
| 1-[4-(3-Cyclobutyl-2,3,4,5-tetrahydro-1H-benzo[d]azepin-7-yloxymethyl)-piperidin-1-yl]-1-morpholin-4-yl-methanone (E53) | 3-Cyclobutyl-7-(piperidin-4-ylmethoxy)-2,3,4,5-tetrahydro-1H-benzo[d]azepine (E7) | Morpholine-4-carbonyl chloride | 428 |
| 1-[(R)-2-(3-Cyclobutyl-2,3,4,5-tetrahydro-1H-benzo[d]azepin-7-yloxymethyl)-pyrrolidin-1-yl]-1-morpholin-4-yl-methanone (E54) | 3-Cyclobutyl-7-((R)-1-pyrrolidin-2-ylmethoxy)-2,3,4,5-tetrahydro-1H-benzo[d]azepine (E8) | Morpholine-4-carbonyl chloride | 414 |
| 1-[(R)-3-(3-Cyclobutyl-2,3,4,5-tetrahydro-1H-benzo[d]azepin-7-yloxy)-pyrrolidin-1-yl]-1-morpholin-4-yl-methanone (E55) | 3-Cyclobutyl-7-((R)-pyrrolidin-3-yloxy)-2,3,4,5-tetrahydro-1H-benzo[d]azepine (E9) | Morpholine-4-carbonyl chloride | 400 |
| 1-[(S)-3-(3-Cyclobutyl-2,3,4,5-tetrahydro-1H-benzo[d]azepin-7-yloxy)-pyrrolidin-1-yl]-1-morpholin-4-yl-methanone (E56) | 3-Cyclobutyl-7-((S)-pyrrolidin-3-yloxy)-2,3,4,5-tetrahydro-1H-benzo[d]azepine (E10) | Morpholine-4-carbonyl chloride | 400 |
| 4-(3-Cyclobutyl-2,3,4,5-tetrahydro-1H-benzo[d]azepin-7-yloxy)-piperidine-1-carboxylic acid diisopropylamide (E57) | 3-Cyclobutyl-7-(piperidin-4-yloxy)-2,3,4,5-tetrahydro-1H-benzo[d]azepine (E6) | Diisopropyl-carbonyl chloride | 428 |
| 1-[4-(3-Cyclobutyl-2,3,4,5-tetrahydro-1H-benzo[d]azepin-7-yloxy)-piperidin-1-yl]-pyrrolidin-1-yl-methanone (E58) | 3-Cyclobutyl-7-(piperidin-4-yloxy)-2,3,4,5-tetrahydro-1H-benzo[d]azepine (E6) | Pyrrolidine-1-carbonyl chloride | 398 |
| 1-[4-(3-Cyclobutyl-2,3,4,5-tetrahydro-1H-benzo[d]azepin-7-yloxy)-piperidin-1-yl]-1-piperidin-1-yl-methanone (E59) | 3-Cyclobutyl-7-(piperidin-4-yloxy)-2,3,4,5-tetrahydro-1H-benzo[d]azepine (E6) | Piperidine-1-carbonyl chloride | 412 |
| 1-[(S)-2-(3-Cyclobutyl-2,3,4,5-tetrahydro-1H-benzo[d]azepin-7- | 3-Cyclobutyl-7-((S)-1-pyrrolidin-2-ylmethoxy)- | Morpholine-4-carbonyl | 414 |

| Example | Amine | Carbonyl Chloride | LC/MS (M + H$^+$) |
|---|---|---|---|
| yloxymethyl)-pyrrolidin-1-yl]-1-morpholin-4-yl-methanone (E60) | 2,3,4,5-tetrahydro-1H-benzo[d]azepine (E11) | chloride | |

Example 61

4-(3-Cyclobutyl-2,3,4,5-tetrahydro-1H-benzo[d]azepin-7-yloxy)-piperidine-1-carboxylic acid diethylamide (E61)

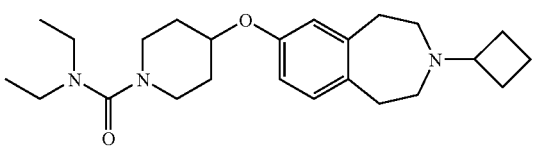

3-Cyclobutyl-7-(piperidin-4-yloxy)-2,3,4,5-tetrahydro-1H-benzo[d]azepine (E6) (1.5 g, 5 mmol) dissolved in toluene (40 ml) was added slowly to a 20% phosgene in toluene solution (12.5 ml, 25 mmol) at 0° C. The mixture was stirred at room temperature for 3 hours and concentrated in vacuo to afford a crude residue (1.91 g). The crude product (300 mg, 0.75 mmol) was then added to a stirred slurry of diethylamine (207 µL, 2 mmol) and diethylaminomethyl polystyrene (3.2 mmol/g, 1.41 g, 4.5 mmol) in dichloromethane (10 ml). The reaction mixture was stirred at room temperature for 16 hours, filtered and concentrated in vacuo. The crude residue was purified by column chromatography eluting with dichloromethane then a mixture of 0.880 ammonia:ethanol:dichloromethane (1:9:90) to afford the title product (E61). MS (ES+) m/e 400 [M+H]$^+$.

Examples 62-65

Examples 62-65 (E62-E65) were prepared using an analogous method to that described for Example 61 (E61) from 3-cyclobutyl-7-(piperidin-4-yloxy)-2,3,4,5-tetrahydro-1H-benzo[d]azepine (E6) and the appropriate amine indicated in the table:

| Example | Amine | LC/MS (M + H$^+$) |
|---|---|---|
| 1-[4-(3-Cyclobutyl-2,3,4,5-tetrahydro-1H-benzo[d]azepin-7-yloxy)-piperidin-1-yl]-1-(1,3-dihydro-isoindol-2-yl)-methanone (E62) | 2,3-Dihydro-1H-isoindole | 446 |
| 1-[4-(3-Cyclobutyl-2,3,4,5-tetrahydro-1H-benzo[d]azepin-7-yloxy)-piperidin-1-yl]-1-(2,3,5,6-tetrahydro-[1,2']bipyrazinyl-4-yl)-methanone (E63) | 3,4,5,6-Tetrahydro-2H-[1,2']bipyrazinyl | 491 |
| 1-[4-(3-Cyclobutyl-2,3,4,5-tetrahydro-1H-benzo[d]azepin-7-yloxy)-piperidine-1-carboxylic acid isopropyl-(2-methoxy-ethyl)-amide (E64) | Isopropyl-(2-methoxy-ethyl-amine | 444 |
| 1-[4-(3-Cyclobutyl-2,3,4,5-tetrahydro-1H-benzo[d]azepin-7-yloxy)-piperidin-1-yl]-(1,1-dioxo-thiomorpholin-4-yl)-methanone (E65) | Thiomorpholine 1,1-dioxide | 462 |

Example 66

4-(3-Cyclobutyl-2,3,4,5-tetrahydro-1H-benzo[d]azepin-7-yloxy)-piperidine-1-carboxylic acid isopropylamide (E66)

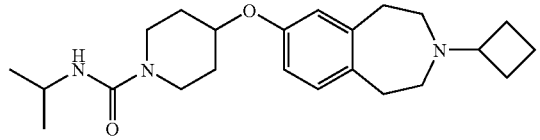

A solution of 3-cyclobutyl-7-(piperidin-4-yloxy)-2,3,4,5-tetrahydro-1H-benzo[d]azepine (E6) (150 mg, 0.5 mmol) and isopropyl isocyanate (60 µL, 0.6 mmol) in dichloromethane (5 ml) was stirred at room temperature for 16 hours. The solution was concentrated in vacuo and the residue was purified by column chromatography eluting with dichloromethane then a mixture of 0.880 ammonia:ethanol:dichloromethane (1:9:90) to afford the title product (E66). MS (ES+) m/e 386 [M+H]$^+$.

Example 67

4-(3-Cyclobutyl-2,3,4,5-tetrahydro-1H-benzo[d]azepin-7-yloxy)-piperidine-1-carboxylic acid (4-fluoro-phenyl)-amide (E67)

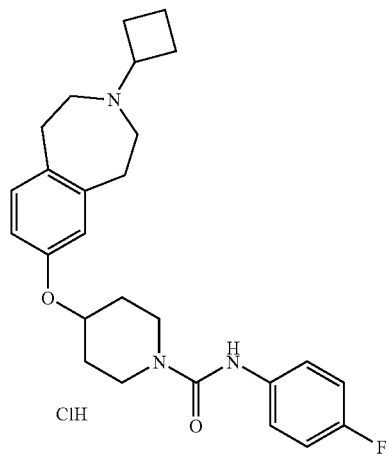

Example 67 was prepared from 3-cyclobutyl-7-(piperidin-4-yloxy)-2,3,4,5-tetrahydro-1H-benzo[d]azepine (E6) and 4-fluorophenyl-isocyanate using the method described for Example 66 (E66); MS (ES+) m/e 438 [M+H]$^+$.

Example 68

2-(3-Cyclobutyl-2,3,4,5-tetrahydro-1H-benzo[d]azepin-7-yloxy)-N,N-dimethyl-acetamide (E68)

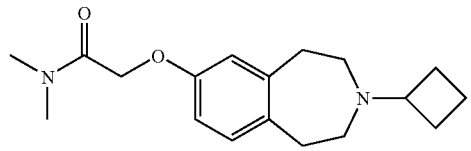

Sodium hydride (60% disp. in mineral oil, 60 mg, 1.5 mmol) was added to a stirred solution of 3-cyclobutyl-2,3,4,5-tetrahydro-1H-benzo[d]azepin-7-ol (E3) (200 mg, 0.9 mmol) in dimethyl sulfoxide (10 ml). After 0.5 hours, 2-chloro-N,N-dimethyl acetamide (0.3 ml, 2.4 mmol) was added and the reaction mixture was heated to 120° C. for 6 hours. The reaction was allowed to cool, the crude mixture was applied to a SCX cartridge ion exchange (Varian bond-elute, 10 g) and washed with methanol and then a mixture of 0.880 ammonia:methanol (1:9). The combined basic fractions were reduced in vacuo to afford the title compound (E68). MS (ES+) m/e 303 [M+H]$^+$.

Examples 69-71

Examples 69-71 (E69-E71) were prepared using the method described for Example 68 (E68) from 3-cyclobutyl-2,3,4,5-tetrahydro-1H-benzo[d]azepin-7-ol (E3) and the appropriate chloride indicated in the table.

| Example | Chloride | LC/MS (M + H$^+$) |
|---|---|---|
| 2-(3-Cyclobutyl-2,3,4,5-tetrahydro-1H-benzo[d]azepin-7-yloxy)-N-phenyl-acetamide (E69) | 2-Chloro-N-phenyl-acetamide | 351 |
| 2-(3-Cyclobutyl-2,3,4,5-tetrahydro-1H-benzo[d]azepin-7-yloxy)-1-pyrrolidin-1-yl-ethanone (E70) | 2-Chloro-1-pyrrolidin-1-yl-ethanone | 329 |
| 2-(3-Cyclobutyl-2,3,4,5-tetrahydro-1H-benzo[d]azepin-7-yloxy)-1-morpholin-4-yl-ethanone (E71) | 2-Chloro-1-morpholinyl-4-yl-ethanone | 345 |

Example 72

3-Cyclobutyl-7-(1-methanesulfonyl-piperidin-4-yloxy)-2,3,4,5-tetrahydro-1H-benzo[d]azepine (E72)

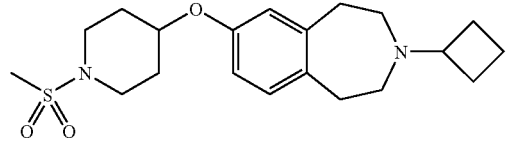

3-Cyclobutyl-7-(piperidin-4-yloxy)-2,3,4,5-tetrahydro-1H-benzo[d]azepine (E6) (150 mg, 0.5 mmol) was stirred in dichloromethane (5 ml) with diethylaminomethyl polystyrene (3.2 mmol/g, 625 mg, 2 mmol). Methane sulfonyl chloride (43 μL, 0.55 mmol) was added and the mixture stirred at room temperature for 16 hours. The resin was filtered, washed with dichloromethane and the filtrate concentrated in vacuo. The residue was purified by column chromatography eluting with a mixture of 0.880 ammonia:ethanol:dichloromethane (1:9:90) to afford the title product (E72); MS (ES+) m/e 379 [M+H]$^+$.

Examples 73-78

Examples 73-78 (E73-E78) were prepared using an analogous method to that described for Example 72 (E72) from the appropriate amine and sulfonyl chloride indicated in the table:

| Example | Amine | Sulfonyl Chloride | LC/MS (M + H$^+$) |
|---|---|---|---|
| 4-[4-(3-Cyclobutyl-2,3,4,5-tetrahydro-1H-benzo[d]azepin-7-yloxy)-piperidine-1-sulfonyl]-benzonitrile (E73) | 3-Cyclobutyl-7-(piperidin-4-yloxy)-2,3,4,5-tetrahydro-1H-benzo[d]azepine (E6) | 4-Cyano-benzenesulfonyl chloride | 466 |
| 3-Cyclobutyl-7-[1-(3,5-dimethyl-isoxazole-4-sulfonyl)-piperidin-4-yloxy]-2,3,4,5-tetrahydro-1H-benzo[d]azepine (E74) | 3-Cyclobutyl-7-(piperidin-4-yloxy)-2,3,4,5-tetrahydro-1H-benzo[d]azepine (E6) | 3,5-Dimethyl-isoxazole-4-sulfonyl chloride | 460 |
| 4-[4-(3-Cyclobutyl-2,3,4,5-tetrahydro-1H-benzo[d]azepin-7-yloxymethyl)-piperidine-1-sulfonyl]-benzonitrile (E75) | 3-Cyclobutyl-7-(piperidin-4-ylmethoxy)-2,3,4,5-tetrahydro-1H-benzo[d]azepine (E7) | 4-Cyano-benzenesulfonyl chloride | 480 |
| 4-[(R)-2-(3-Cyclobutyl-2,3,4,5-tetrahydro-1H-benzo[d]azepin-7-yloxymethyl)-pyrrolidine-1-sulfonyl]-benzonitrile (E76) | 3-Cyclobutyl-7-((R)-1-pyrrolidin-2-ylmethoxy)-2,3,4,5-tetrahydro-1H-benzo[d]azepine (E8) | 4-Cyano-benzenesulfonyl chloride | 466 |
| 4-[(R)-3-(3-Cyclobutyl-2,3,4,5-tetrahydro-1H-benzo[d]azepin-7-yloxy)-pyrrolidine-1-sulfonyl]-benzonitrile (E77) | 3-Cyclobutyl-7-((R)-pyrrolidin-3-yloxy)-2,3,4,5-tetrahydro-1H-benzo[d]azepine (E9) | 4-Cyano-benzenesulfonyl chloride | 452 |

-continued

| Example | Amine | Sulfonyl Chloride | LC/MS (M + H$^+$) |
|---|---|---|---|
| 4-[(S)-3-(3-Cyclobutyl-2,3,4,5-tetrahydro-1H-benzo[d]azepin-7-yloxy)-pyrrolidine-1-sulfonyl]-benzonitrile (E78) | 3-Cyclobutyl-7-((S)-pyrrolidin-3-yloxy)-2,3,4,5-tetrahydro-1H-benzo[d]azepine (E10) | 4-Cyano-benzenesulfonyl chloride | 452 |

Example 79

3-Cyclobutyl-7-(2,4-difluoro-benzyloxy)-2,3,4,5-tetrahydro-1H-benzo[d]azepine (E79)

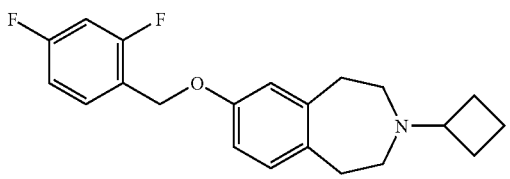

Potassium carbonate (778 mg, 5.6 mmol) was added to a stirred solution of 3-cyclobutyl-2,3,4,5-tetrahydro-1H-benzo[d]azepin-7-ol (E3) (868 mg, 4.0 mmol), 2,4-difluorobenzyl bromide (0.25 ml, 2.1 mmol) and potassium iodide (25 mg) in butanone (9 ml). The reaction mixture was stirred at reflux for 18 hours, cooled, filtered and concentrated in vacuo. The crude residue was dissolved with ethyl acetate and washed with water and brine. The organic layer was dried over magnesium sulfate, filtered and concentrated in vacuo. Purification of the resulting residue by column chromatography eluting with a mixture of 0.880 ammonia:ethanol:dichloromethane (0.25:2.25:97.5 then 1:9:10) afforded the title compound (E79); MS (ES+) m/e 344 [M+H]$^+$.

Examples 80-87

Examples 80-87 (E80-E87) were prepared from 3-cyclobutyl-2,3,4,5-tetrahydro-1H-benzo[d]azepin-7-ol (E3) and the appropriate halide indicated in the table using the general method described for Example 80 (E80):

Example 88

4-(3-Cyclopentyl-2,3,4,5-tetrahydro-1H-benzo[d]azepin-7-yloxymethyl)-benzoic acid methyl ester (E88)

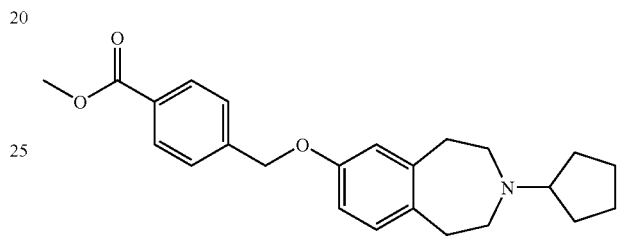

4-(2,3,4,5-Tetrahydro-1H-benzo[d]azepin-7-yloxymethyl)-benzoic acid methyl ester (D4) (2.83 g, 9.1 mmol) and cyclopentanone (1.6 ml, 18.2 mmol) were dissolved in dichloromethane (30 ml) and acetic acid (0.5 ml). Sodium triacetoxy borohydride (3.85 g, 18.2 mmol) was added and the solution was stirred at room temperature for 4 hours. The reaction mixture was washed with a saturated solution of sodium carbonate, the organic layer was dried over magnesium sulfate, filtered and concentrated in vacuo. The crude mixture was purified by column chromatography eluting with a mixture of 0.880 ammonia:ethanol:dichloromethane (1:9:90) to afford the title compound (E88); MS (ES+) m/e 380 [M+H]$^+$.

| Example | Halide | LC/MS (M + H$^+$) |
|---|---|---|
| 3-(3-Cyclobutyl-2,3,4,5-tetrahydro-1H-benzo[d]azepin-7-yloxymethyl)-benzonitrile (E80) | 3-Bromomethyl-benzonitrile | 333 |
| 3-Cyclobutyl-7-(3-methoxy-benzyloxy)-2,3,4,5-tetrahydro-1H-benzo[d]azepine (E81) | 1-Bromomethyl-3-methoxybenzene | 338 |
| 3-Cyclobutyl-7-(pyridin-2-ylmethoxy)-2,3,4,5-tetrahydro-1H-benzo[d]azepine (E82) | 2-Bromomethyl-pyridine | 309 |
| 3-Cyclobutyl-7-(pyridin-3-ylmethoxy)-2,3,4,5-tetrahydro-1H-benzo[d]azepine (E83) | 3-Bromomethyl-pyridine | 309 |
| 3-Cyclobutyl-7-(pyridin-4-ylmethoxy)-2,3,4,5-tetrahydro-1H-benzo[d]azepine (E84) | 4-Bromomethyl-pyridine | 309 |
| 2-(3-Cyclobutyl-2,3,4,5-tetrahydro-1H-benzo[d]azepin-7-yloxymethyl)-benzonitrile (E85) | 2-Bromomethyl-benzonitrile | 333 |
| 4-(3-Cyclobutyl-2,3,4,5-tetrahydro-1H-benzo[d]azepin-7-yloxymethyl)-benzonitrile (E86) | 4-Bromomethyl-benzonitrile | 333 |
| 6-(3-Cyclobutyl-2,3,4,5-tetrahydro-1H-benzo[d]azepin-7-yloxymethyl)-1-methyl-1H-quinolin-2-one (E87) | 6-Bromomethyl-1-methyl-1H-quinolin-2-one | 389 |

Example 89

4-(3-Cyclopentyl-2,3,4,5-tetrahydro-1H-benzo[d]azepin-7-yloxymethyl)-benzoic acid (E89)

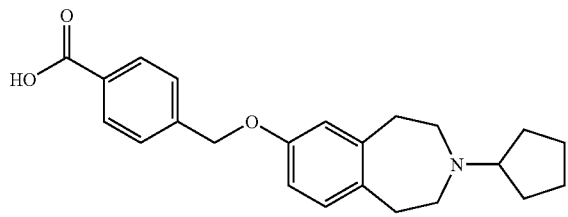

4-(3-Cyclopentyl-2,3,4,5-tetrahydro-1H-benzo[d]azepin-7-yloxymethyl)-benzoic acid methyl ester (E88) (3.1 g, 8.1 mmol)) was dissolved in a mixture of methanol (90 ml), 2N sodium hydroxide (12 ml) and water (30 ml). The resulting mixture was stirred at 60° C. for 4 hours and then cooled to room temperature. The mixture was concentrated in vacuo to remove the organic solvents and then acidified to pH 6 (2N hydrochloric acid). The resulting precipitates were filtered, washed with water and dried under vacuum to afford the title compound (E89); MS (ES+) m/e 366 [M+H]$^+$.

Example 90

1-[4-(3-Cyclopentyl-2,3,4,5-tetrahydro-1H-benzo[d]azepin-7-yloxymethyl)-phenyl]-1-pyrrolidin-yl-methanone (E90)

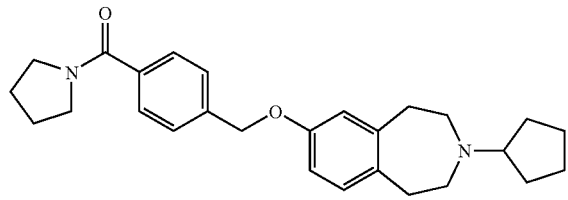

4-(3-Cyclopentyl-2,3,4,5-tetrahydro-1H-benzo[d]azepin-7-yloxymethyl)-benzoic acid (E89) (0.201 mg, 0.55 mmol)), 1,3-diisopropylcarbodiimide (44 μl, 0.6 mmol) and 1-hydroxybenzotriazole hydrate (82 mg, 0.6 mmol) were dissolved in a mixture of dichloromethane (2 ml) and dimethyl formamide (1 ml). After stirring at room temperature for 0.5 hours, pyrrolidine (41 μl, 0.5 mmol) was added and the resulting mixture was allowed to stir for 16 hours. The crude reaction was applied to a SCX ion exchange cartridge (Varian bond-elute, 5 g) and washed with methanol and then a mixture of 0.880 ammonia:methanol (1:9). The combined basic fractions were concentrated in vacuo, and the resulting residue was purified by column chromatography eluting with a mixture of 0.880 ammonia:ethanol:dichloromethane (1:9:90) to afford the title compound (E90); MS (ES+) m/e 419 [M+H]$^+$.

Examples 91-93

Examples 91-93 (E91-E93) were prepared using an analogous method to that described for Example 90 (E90) from 4-(3-cyclopentyl-2,3,4,5-tetrahydro-1H-benzo[d]azepin-7-yloxymethyl)-benzoic acid (E89) and the appropriate amine indicated in the table:

| Example | Amine | LC/MS (M + H$^+$) |
|---|---|---|
| 1-[4-(3-Cyclopentyl-2,3,4,5-tetrahydro-1H-benzo[d]azepin-7-yloxymethyl)-phenyl]-1-morpholin-4-yl-methanone (E91) | Morpholine | 435 |
| 1-[4-(3-Cyclopentyl-2,3,4,5-tetrahydro-1H-benzo[d]azepin-7-yloxymethyl)-phenyl]-1-(4-pyridin-4-yl-piperazin-1-yl)-methanone (E92) | 1-Pyridin-4-yl-piperazine | 511 |
| 1-[4-(3-Cyclopentyl-2,3,4,5-tetrahydro-1H-benzo[d]azepin-7-yloxymethyl)-phenyl]-1-[4-(4-fluoro-phenyl)-piperazin-1-yl]-methanone (E93) | 1-(4-Fluoro-phenyl)-piperazine | 528 |

Example 94

3-(3-Cyclopentyl-2,3,4,5-tetrahydro-1H-benzo[d]azepin-7-yloxymethyl)-benzoic acid methyl ester (E94)

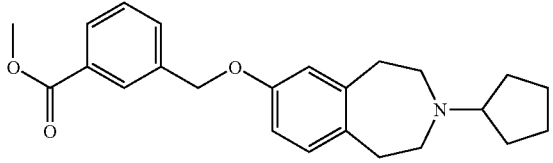

Example 94 (E94) was prepared in an analogous manner to Example 88 (E88) from 7-hydroxy-1,2,4,5-tetrahydro-benzo[d]azepine-3-carboxylic acid tert-butyl ester (WO 02/40471) and 3-bromomethyl-benzoic acid methyl ester using the methods highlighted in Description 3 (D3), Description 4 (D4) and Example 88 (E88); MS (ES+), m/e 380 [M+H]$^+$.

Example 95

3-(3-Cyclopentyl-2,3,4,5-tetrahydro-1H-benzo[d]azepin-7-yloxymethyl)-benzoic acid (E95)

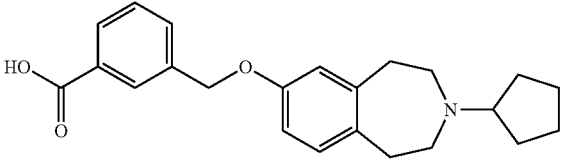

Example 95 (E95) was prepared from 3-(3-cyclopentyl-2,3,4,5-tetrahydro-1H-benzo[d]azepin-7-yloxymethyl)-benzoic acid methyl ester Example 94 (E94) using the procedure outlined for Example 89 (E89); MS (ES+), m/e 366 [M+H]$^+$.

Example 96

1-[3-(3-Cyclopentyl-2,3,4,5-tetrahydro-1H-benzo[d]azepin-7-yloxymethyl)-phenyl]-1-pyrrolidin-yl-methanone (E96)

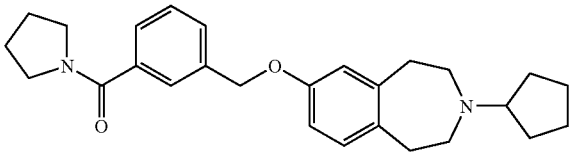

Example 96 (E96) was prepared from pyrrolidine and 3-(3-cyclopentyl-2,3,4,5-tetrahydro-1H-benzo[d]azepin-7-yloxymethyl)-benzoic acid (E95) using the procedure outlined for Example 90 (E90); MS (ES+), m/e 419 [M+H]$^+$.

Examples 97-99

Examples 97-99 (E97-E99) were prepared from 3-(3-cyclopentyl-2,3,4,5-tetrahydro-1H-benzo[d]azepin-7-yloxymethyl)-benzoic acid (E95) and the appropriate amine indicated in the table using an analogous method to that described for Example 96 (E96).

| Example | Amine | LC/MS (M + H$^+$) |
|---|---|---|
| 1-[3-(3-Cyclopentyl-2,3,4,5-tetrahydro-1H-benzo[d]azepin-7-yloxymethyl)-phenyl]-1-morpholin-4-yl-methanone (E97) | Morpholine | 435 |
| 1-[3-(3-Cyclopentyl-2,3,4,5-tetrahydro-1H-benzo[d]azepin-7-yloxymethyl)-phenyl]-1-(4-pyridin-4-yl-piperazin-1-yl)-methanone (E98) | 1-Pyridin-4-yl-piperazine | 511 |
| 1-[3-(3-Cyclopentyl-2,3,4,5-tetrahydro-1H-benzo[d]azepin-7-yloxymethyl)-phenyl]-1-[4-(4-fluoro-phenyl)-piperazin-1-yl]-methanone (E99) | 1-(4-Fluoro-phenyl)-piperazine | 528 |

Example 100

6-(3-Cyclobutyl-2,3,4,5-tetrahydro-1H-benzo[d]azepin-7-yloxy)-nicotinonitrile (E100)

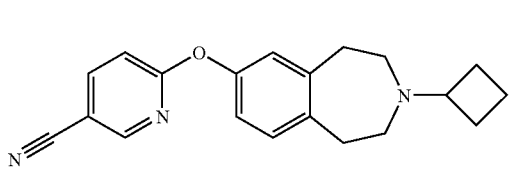

Sodium hydride (60% disp. in mineral oil, 60 mg, 1.5 mmol) was added to a stirred solution of 3-cyclobutyl-2,3,4,5-tetrahydro-1H-benzo[d]azepin-7-ol (E3) (200 mg, 0.9 mmol) in dimethyl sulfoxide (10 ml). After 0.5 hours, 6-chloronicotinylnitrile (250 mg, 1.8 mmol) was added and the reaction mixture was heated to 120° C. for 6 hours. The reaction was allowed to cool and the crude mixture was applied to a SCX ion exchange cartridge (Varian bond-elute, 10 g) and washed with methanol and then a mixture of 0.880 ammonia:methanol (1:9). The combined basic fractions were reduced in vacuo to afford the title compound (E100); MS (ES+) m/e 320 [M+H]$^+$.

Examples 101-120

Examples 101-120 (E101-E120) were prepared using an analogous method to that described for Example 100 (E100) from 3-cyclobutyl-2,3,4,5-tetrahydro-1H-benzo[d]azepin-7-ol (E3) and the appropriate aromatic chloride indicated in the table:

| Example | Chloride | LC/MS (M + H$^+$) |
|---|---|---|
| 3-Cyclobutyl-7-(pyridin-2-yloxy)-2,3,4,5-tetrahydro-1H-benzo[d]azepine (E101) | 2-Chloro-pyridine | 295 |
| 1-[6-(3-Cyclobutyl-2,3,4,5-tetrahydro-1H-benzo[d]azepin-7-yloxy)-pyridin-3-yl]-1-morpholin-4-yl-methanone (E102) | 1-(6-Chloro-pyridin-3-yl)-1-morpholin-4-yl-methanone (D5) | 408 |
| 1-[6-(3-Cyclobutyl-2,3,4,5-tetrahydro-1H-benzo[d]azepin-7-yloxy)-pyridin-3-yl]-1-pyrrolidin-1-l-methanone (E103) | 1-(6-Chloro-pyridin-3-yl)-1-pyrrolidin-1-yl-methanone (D6) | 392 |
| 6-(3-Cyclobutyl-2,3,4,5-tetrahydro-1H-benzo[d]azepin-7-yloxy)-nicotinamide (E104) | 6-Chloro-nicotinamide (D7) | 338 |
| 6-(3-Cyclobutyl-2,3,4,5-tetrahydro-1H-benzo[d]azepin-7-yloxy)-N,N-dimethyl-nicotinamide (E105) | 6-Chloro-N,N-dimethyl-nicotinamide (D8) | 366 |
| 6-(3-Cyclobutyl-2,3,4,5-tetrahydro-1H-benzo[d]azepin-7-yloxy)-N-ethyl-N-methyl-nicotinamide (E106) | 6-Chloro-N-ethyl-N-methyl-nicotinamide (D9) | 380 |
| 6-(3-Cyclobutyl-2,3,4,5-tetrahydro-1H-benzo[d]azepin-7-yloxy)-N-cyclopentyl-nicotinamide (E107) | 6-Chloro-N-cyclopentyl-nicotinamide (D11) | 406 |
| 1-[6-(3-Cyclobutyl-2,3,4,5-tetrahydro-1H-benzo[d]azepin-7-yloxy)-pyridin-3-yl]-1-piperidin-1-yl-methanone (E108) | 1-(6-Chloro-pyridin-3-yl)-1-piperidin-1-yl-methanone (D12) | 406 |
| 1-[2-(3-Cyclobutyl-2,3,4,5-tetrahydro-1H-benzo[d]azepin-7-yloxy)-pyridin-4-yl]-1-piperidin-1-yl-methanone (E109) | 1-(2-Chloro-pyridin-4-yl)-1-piperidin-1-yl-methanone (D13) | 406 |
| 1-[2-(3-Cyclobutyl-2,3,4,5-tetrahydro-1H-benzo[d]azepin-7-yloxy)-pyridin-4-yl]-1-pyrrolidin-1-yl-methanone (E110) | 1-(2-Chloro-pyridin-4-yl)-1-pyrrolidin-1-yl-methanone (D14) | 392 |
| 1-[2-(3-Cyclobutyl-2,3,4,5-tetrahydro-1H-benzo[d]azepin-7-yloxy)-pyridin-4-yl]-1-morpholin-4-yl-methanone (E111) | 1-(2-Chloro-pyridin-4-yl)-1-morpholin-4-yl-methanone (D15) | 408 |
| 1-[6-(3-Cyclobutyl-2,3,4,5-tetrahydro-1H-benzo[d]azepin-7-yloxy)-pyridin-2-yl]-1-piperidin-1-yl-methanone (E112) | 1-(6-Chloro-pyridin-2-yl)-1-piperidin-1-yl-methanone (D16) | 406 |

-continued

| Example | Chloride | LC/MS (M + H⁺) |
|---|---|---|
| 1-[6-(3-Cyclobutyl-2,3,4,5-tetrahydro-1H-benzo[d]azepin-7-yloxy)-pyridin-2-yl]-1-(1,1-dioxothiomorpholin-4-yl)-methanone (E113) | 1-(6-Chloro-pyridin-2-yl)-1-(1,1-dioxothiomorpholin-4-yl)-methanone (D17) | 466 |
| 1-[6-(3-Cyclobutyl-2,3,4,5-tetrahydro-1H-benzo[d]azepin-7-yloxy)-pyridin-2-yl]-1-pyrrolidin-1-yl-methanone (E114) | 1-(6-Chloro-pyridin-2-yl)-1-pyrrolidin-1-yl-methanone (D18) | 392 |
| 1-[6-(3-Cyclobutyl-2,3,4,5-tetrahydro-1H-benzo[d]azepin-7-yloxy)-pyridin-2-yl]-1-morpholin-4-yl-methanone (E115) | 1-(6-Chloro-pyridin-2-yl)-1-morpholin-4-yl-methanone (D19) | 408 |
| 1-[2-(3-Cyclobutyl-2,3,4,5-tetrahydro-1H-benzo[d]azepin-7-yloxy)-pyridin-3-yl]-1-morpholin-4-yl-methanone (E116) | 1-(2-Chloro-pyridin-3-yl)-1-morpholin-4-yl-methanone (D20) | 408 |
| 1-[2-(3-Cyclobutyl-2,3,4,5-tetrahydro-1H-benzo[d]azepin-7-yloxy)-pyridin-3-yl]-1-piperidin-1-yl-methanone (E117) | 1-(2-Chloro-pyridin-3-yl)-1-piperidin-1-yl-methanone (D21) | 406 |
| 3-Cyclobutyl-7-(pyrazin-2-yloxy)-2,3,4,5-tetrahydro-1H-benzo[d]azepine (E118) | 2-Chloro-pyrazine | 296 |
| 3-Cyclobutyl-7-(pyrimidin-2-yloxy)-2,3,4,5-tetrahydro-1H-benzo[d]azepine (E119) | 2-Chloro-pyrimidine | 296 |
| 7-(5-Bromo-pyrimidin-2-yloxy)-3-Cyclobutyl-2,3,4,5-tetrahydro-1H-benzo[d]azepine (E120) | 5-Bromo-2-chloro-pyrimidine | 375 |

Example 121

6-(3-Cyclobutyl-2,3,4,5-tetrahydro-1H-benzo[d]azepin-7-yloxy)-N-methyl-nicotinamide (E121)

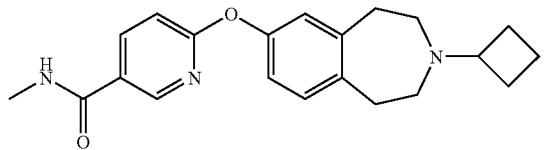

Sodium hydride (60% disp. in mineral oil, 60 mg, 1.5 mmol) was added to a stirred solution of 3-cyclobutyl-2,3,4,5-tetrahydro-1H-benzo[d]azepin-7-ol (E3) (200 mg, 0.9 mmol) in dimethyl sulfoxide (10 ml). After 0.5 hours, 6-chloro-N-methyl-nicotinamide (D10) (400 mg, 2.5 mmol) was added and the reaction mixture was heated to 120° C. for 6 hours. The reaction was allowed to cool and the crude mixture was applied to a SCX ion exchange cartridge (Varian bond-elute, 10 g) and washed with methanol and then a mixture of 0.880 ammonia:methanol (1:9). The combined basic fractions were reduced in vacuo to afford the title compound (E121). ¹H NMR (DMSO-d₆) δ 8.56 (1H, dd, J=2.4, 0.4 Hz), 8.48 (1H, br m), 8.20 (1H, dd, J=8.4, 2.4 Hz), 7.16 (1H, d, J=8.0 Hz), 7.03 (1H, dd, J=8.4, 0.4 Hz), 6.91 (1H, d, J=2.4 Hz), 6.86 (1H, dd, J=8.0, 2.4 Hz), 2.87-2.77 (8H, m), 2.36 (4H, m), 2.00 (2H, m), 1.78 (2H, m), 1.58 (2H, m); MS (ES+) m/e 352 [M+H]⁺.

Example 121

Alternative Procedure 1

6-(3-Cyclobutyl-2,3,4,5-tetrahydro-1H-benzo[d]azepin-7-yloxy)-N-methyl-nicotinamide (E121)

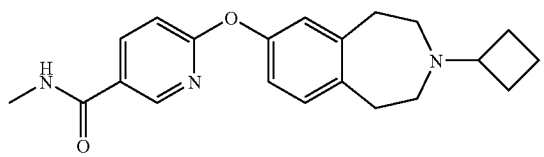

Sodium hydride (0.331 g, 8.28 mmol, 60% disp. in mineral oil) was added to a stirred solution of 3-cyclobutyl-2,3,4,5-tetrahydro-1H-benzo[d]azepin-7-ol (E3) (1.5 g, 6.9 mmol) in dimethyl sulfoxide (15 ml). After 0.5 hours, 6-chloro-N-methyl-nicotinamide (D10) (2.34 g, 13.8 mmol) was added and the reaction mixture was heated to 100° C. for 18 hours. The reaction was allowed to cool to room temperature and then partitioned between ethyl acetate and water. The ethyl acetate layer was separated and the water layer washed with further volumes of ethyl acetate. The combined organic layers were then washed with water, brine, dried (Na₂SO₄) and then filtered. The mixture was concentrated in vacuo and the resulting residue was purified by column chromatography eluting with a mixture of 0.880 ammonia:ethanol:dichloromethane (0.5:4.5:95 then 1:9:90) to afford the title compound (E121) which then was recrystallised from toluene. ¹H NMR (DMSO-d₆) δ 8.56 (1H, dd, J=2.4, 0.4 Hz), 8.48 (1H, br m), 8.20 (1H, dd, J=8.4, 2.4 Hz), 7.16 (1H, d, J=8.0 Hz), 7.03 (1H, dd, J=8.4, 0.4 Hz), 6.91 (1H, d, J=2.4 Hz), 6.86 (1H, dd, J=8.0, 2.4 Hz), 2.87-2.77 (8H, m), 2.36 (4H, m), 2.00 (2H, m), 1.78 (2H, m), 1.58 (2H, m); MS (ES+) m/e 352 [M+H]⁺.

Example 121

Alternative Procedure 2

6-(3-Cyclobutyl-2,3,4,5-tetrahydro-1H-benzo[d]azepin-7-yloxy)-N-methyl-nicotinamide (E121)

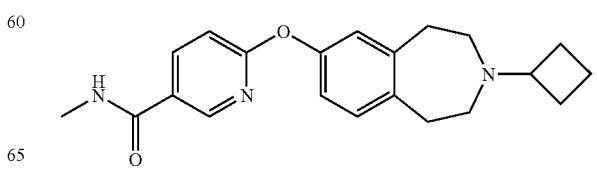

A mixture of N-methyl-6-(2,3,4,5-tetrahydro-1H-3-benzazepin-7-yloxy)-3-pyridinecarboxamide (D40) (1.04 g, 3.5 mmol) in dichloromethane (12 ml) containing acetic acid (240 µL) at 0° C. was treated dropwise with cyclobutanone (400 µL, 5.3 mmol) and then stirred at room temperature for 1 hour. The mixture was then cooled to 0° C. and treated portionwise with sodium triacetoxyborohydride (1.11 g, 5.3 mmol) and stirred at room temperature for 16 hours. The solution was carefully basified with 2N sodium hydroxide, stirred for 30 minutes and then extracted with dichloromethane. The combined extracts were washed with brine, dried over anhydrous sodium sulphate and concentrated in vacuo. The crude material was purified by column chromatography eluting with dichloromethane then a mixture of 0.880 ammonia:methanol:dichloromethane (1:9:90) to afford the title compound (E121); MS (ES+) m/e 352 [M+H]$^+$.

Example 122

5-(3-Cyclobutyl-2,3,4,5-tetrahydro-1H-benzo[d]azepin-7-yloxy)-pyrazine-2-carboxylic acid methyl ester (E122)

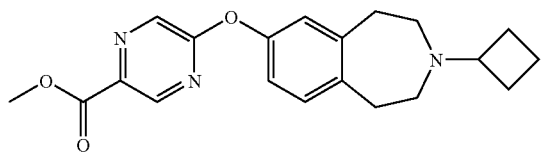

Sodium hydride (60% disp. in mineral oil, 332 mg, 8.3 mmol) was added to a stirred solution of 3-cyclobutyl-2,3,4,5-tetrahydro-1H-benzo[d]azepin-7-ol (E3) (1.64 g, 7.5 mmol) in dimethyl formamide (4 ml). After 0.5 hours, a solution of 5-chloro-pyrazine-2-carboxylic acid methyl ester (1.95 g, 11.3 mmol) in dimethyl formamide (8 ml) was added and the reaction mixture was stirred at room temperature for 1 hour. The reaction mixture was diluted with dichloromethane and the organic layer was washed with water, brine and dried over magnesium sulfate. The organic layer was filtered, concentrated in vacuo and the resulting residue was purified by column chromatography eluting with a mixture of 0.880 ammonia:ethanol:dichloromethane (1:9:90) to afford the title compound (E122). MS (ES+) m/e 354 [M+H]$^+$.

Example 123a 5-(3-Cyclobutyl-2,3,4,5-tetrahydro-1H-benzo[d]azepin-7-yloxy)-pyrazine-2-carboxylic acid (E123a)

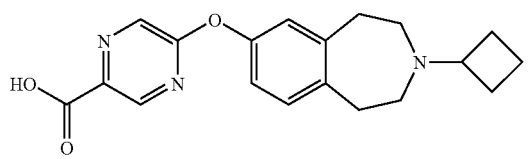

5-(3-Cyclobutyl-2,3,4,5-tetrahydro-1H-benzo[d]azepin-7-yloxy)-pyrazine-2-carboxylic acid methyl ester (E122) (880 mg, 2.5 mmol) was dissolved in a mixture of ethanol (15 ml) and 2N sodium hydroxide (4 ml). The resulting mixture was stirred at room temperature for 0.5 hours and then concentrated in vacuo to remove the organic solvents. The reaction mixture was then acidified to pH 5 (2N hydrochloric acid) and the resulting precipitates were filtered, washed with water and dried under vacuum to afford the title compound (E123a); MS (ES+) m/e 340 [M+H]$^+$.

Example 123

1-[5-(3-Cyclobutyl-2,3,4,5-tetrahydro-1H-benzo[d]azepin-7-yloxy)-pyrazin-2-yl]-1-morpholin-4-yl-methanone (E123)

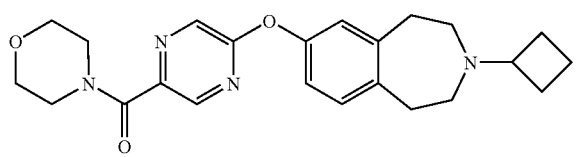

Step 1: 5-(3-Cyclobutyl-2,3,4,5-tetrahydro-1H-benzo[d]azepin-7-yloxy)-pyrazine-2-carbonyl chloride Thionyl chloride (5 ml) was added slowly to 5-(3-cyclobutyl-2,3,4,5-tetrahydro-1H-benzo[d]azepin-7-yloxy)-pyrazine-2-carboxylic acid (E123a) (485 mg). The resulting reaction mixture was stirred at room temperature for 1 hour and then heated at reflux for a further 1 hour. The reaction mixture was cooled, diluted with toluene and concentrated in vacuo to afford the title compound which was used without further characterisation.

Step 2: 1-[5-(3-Cyclobutyl-2,3,4,5-tetrahydro-1H-benzo[d]azepin-7-yloxy)-pyrazin-2-yl]-1-morpholin-4-yl-methanone Morpholine (0.17 ml, 2.0 mmol) was added to a stirred solution of the product of step 1 (394 mg, 1 mmol) and diethylaminomethyl polystyrene (1.88 g, 3.2 mmol/g, 6 mmol) in dichloromethane (10 ml). The resulting mixture was allowed to stir at room temperature for 24 hours and the filtered. The filtrate was concentrated in vacuo and the resulting crude residue was purified column chromatography eluting with a mixture of 0.880 ammonia:ethanol:dichloromethane (1:9:90) to afford the title compound (E123). MS (ES+) m/e 409 [M+H]$^+$.

Examples 124 and 126-127

Examples 124 and 126-127 (E124 and E126-E127) were prepared from the product of Example 123, step 1 and the appropriate amine indicated in the table using an analogous method to that described for Example 123, step 2:

| Example | Amine | LC/MS (M + H$^+$) |
|---|---|---|
| 5-(3-Cyclobutyl-2,3,4,5-tetrahydro-1H-benzo[d]azepin-7-yloxy)-pyrazine-2-carboxylic acid ethylmethyl amide (E124) | N-Ethylmethyl amine | 381 |
| 1-[5-(3-Cyclobutyl-2,3,4,5-tetrahydro-1H-benzo[d]azepin-7-yloxy)-pyrazin-2-yl]-1-piperidin-4-yl-methanone (E126) | Piperidine | 407 |
| 1-[5-(3-Cyclobutyl-2,3,4,5-tetrahydro-1H-benzo[d]azepin-7-yloxy)-pyrazin-2-yl]-1-pyrrolidin-4-yl-methanone (E127) | Pyrrolidine | 393 |

Example 125

5-(3-Cyclobutyl-2,3,4,5-tetrahydro-1H-benzo[d]azepin-7-yloxy)-pyrazine-2-carboxylic acid methyl amide (E125)

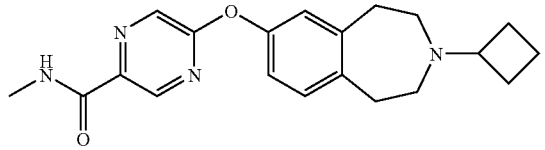

The product of Example 123, step 1 (1.59 mmol) in dry dichloromethane (10 ml) was treated with methylamine (5 ml, 10 mmol, 2M solution in THF) and stirred at room temperature for 18 hours. The mixture was reduced in vacuo and the resulting crude material was applied to a SCX ion exchange cartridge (Varian bond-elute, 10 g) and washed with methanol and then a mixture of 0.880 ammonia:methanol (1:9). The basic fractions were then reduced and the crude product purified by column chromatography eluting with a mixture of 0.880 ammonia:ethanol:dichloromethane (0.2:1.8:98 and then 0.4:3.6:96) to afford the title compound (E125). $^1$H NMR (CDCl$_3$) δ 8.91 (1H, d, 1.3 Hz), 8.26 (1H, d, 1.3 Hz), 7.61 (1H, br quartet, 4.8 Hz), 7.15 (1H, m), 6.92 (2H, m), 3.03 (3H, d, 5.1 Hz), 2.93 (4H, m), 2.79 (1H, m), 2.47 (4H, m), 2.08 (2H, m), 1.91 (2H, m), 1.70-1.62 (2H, m).

Example 128

3-Cyclobutyl-7-phenoxy-2,3,4,5-tetrahydro-1H-benzo[d]azepine (E128)

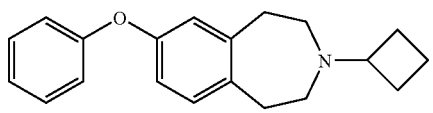

Sodium hydride (60% disp. in mineral oil, 96 mg, 2.4 mmol) was added to a stirred solution of 3-cyclobutyl-2,3,4,5-tetrahydro-1H-benzo[d]azepin-7-ol (E3) (435 mg, 2.0 mmol) and copper (I) bromide (402 mg, 2.8 mmol) in pyridine (10 ml) at 0° C. After stirring for 0.5 hour at room temperature, iodobenzene (0.45 ml, 4.0 mmol) was added and the reaction mixture was heated to reflux for 24 hours. The reaction was allowed to cool, filtered and the filtrate then concentrated in vacuo. The crude residue was dissolved with ethyl acetate and washed with water and brine. The organic layer was dried over magnesium sulfate, filtered and concentrated in vacuo and the resulting residue purified by column chromatography eluting with a mixture of 0.880 ammonia:ethanol:dichloromethane (0.25:2.25:97.5 to 1:9:90) to afford the title compound (E128); MS (ES+) m/e 294 [M+H]$^+$.

Examples 129-138

Examples 129-138 (E129-E138) were prepared from 3-cyclobutyl-2,3,4,5-tetrahydro-1H-benzo[d]azepin-7-ol (E3) and the appropriate aromatic halide indicated in the table using an analogous method to that described for Example 128 (E128):

| Example | Aromatic halide | LC/MS (M + H$^+$) |
| --- | --- | --- |
| 1-[4-(3-Cyclobutyl-2,3,4,5-tetrahydro-1H-benzo[d]azepin-7-yloxy)-phenyl]-1-morpholin-4-yl-methanone (E129) | 1-(4-Iodo-phenyl)-1-morpholin-4-yl-methanone (D22) | 407 |
| 4-(3-Cyclobutyl-2,3,4,5-tetrahydro-1H-benzo[d]azepin-7-yloxy)-N-cyclopropylmethyl-benzamide (E130) | 4-Iodo-N-cyclopropylmethyl-benzamide (D23) | 391 |
| 1-[4-(3-Cyclobutyl-2,3,4,5-tetrahydro-1H-benzo[d]azepin-7-yloxy)-phenyl]-1-pyrrolidin-1-yl-methanone (E131) | 1-(4-Iodo-phenyl)-1-pyrrolidin-1-yl-methanone (D24) | 391 |
| N-Cyclobutyl-4-(3-Cyclobutyl-2,3,4,5-tetrahydro-1H-benzo[d]azepin-7-yloxy)-benzamide (E132) | 4-Iodo-N-cyclobutyl-benzamide (D25) | 391 |
| 4-(3-Cyclobutyl-2,3,4,5-tetrahydro-1H-benzo[d]azepin-7-yloxy)-N,N-diethyl-benzamide (E133) | 4-Iodo-N,N-diethyl-benzamide (D26) | 393 |
| N-(2-Cyano-ethyl)-4-(3-cyclobutyl-2,3,4,5-tetrahydro-1H-benzo[d]azepin-7-yloxy)-N-methyl-benzamide (E134) | 4-Iodo-N-(2-cyano-ethyl)-N-methyl-benzamide (D27) | 404 |
| 1-[3-(3-Cyclobutyl-2,3,4,5-tetrahydro-1H-benzo[d]azepin-7-yloxy)-phenyl]-1-morpholin-4-yl-methanone (E135) | 1-(3-Iodo-phenyl)-1-morpholin-4-yl-methanone (D28) | 407 |
| 3-(3-Cyclobutyl-2,3,4,5-tetrahydro-1H-benzo[d]azepin-7-yloxy)-N-cyclopropylmethyl-benzamide (E136) | 3-Iodo-N-cyclopropylmethyl-benzamide (D29) | 391 |
| 3-Cyclobutyl-7-[4-(morpholine-4-sulfonyl)-phenoxy]-2,3,4,5-tetrahydro-1H-benzo[d]azepine (E137) | 4-(4-Iodo-benzenesulfonyl)-morpholine (D30) | 443 |
| 4-(3-Cyclobutyl-2,3,4,5-tetrahydro-1H-benzo[d]azepin-7-yloxy)-N,N-diethyl-benzenesulfonamide (E138) | 4-Iodo-N,N-diethyl-benzenesulfonamide (D31) | 429 |

Example 139

7-Benzyloxy-3-cyclohexyl-2,3,4,5-tetrahydro-1H-benzo[d]azepine (E139)

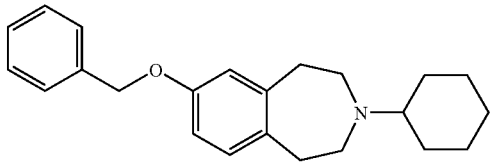

Example 139 (E139) was prepared from Description 2 (D2) and cyclohexanone using the method described for Example 1; MS (ES+) m/e 336 [M+H]$^+$.

Example 140

3-Cyclobutyl-7-{[2-(1-piperidinyl)-5-pyrimidinyl]oxy}-2,3,4,5-tetrahydro-1H-3-benzazepine (E140)

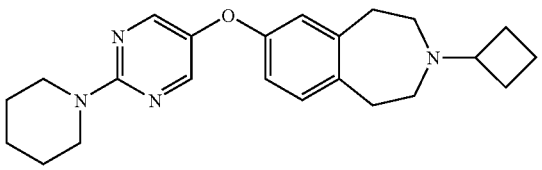

Sodium hydride (60% disp. in mineral oil, 44 mg, 1.1 mmol) was added to a stirred solution of 3-cyclobutyl-2,3,4,5-tetrahydro-1H-benzo[d]azepin-7-ol (E3) (200 mg, 0.92 mmol) and copper (I) bromide (184 mg, 1.3 mmol) in pyridine (10 ml) at 0° C. After stirring for 0.5 hour at room temperature, 5-bromo-2-(1-piperidinyl)pyrimidine (D32) (0.669 g, 2.8 mmol) was added and the reaction mixture heated at reflux for 2 hours. The reaction was allowed to cool, filtered and the filtrate was concentrated in vacuo. The crude residue was dissolved with ethyl acetate and washed with water and brine. The organic layer was dried (magnesium sulfate), filtered and concentrated in vacuo. Purification of the resulting residue by column chromatography eluting with a mixture of 0.880 ammonia:ethanol:dichloromethane (0.25:2.25:97.5 to 1:9:90) afforded the title compound (E140). MS (ES+) m/e 379 [M+H]$^+$.

Examples 141-143

Examples 141-143 (E141-E143) were prepared from 3-cyclobutyl-2,3,4,5-tetrahydro-1H-benzo[d]azepin-7-ol (E3) and the appropriate bromides indicated in the table using an analogous method to that described for Example 140 (E140):

| Example | Bromide | LC/MS (M + H$^+$) |
|---|---|---|
| 3-Cyclobutyl-7-{[2-(1-pyrrolidinyl)-5-pyrimidinyl]oxy}-2,3,4,5-tetrahydro-1H-3-benzazepine (E141) | 5-Bromo-2-(1-pyrrolidinyl)pyrimidine (D33) | 365 |
| 3-Cyclobutyl-7-{[2-(1,1-dioxido-4-thiomorpholinyl)-5-pyrimidinyl]oxy}-2,3,4,5-tetrahydro-1H-3-benzazepine (E142) | 4-(5-Bromo-2-pyrimidinyl)thiomorpholine 1,1-dioxide (D34) | 429 |
| 5-[(3-Cyclobutyl-2,3,4,5-tetrahydro-1H-3-benzazepin-7-yl)oxy]-N-methyl-2-pyrimidinamine (E143) | 5-Bromo-N-methyl-2-pyrimidinamine (D35) | 325 |

Example 144

3-Cyclobutyl-7-{[2-(methyloxy)-5-pyrimidinyl]oxy}-2,3,4,5-tetrahydro-1H-3-benzazepine (E144)

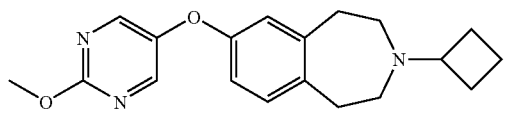

Example 144 (E144) was prepared from 3-cyclobutyl-2,3,4,5-tetrahydro-1H-benzo[d]azepin-7-ol (E3) and 5-bromo-2-(methyloxy)pyrimidine (PCT Int. Appl. PCT (2002), WO 02/62423) using the method described for Example 140 (E140); MS (ES+) m/e 326 [M+H]$^+$.

Examples 145-147

Examples 145-147 (E145-E147) were prepared from 3-cyclobutyl-7-(piperidin-4-yloxy)-2,3,4,5-tetrahydro-1H-benzo[d]azepine (E6) and the appropriate acid indicated in the table using an analogous method to that described for Example 13 (E13):

| Example | Acid | LC/MS (M + H$^+$) |
|---|---|---|
| 1-[4-({4-[(3-Cyclobutyl-2,3,4,5-tetrahydro-1H-3-benzazepin-7-yl)oxy]-1-piperidinyl}carbonyl)phenyl]-2-pyrrolidinone (E145) | 4-(2-Oxo-1-pyrrolidinyl)benzoic acid | 488 |
| 3-Cyclobutyl-7-[(1-{[3-(methylsulfonyl)phenyl]carbonyl}-4-piperidinyl)oxy]-2,3,4,5-tetrahydro-1H-3-benzazepine (E146) | 3-(Methylsulfonyl)benzoic acid | 483 |
| 3-Cyclobutyl-7-({1-[(1,1-dioxido-3,4-dihydro-2H-1-benzothiopyran-6-yl)carbonyl]-4-piperidinyl}oxy)-2,3,4,5-tetrahydro-1H-3-benzazepine (E147) | 3,4-Dihydro-2H-1-benzothiopyran-6-carboxylic acid 1,1-dioxide | 509 |

Examples 148-150

Examples 148-150 (E148-E150) were prepared from 3-cyclobutyl-2,3,4,5-tetrahydro-1H-benzo[d]azepin-7-ol (E3) and the appropriate alcohol indicated in the table the method used for the preparation of Example 5a (E5a) followed by the method described for the preparation of Example 5 (E5).

| Example | Alcohol | LC/MS (M + H+) |
| --- | --- | --- |
| 3-Cyclobutyl-7-{[(3S)-3-pyrrolidinylmethyl]oxy}-2,3,4,5-tetrahydro-1H-3-benzazepine (E148) | 1,1-Dimethylethyl (3S)-3-(hydroxymethyl)-1-pyrrolidinecarboxylate | 301 |
| 3-Cyclobutyl-7-{[(3S)-3-piperidinylmethyl]oxy}-2,3,4,5-tetrahydro-1H-3-benzazepine (E149) | 1,1-Dimethylethyl (3S)-3-(hydroxymethyl)-1-piperidinecarboxylate | 315 |
| 3-Cyclobutyl-7-[(3S)-3-piperidinyloxy]-2,3,4,5-tetrahydro-1H-3-benzazepine (E150) | 1,1-Dimethylethyl (3S)-3-hydroxy-1-piperidinecarboxylate | 301 |

Examples 151-153

Examples 151-153 (E151-E153) were prepared from the appropriate amine indicated in the table and morpholine carbamoyl chloride using the method described for Example 52:

| Example | Amine | LC/MS (M + H+) |
| --- | --- | --- |
| 3-Cyclobutyl-7-({[(3S)-1-(4-morpholinylcarbonyl)-3-piperidinyl]methyl}oxy)-2,3,4,5-tetrahydro-1H-3-benzazepine (E151) | 3-Cyclobutyl-7-{[(3S)-3-piperidinylmethyl]oxy}-2,3,4,5-tetrahydro-1H-3-benzazepine (E149) | 428 |
| 3-Cyclobutyl-7-({[(3S)-1-(4-morpholinylcarbonyl)-3-pyrrolidinyl]methyl}oxy)-2,3,4,5-tetrahydro-1H-3-benzazepine (E152) | 3-Cyclobutyl-7-{[(3S)-3-pyrrolidinylmethyl]oxy}-2,3,4,5-tetrahydro-1H-3-benzazepine (E148) | 414 |
| 3-Cyclobutyl-7-{[(3S)-1-(4-morpholinylcarbonyl)-3-piperidinyl]oxy}-2,3,4,5-tetrahydro-1H-3-benzazepine (E153) | 3-Cyclobutyl-7-[(3S)-3-piperidinyloxy]-2,3,4,5-tetrahydro-1H-3-benzazepine (E150) | 414 |

Examples 154-156

Examples 154-156 (E154-E156) were prepared from the appropriate amine indicated in the table and 4-cyanobenzoyl chloride using an analogous method to that described for Example 43 (E43):

| Example | Amine | LC/MS (M + H+) |
| --- | --- | --- |
| 4-[((3S)-3-{[(3-Cyclobutyl-2,3,4,5-tetrahydro-1H-3-benzazepin-7-yl)oxy]methyl}-1-piperidinyl)carbonyl]benzonitrile (E154) | 3-Cyclobutyl-7-{[(3S)-3-piperidinylmethyl]oxy}-2,3,4,5-tetrahydro-1H-3-benzazepine (E149) | 444 |
| 4-[((3S)-3-{[(3-Cyclobutyl-2,3,4,5-tetrahydro-1H-3-benzazepin-7-yl)oxy]methyl}-1-pyrrolidinyl)carbonyl]benzonitrile (E155) | 3-Cyclobutyl-7-{[(3S)-3-pyrrolidinylmethyl]oxy}-2,3,4,5-tetrahydro-1H-3-benzazepine (E148) | 430 |
| 4-({(3S)-3-[(3-Cyclobutyl-2,3,4,5-tetrahydro-1H-3-benzazepin-7-yl)oxy]-1-piperidinyl}carbonyl)benzonitrile (E156) | 3-Cyclobutyl-7-[(3S)-3-piperidinyloxy]-2,3,4,5-tetrahydro-1H-3-benzazepine (E150) | 430 |

Examples 157-159

Examples 157-159 (E157-E159) were from prepared from the appropriate amine indicated in the table and tetrahydropyran-4-carboxylic acid using an analogous method to that described for Example 13 (E13):

| Example | Amine | LC/MS (M + H$^+$) |
|---|---|---|
| 3-Cyclobutyl-7-({[(3S)-1-(tetrahydro-2H-pyran-4-ylcarbonyl)-3-pyrrolidinyl]methyl}oxy)-2,3,4,5-tetrahydro-1H-3-benzazepine (E157) | 3-Cyclobutyl-7-{[(3S)-3-pyrrolidinylmethyl]oxy}-2,3,4,5-tetrahydro-1H-3-benzazepine (E148) | 413 |
| 3-Cyclobutyl-7-({[(3S)-1-(tetrahydro-2H-pyran-4-ylcarbonyl)-3-piperidinyl]methyl}oxy)-2,3,4,5-tetrahydro-1H-3-benzazepine (E158) | 3-Cyclobutyl-7-{[(3S)-3-piperidinylmethyl]oxy}-2,3,4,5-tetrahydro-1H-3-benzazepine (E149) | 427 |
| 3-Cyclobutyl-7-{[(3S)-1-(tetrahydro-2H-pyran-4-ylcarbonyl)-3-piperidinyl]oxy}-2,3,4,5-tetrahydro-1H-3-benzazepine (E159) | 3-Cyclobutyl-7-[(3S)-3-piperidinyloxy]-2,3,4,5-tetrahydro-1H-3-benzazepine (E150) | 413 |

Example 160

6-{4-[(3-Cyclobutyl-2,3,4,5-tetrahydro-1H-3-benzazepin-7-yl)oxy]-1-piperidinyl}-3-pyridinecarbonitrile (E160)

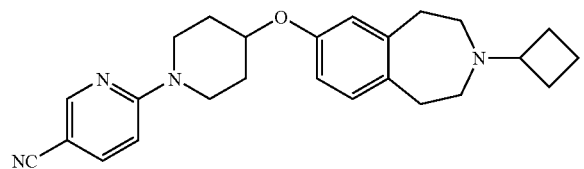

3-Cyclobutyl-7-(piperidin-4-yloxy)-2,3,4,5-tetrahydro-1H-benzo[d]azepine (E6) (60 mg, 0.2 mmol), 6-chloronicotinonitrile (31 mg, 0.22 mmol) and triethylamine (0.03 ml, 0.22 mmol) were dissolved in acetonitrile (2 ml) and heated to 180° C. in a microwave reactor for 10 minutes. The reaction mixture was diluted with ethyl acetate and washed with water, brine and dried (magnesium sulfate). The organic layer was filtered, concentrated in vacuo and the resulting residue purified by column chromatography eluting with a mixture of 0.880 ammonia:ethanol:dichloromethane (0.25:2.25:97.5 to 1:9:90) to afford the title compound (E160); MS (ES+) m/e 403 [M+H]$^+$.

Examples 161-166

Examples 161-166 (E161-E166) were prepared from 3-cyclobutyl-7-(piperidin-4-yloxy)-2,3,4,5-tetrahydro-1H-benzo[d]azepine (E6) and the appropriate chloride indicated in the table using an analogous method to that described for Example 160 (E160):

| Example | Chloride | LC/MS (M + H$^+$) |
|---|---|---|
| 6-{4-[(3-Cyclobutyl-2,3,4,5-tetrahydro-1H-3-benzazepin-7-yl)oxy]-1-piperidinyl}-N-(cyclopropylmethyl)-3-pyridinecarboxamide (E161) | 6-Chloro-N-(cyclopropylmethyl)-3-pyridinecarboxamide (D36) | 475 |
| 7-({1-[5-(1-Azetidinylcarbonyl)-2-pyridinyl]-4-piperidinyl}oxy)-3-cyclobutyl-2,3,4,5-tetrahydro-1H-3-benzazepine (E162) | 5-(1-Azetidinylcarbonyl)-2-chloropyridine (D37) | 461 |
| 3-Cyclobutyl-7-({1-[5-(4-morpholinylcarbonyl)-2-pyridinyl]-4-piperidinyl}oxy)-2,3,4,5-tetrahydro-1H-3-benzazepine (E163) | 1-(6-Chloro-pyridin-3-yl)-1-morpholin-4-yl-methanone (D5) | 491 |
| 6-{4-[(3-Cyclobutyl-2,3,4,5-tetrahydro-1H-3-benzazepin-7-yl)oxy]-1-piperidinyl}-N-methyl-3-pyridinecarboxamide (E164) | 6-Chloro-N-methyl-nicotinamide (D10) | 435 |
| 2-{4-[(3-Cyclobutyl-2,3,4,5-tetrahydro-1H-3-benzazepin-7-yl)oxy]-1-piperidinyl}-4-pyridinecarbonitrile (E165) | 2-Chloro-4-pyridine carbonitrile | 403 |
| 3-Cyclobutyl-7-{[1-(2-pyrazinyl)-4-piperidinyl]oxy}-2,3,4,5-tetrahydro-1H-3-benzazepine (E166) | 2-Chloropyrazine | 379 |

Example 167a

Ethyl 4-[(3-cyclobutyl-2,3,4,5-tetrahydro-1H-3-benzazepin-7-yl)oxy]butanoate (E167a)

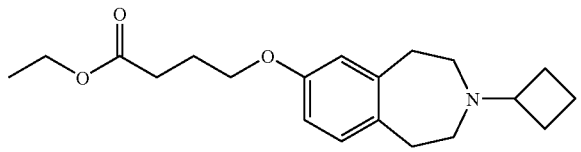

Ethyl 4-bromobutyrate (2 ml, 13.8 mmol) was added to a stirred solution of 3-cyclobutyl-2,3,4,5-tetrahydro-1H-benzo[d]azepin-7-ol (E3) (2.00 g, 9.2 mmol) and potassium carbonate (3.8 g, 27.6 mmol) in 2-butanone (50 ml). After stirring at reflux for 24 hours, the reaction mixture was cooled to room temperature, filtered and concentrated in vacuo. The resulting crude material was purified by column chromatography eluting with a mixture of methanol:dichloromethane (5:95) to afford the title compound (E167a). MS (ES+) m/e 332 [M+H]$^+$

Example 167b

4-[(3-Cyclobutyl-2,3,4,5-tetrahydro-1H-3-benzazepin-7-yl)oxy]butanoic acid (E167b)

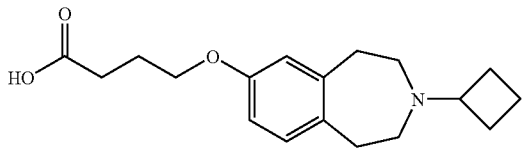

Ethyl 4-[(3-cyclobutyl-2,3,4,5-tetrahydro-1H-3-benzazepin-7-yl)oxy]butanoate (E167a) (1.5 g, 4.5 mmol) was diluted in ethanol (30 ml) and treated with 2N sodium hydroxide (7.9 ml). After stirring at reflux for 24 hours, the reaction mixture was cooled to room temperature, filtered and concentrated in vacuo. The crude mixture was applied to a SCX ion exchange cartridge (Varian bond-elute) and washed with water, methanol and then a mixture of 0.880 ammonia:methanol (1:9). The combined basic fractions were reduced in vacuo to afford the title compound (E167b) as the ammonium salt. MS (ES+) m/e 303 [M+H]$^+$

Example 167

3-Cyclobutyl-7-{[4-oxo-4-(1-piperidinyl)butyl]oxy}-2,3,4,5-tetrahydro-1H-3-benzazepine (E167)

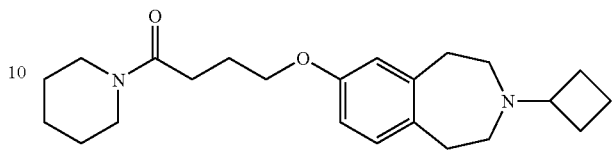

Step 1: 3-Cyclobutyl-7-{[4-(1H-imidazol-1-yl)-4-oxobutyl]oxy}-2,3,4,5-tetrahydro-1H-3-benzazepine 4-[(3-Cyclobutyl-2,3,4,5-tetrahydro-1H-3-benzazepin-7-yl)oxy]butanoic acid (E167b) (0.90 g, 2.8 mmol) was dissolved in dimethylformamide (10 ml) and treated with 1,1'-carbonyl diimidazole (0.59 g, 3.6 mmol). After stirring at room temperature for 2.5 hours, the reaction mixture concentrated in vacuo. The crude residue was dissolved in dichloromethane, washed with brine and dried (sodium sulfate). The organic layer was filtered and concentrated in vacuo and the crude residue used directly in the next step without further purification.

Step 2: 3-Cyclobutyl-7-{[4-oxo-4-(1-piperidinyl)butyl]oxy}-2,3,4,5-tetrahydro-1H-3-benzazepine (E167)

Piperidine (0.1 ml, 1.1 mmol) was added to a stirred solution of 3-cyclobutyl-7-{[4-(1H-imidazol-1-yl)-4-oxobutyl]oxy}-2,3,4,5-tetrahydro-1H-3-benzazepine (E167, Step 1) (150 mg, 0.42 mmol) in dichloromethane (5 ml). After stirring at room temperature for 5 days the reaction mixture was concentrated in vacuo and the resulting residue was purified by column chromatography eluting with a mixture of 0.880 ammonia:ethanol:dichloromethane (1:9:90) to afford the title compound (E167); MS (ES+) m/e 371 [M+H]$^+$.

Examples 168-170

Examples 168-170 (E168-E170) were prepared from Example 167 Step 1, using an analogous method to that described for Example 167 Step 2 substituting piperidine for the appropriate amine indicated in the table:

| Example | Amine | LC/MS (M + H$^+$) |
|---|---|---|
| 3-Cyclobutyl-7-{[4-oxo-4-(1-pyrrolidinyl)butyl]oxy}-2,3,4,5-tetrahydro-1H-3-benzazepine (E168) | Pyrrolidine | 357 |
| 4-[(3-Cyclobutyl-2,3,4,5-tetrahydro-1H-3-benzazepin-7-yl)oxy]-N-cyclopentylbutanamide (E169) | Cyclopentylamine | 371 |
| 4-[(3-Cyclobutyl-2,3,4,5-tetrahydro-1H-3-benzazepin-7-yl)oxy]-N-methylbutanamide (E170) | Methylamine | 317 |

Examples 171-176

Examples 171-176 (E171-E176) were prepared from Example 123, Step 1 and the appropriate amine indicated in the table using an analogous method to that described for Example 123 Step 2 (E123):

| Example | Amine | LC/MS (M + H⁺) |
|---|---|---|
| 5-[(3-Cyclobutyl-2,3,4,5-tetrahydro-1H-3-benzazepin-7-yl)oxy]-N-(1-methylethyl)-2-pyrazinecarboxamide (E171) | Isopropylamine | 381 |
| 5-[(3-Cyclobutyl-2,3,4,5-tetrahydro-1H-3-benzazepin-7-yl)oxy]-N-(tetrahydro-2H-pyran-4-yl)-2-pyrazinecarboxamide (E172) | Tetrahydro-2H-pyran-4-amine | 423 |
| 7-{[5-(1-Azetidinylcarbonyl)-2-pyrazinyl]oxy}-3-cyclobutyl-2,3,4,5-tetrahydro-1H-3-benzazepine (E173) | Azetidine | 379 |
| 5-[(3-Cyclobutyl-2,3,4,5-tetrahydro-1H-3-benzazepin-7-yl)oxy]-N,N-diethyl-2-pyrazinecarboxamide (E174) | Diethylamine | 395 |
| 5-[(3-Cyclobutyl-2,3,4,5-tetrahydro-1H-3-benzazepin-7-yl)oxy]-N-[2-(methyloxy)ethyl]-2-pyrazinecarboxamide (E175) | 2-(Methyloxy)ethylamine | 397 |
| 5-[(3-Cyclobutyl-2,3,4,5-tetrahydro-1H-3-benzazepin-7-yl)oxy]-N-ethyl-2-pyrazinecarboxamide (E176) | Ethylamine | 367 |

Example 177a

5-[(3-Cyclobutyl-2,3,4,5-tetrahydro-1H-3-benzazepin-7-yl)oxy]-2-pyrimidinecarbonitrile (E177a)

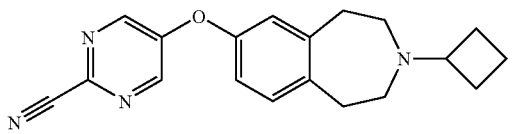

3-Cyclobutyl-2,3,4,5-tetrahydro-1H-3-benzazepin-7-ol (E3) (1.81 g, 8.33 mmol) was dissolved in pyridine (40 ml) and sodium hydride (60% in mineral oil, 0.40 g, 10.0 mmol) was added with stirring under argon at 0° C. The mixture was left to stir for 5 minutes. Copper (I) bromide (1.68 g, 11.7 mmol) was added and the mixture allowed to warm to room temperature over 30 minutes. 5-Bromo-2-pyrimidinecarbonitrile (D38) (2.30 g, 12.5 mmol) in pyridine (8 ml) was added and the mixture heated at 100° C. for 1 hour. The mixture was allowed to cool to room temperature and the solvent removed in vacuo. The crude product was purified by column chromatography, eluting with a mixture of 0.880 ammonia:methanol:dichloromethane (0.2:1.8:98) to afford the title compound (E177a); MS (ES+) m/e 321 [M+H]⁺.

Example 177b

5-[(3-Cyclobutyl-2,3,4,5-tetrahydro-1H-3-benzazepin-7-yl)oxy]-2-pyrimidinecarboxylic acid (E177b)

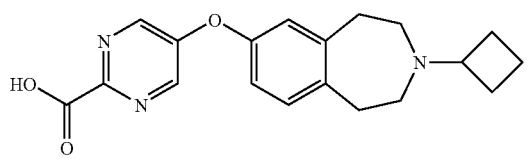

5-[(3-Cyclobutyl-2,3,4,5-tetrahydro-1H-3-benzazepin-7-yl)oxy]-2-pyrimidinecarbonitrile (E177a) (1.22 g, 3.81 mmol) was dissolved in ethanol (20 ml), treated with 10% sodium hydroxide solution (20 ml) and heated under reflux for 90 minutes. The mixture was cooled to room temperature and applied to a SCX ion exchange column (Varian bond-elute, 10 g) eluting with water, methanol and then a mixture of 0.880 ammonia:methanol (1:9). The basic fractions were combined and concentrated in vacuo to afford the title compound (E177b); MS (ES+) m/e 340 [M+H]⁺.

Example 177

3-Cyclobutyl-7-{[2-(4-morpholinylcarbonyl)-5-pyrimidinyl]oxy}-2,3,4,5-tetrahydro-1H-3-benzazepine (E177)

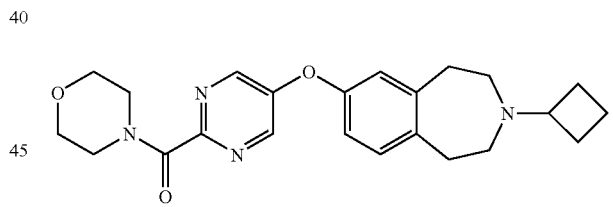

5-[(3-Cyclobutyl-2,3,4,5-tetrahydro-1H-3-benzazepin-7-yl)oxy]-2-pyrimidinecarboxylic acid (E177b) (130 mg, 0.37 mmol) was dissolved in dimethylformamide (4 ml), treated with 1,1'-carbonyldiimidazole (180 mg, 1.11 mmol) and left to stir under argon at room temperature for 5 hours. The mixture was treated with morpholine (0.19 ml, 2.22 mmol) and allowed to stir at room temperature for 18 hours. The reaction mixture was concentrated in vacuo and the resulting residue purified by column chromatography eluting with a mixture of 0.880 ammonia:methanol:dichloromethane (0.5:1.5:95) to afford the title compound (E177). MS (ES+) m/e 409 [M+H]⁺.

Examples 178-186

Examples 178-186 (E178-E186) were prepared from Example 177b (E177b) and the appropriate amine indicated in the table using an analogous method to that described for Example 177 (E177):

| Example | Amine | LC/MS (M + H+) |
|---|---|---|
| 5-[(3-Cyclobutyl-2,3,4,5-tetrahydro-1H-3-benzazepin-7-yl)oxy]-N-(cyclopropylmethyl)-2-pyrimidinecarboxamide (E178) | Cyclopropylmethylamine | 393 |
| 5-[(3-Cyclobutyl-2,3,4,5-tetrahydro-1H-3-benzazepin-7-yl)oxy]-N-ethyl-2-pyrimidinecarboxamide (E179) | Ethylamine | 367 |
| 7-{[2-(1-Azetidinylcarbonyl)-5-pyrimidinyl]oxy}-3-cyclobutyl-2,3,4,5-tetrahydro-1H-3-benzazepine (E180) | Azetidine | 379 |
| 5-[(3-Cyclobutyl-2,3,4,5-tetrahydro-1H-3-benzazepin-7-yl)oxy]-N-ethyl-N-methyl-2-pyrimidinecarboxamide (E181) | Ethyl(methyl)amine | 381 |
| N-Cyclobutyl-5-[(3-cyclobutyl-2,3,4,5-tetrahydro-1H-3-benzazepin-7-yl)oxy]-2-pyrimidinecarboxamide (E182) | Cyclobutylamine | 393 |
| 5-[(3-Cyclobutyl-2,3,4,5-tetrahydro-1H-3-benzazepin-7-yl)oxy]-N-(tetrahydro-2H-pyran-4-yl)-2-pyrimidinecarboxamide (E183) | Tetrahydro-2H-pyran-4-amine | 423 |
| 3-Cyclobutyl-7-{[2-(1-pyrrolidinylcarbonyl)-5-pyrimidinyl]oxy}-2,3,4,5-tetrahydro-1H-3-benzazepine (E184) | Pyrrolidine | 393 |
| 3-Cyclobutyl-7-{[2-(1-piperidinylcarbonyl)-5-pyrimidinyl]oxy}-2,3,4,5-tetrahydro-1H-3-benzazepine (E185) | Piperidine | 407 |
| 5-[(3-Cyclobutyl-2,3,4,5-tetrahydro-1H-3-benzazepin-7-yl)oxy]-N-methyl-2-pyrimidinecarboxamide (E186) | Methylamine | 353 |

Example 187a

5-[(3-Cyclobutyl-2,3,4,5-tetrahydro-1H-3-benzazepin-7-yl)oxy]-2-pyridinecarboxylic acid (E187a)

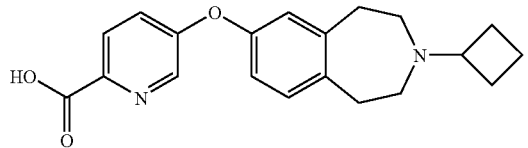

The title compound (E187a) was prepared from 5-[(3-cyclobutyl-2,3,4,5-tetrahydro-1H-3-benzazepin-7-yl)oxy]-2-pyridinecarbonitrile (E206) using an analogous method to that described for Example 177b (E177b); MS (ES+) m/e 339 [M+H]+.

Examples 187-195

Examples 187-195 (E187-E195) were prepared from 5-[(3-cyclobutyl-2,3,4,5-tetrahydro-1H-3-benzazepin-7-yl)oxy]-2-pyridinecarboxylic acid (E187a) and the appropriate amine indicated in the table using an analogous method to that described for Example 177 (E177):

| Example | Amine | LC/MS (M + H+) |
|---|---|---|
| 5-[(3-Cyclobutyl-2,3,4,5-tetrahydro-1H-3-benzazepin-7-yl)oxy]-N-methyl-2-pyridinecarboxamide (E187) | Methylamine | 352 |
| 5-[(3-Cyclobutyl-2,3,4,5-tetrahydro-1H-3-benzazepin-7-yl)oxy]-N-ethyl-2-pyridinecarboxamide (E188) | Ethylamine | 366 |
| 5-[(3-Cyclobutyl-2,3,4,5-tetrahydro-1H-3-benzazepin-7-yl)oxy]-N-ethyl-N-methyl-2-pyridinecarboxamide (E189) | Ethyl(methyl)amine | 380 |
| 5-[(3-Cyclobutyl-2,3,4,5-tetrahydro-1H-3-benzazepin-7-yl)oxy]-N,N-diethyl-2-pyridinecarboxamide (E190) | Diethylamine | 394 |
| 5-[(3-Cyclobutyl-2,3,4,5-tetrahydro-1H-3-benzazepin-7-yl)oxy]-N-ethyl-N-[2-(methyloxy)ethyl]-2-pyridinecarboxamide (E191) | Ethyl[2-(methyloxy)ethyl]amine | 424 |
| 3-Cyclobutyl-7-{[6-(1-pyrrolidinylcarbonyl)-3-pyridinyl]oxy}-2,3,4,5-tetrahydro-1H-3-benzazepine (E192) | Pyrrolidine | 392 |
| 3-Cyclobutyl-7-{[6-(4-morpholinylcarbonyl)-3-pyridinyl]oxy}-2,3,4,5-tetrahydro-1H-3-benzazepine (E193) | Morpholine | 408 |

-continued

| Example | Amine | LC/MS (M + H⁺) |
|---|---|---|
| 3-Cyclobutyl-7-{[6-(tetrahydro-1,4-oxazepin-4(5H)-ylcarbonyl)-3-pyridinyl]oxy}-2,3,4,5-tetrahydro-1H-3-benzazepine (E194) | Hexahydro-1,4-oxazepine | 422 |
| 5-[(3-Cyclobutyl-2,3,4,5-tetrahydro-1H-3-benzazepin-7-yl)oxy]-N-cyclopentyl-2-pyridinecarboxamide (E195) | Cyclopentylamine | 406 |

Example 196a

6-[(3-Cyclobutyl-2,3,4,5-tetrahydro-1H-3-benzazepin-7-yl)oxy]-3-pyridinecarboxylic acid methyl ester

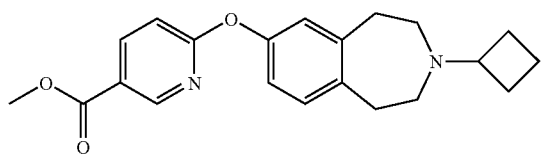

The title compound was prepared from 3-cyclobutyl-2,3,4,5-tetrahydro-1H-benzo[d]azepin-7-ol (E3) and methyl 6-chloro-3-pyridine carboxylate in an analogous manner to that described for E122; MS (ES+) m/e 353 [M+H]⁺.

Example 196b

6-[(3-Cyclobutyl-2,3,4,5-tetrahydro-1H-3-benzazepin-7-yl)oxy]-3-pyridinecarboxylic acid (E196b)

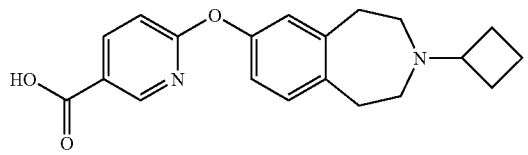

The title compounds was prepared from Example 196a (E126a) using the analogous methods to that described for Example 123a (E123a); MS (ES+) m/e 339 [M+H]⁺.

Example 196

6-[(3-Cyclobutyl-2,3,4,5-tetrahydro-1H-3-benzazepin-7-yl)oxy]-N-cyclopropyl-3-pyridinecarboxamide (E196)

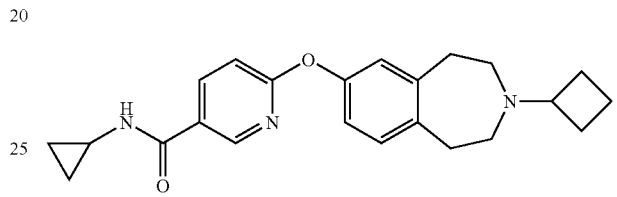

Carbonyl diimidazole (142 mg, 0.88 mmol) was added to a stirred solution of 6-[(3-cyclobutyl-2,3,4,5-tetrahydro-1H-3-benzazepin-7-yl)oxy]-3-pyridinecarboxylic acid (E196b) (150 mg, 0.44 mmol) in dichloromethane (5 ml). After stirring at room temperature for 3 hours, cyclopropylamine (0.15 ml, 2.2 mmol) was added and the mixture was allowed to stir for a further 18 hours. The reaction mixture was applied to a SCX ion cartridge (Varian bond-elute, 10 g) and washed with methanol and then a mixture of 0.880 ammonia:methanol (1:9). The combined basic fractions were concentrated in vacuo to afford the title compound (E196). MS (ES+) m/e 378 [M+H]⁺.

Examples 197-202

Examples 197-202 (E197-E202) were prepared from 6-[(3-cyclobutyl-2,3,4,5-tetrahydro-1H-3-benzazepin-7-yl)oxy]-3-pyridinecarboxylic acid (E196b) and the appropriate amine indicated in the table using an analogous method to that described for Example 196 (E196):

| Example | Amine | LC/MS (M + H⁺) |
|---|---|---|
| 6-[(3-Cyclobutyl-2,3,4,5-tetrahydro-1H-3-benzazepin-7-yl)oxy]-N-(1-methylethyl)-3-pyridinecarboxamide (E197) | Isopropylamine | 380 |
| 6-[(3-Cyclobutyl-2,3,4,5-tetrahydro-1H-3-benzazepin-7-yl)oxy]-N-ethyl-3-pyridinecarboxamide (E198) | Ethylamine | 366 |
| N-Cyclobutyl-6-[(3-cyclobutyl-2,3,4,5-tetrahydro-1H-3-benzazepin-7-yl)oxy]-3-pyridinecarboxamide (E199) | Cyclobutylamine | 392 |
| 6-[(3-Cyclobutyl-2,3,4,5-tetrahydro-1H-3-benzazepin-7-yl)oxy]-N-(tetrahydro-2H-pyran-4-yl)-3-pyridinecarboxamide (E200) | Tetrahydro-2H-pyran-4-amine | 422 |

-continued

| Example | Amine | LC/MS (M + H+) |
|---|---|---|
| 6-[(3-Cyclobutyl-2,3,4,5-tetrahydro-1H-3-benzazepin-7-yl)oxy]-N,N-diethyl-3-pyridinecarboxamide (E201) | Diethylamine | 394 |
| 6-[(3-Cyclobutyl-2,3,4,5-tetrahydro-1H-3-benzazepin-7-yl)oxy]-N-[2-(methyloxy)ethyl]-3-pyridinecarboxamide (E202) | [2-(Methyloxy)ethyl]amine | 396 |

Examples 203-205

Examples 203-205 (E203-205) were prepared from 3-cyclobutyl-2,3,4,5-tetrahydro-1H-benzo[d]azepin-7-ol (E3) and the appropriate aromatic iodide indicated in the table using an analogous method to that described for Example 128 (E128):

| Example | Iodide | LC/MS (M + H+) |
|---|---|---|
| 4-[(3-Cyclobutyl-2,3,4,5-tetrahydro-1H-3-benzazepin-7-yl)oxy]-N-ethyl-N-[2-(methyloxy)ethyl]benzamide (E203) | 4-Iodo-N-ethyl-N-[2-(methyloxy)ethyl]benzamide (D50) | 423 |
| 4-[(3-Cyclobutyl-2,3,4,5-tetrahydro-1H-3-benzazepin-7-yl)oxy]-N-methylbenzamide (E204) | 4-Iodo-N-methylbenzamide (D51) | 351 |
| 3-Cyclobutyl-7-(3-pyridinyloxy)-2,3,4,5-tetrahydro-1H-3-benzazepine (E205) | 3-Iodopyridine | 294 |

Example 206

5-[(3-Cyclobutyl-2,3,4,5-tetrahydro-1H-3-benzazepin-7-yl)oxy]-2-pyridinecarbonitrile (E206)

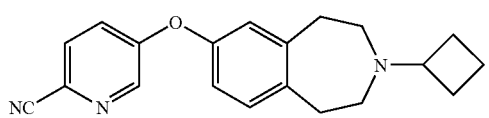

The title compound (E206) was prepared from 3-cyclobutyl-2,3,4,5-tetrahydro-1H-3-benzazepin-7-ol (E3) and 5-iodo-2-pyridinecarbonitrile (Biochemical Journal, 1973, 131(4), 625) according to the method outlined for E177a; MS (ES+) m/e 320 [M+H]+.

Examples 207-208

Examples 207-208 (E207-208) were prepared from 3-cyclobutyl-2,3,4,5-tetrahydro-1H-benzo[d]azepin-7-ol (E3) and the appropriate aromatic chloride indicated in the table using an analogous method to that described for Example 100 (E100):

| Example | Chloride | LC/MS (M + H+) |
|---|---|---|
| 3-Cyclobutyl-7-[(5-iodo-2-pyridinyl)oxy]-2,3,4,5-tetrahydro-1H-3-benzazepine (E207) | 2-Chloro-5-iodopyridine | 421 |
| 3-Cyclobutyl-7-[(5-nitro-2-pyridinyl)oxy]-2,3,4,5-tetrahydro-1H-3-benzazepine (E208) | 2-Chloro-5-nitropyridine | 340 |

Example 209

N-{6-[(3-Cyclobutyl-2,3,4,5-tetrahydro-1H-3-benzazepin-7-yl)oxy]-3-pyridinyl}acetamide (E209)

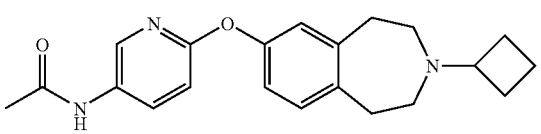

Iron filings (451 mg, 8.07 mmol) were added to a stirred solution of 3-cyclobutyl-7-[(5-nitro-2-pyridinyl)oxy)]-2,3,4,5-tetrahydro-1H-3-benzazepine (E208) (550 mg, 1.62 mmol) in a mixture of acetic acid:acetic anhydride solution (1:1, 10 ml) and heated at 80° C. for 16 hours. The reaction mixture was cooled, poured onto ice and taken to pH 8 with sodium bicarbonate. The product was extracted into ethyl acetate and the organic extract was then washed with brine and dried over sodium sulphate. The residue was purified by column chromatography eluting with a mixture of 0.880 ammonia:metha-

Example 210a

3-Cyclobutyl-7-[(5-nitro-1,3-thiazol-2-yl)oxy]-2,3,4,5-tetrahydro-1H-3-benzazepine (E210a)

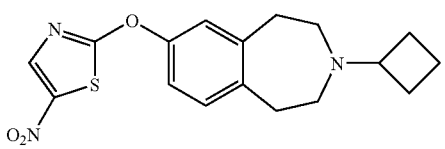

Sodium hydride (60% disp. in mineral oil, 150 mg, 3.66 mmol) was added to a stirred solution of 3-cyclobutyl-2,3,4,5-tetrahydro-1H-benzo[d]azepin-7-ol (E3) (530 mg, 2.43 mmol) in dimethylformamide (10 ml) at 5° C. After 0.5 hours a solution of 2-bromo-5-nitro-1,3-thiazole (1.0 g, 4.78 mmol) in dimethylformamide (5 ml) was added and the reaction mixture was allowed to warm to room temperature and stir for 2 hours. The reaction mixture was diluted with ethyl acetate and the organic layer was washed with water, brine, dried (sodium sulfate) and concentrated in vacuo. Purification by column chromatography eluting with a mixture of 0.880 ammonia:methanol:dichloromethane (0.25:2.25:97.5) afforded the title compound (E210a); MS (ES+) m/e 346 [M+H]$^+$.

Example 210

N-{2-[(3-Cyclobutyl-2,3,4,5-tetrahydro-1H-3-benzazepin-7-yl)oxy]-1,3-thiazol-5-yl}acetamide (E210)

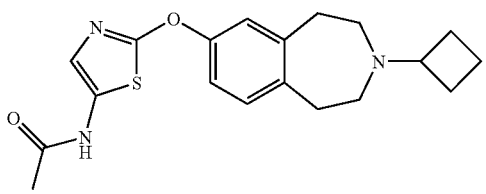

Iron powder (162 mg, 2.9 mmol) was added to a stirred solution of 3-cyclobutyl-7-[(5-nitro-1,3-thiazol-2-yl)oxy]-2,3,4,5-tetrahydro-1H-3-benzazepine (E210a) (162 mg, 0.47 mmol) in acetic acid (1 ml) and acetic anhydride (1 ml). The reaction mixture was stirred at 80° C. for 16 hours then cooled and poured onto ice. The solution was basified to pH 8 (sodium bicarbonate) and the resulting mixture was extracted with ethyl acetate. The organic layer was washed with brine and dried (sodium sulfate). Concentration in vacuo and subsequent purification of the resulting residue by column chromatography eluting with a mixture of 0.880 ammonia:methanol:dichloromethane (0.3:2.7:97) afforded the title compound (E210). MS (ES+) m/e 358 [M+H]$^+$.

Example 211

3-Cyclobutyl-7-[(5-nitro-2-thienyl)oxy]-2,3,4,5-tetrahydro-1H-3-benzazepine (E211)

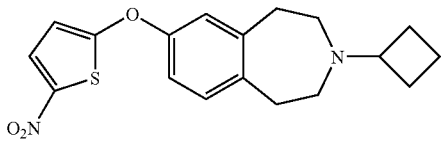

A mixture of 2-bromo-5-nitrothiophene (478 mg, 2.3 mmol), 3-cyclobutyl-2,3,4,5-tetrahydro-1H-benzo[d]azepin-7-ol (E3) (500 mg, 2.3 mmol) and potassium carbonate (765 mg, 5.5 mmol) in dimethylformamide (10 ml) was stirred at 80° C. for 16 hours. The reaction mixture was cooled, diluted with ethyl acetate and washed with water, brine and dried (sodium sulfate). Concentration in vacuo and purification of the resulting residue by column chromatography 0.880 ammonia:methanol:dichloromethane (1:8:300) afforded the title compound (E211); MS (ES+) m/e 345 [M+H]$^+$.

Example 212

N-{5-[(3-Cyclobutyl-2,3,4,5-tetrahydro-1H-3-benzazepin-7-yl)oxy]-2-thienyl}acetamide (E212)

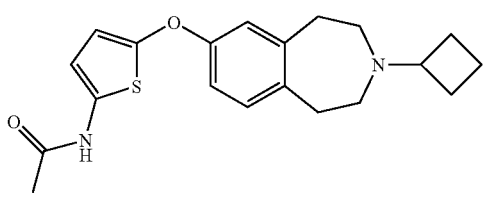

Example 212 (E212) was prepared from 3-cyclobutyl-7-[(5-nitro-2-thienyl)oxy]-2,3,4,5-tetrahydro-1H-3-benzazepine (E211) using an analogous method to that described for Example 210 (E210); MS (ES+) m/e 357 [M+H]$^+$.

Example 213a

3-Cyclobutyl-7-{[6-(methyloxy)-3-pyridinyl]oxy}-2,3,4,5-tetrahydro-1H-3-benzazepine (E213a)

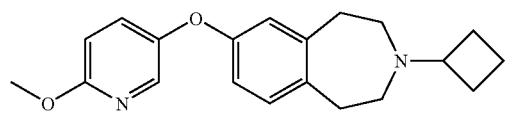

Title compound was prepared from 3-cyclobutyl-2,3,4,5-tetrahydro-1H-benzo[d]azepin-7-ol (E3) and 5-bromo-2-methoxypyridine using the protocol outlined for Example 128 (E128); MS (ES+) m/e 325 [M+H]$^+$.

Example 213

5-[(3-Cyclobutyl-2,3,4,5-tetrahydro-1H-3-benza-zepin-7-yl)oxy]-2(1H)-pyridinone (E213)

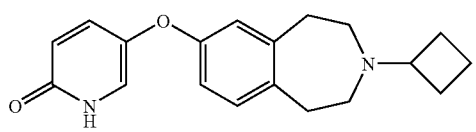

3-Cyclobutyl-7-{[6-(methyloxy)-3-pyridinyl]oxy}-2,3,4,5-tetrahydro-1H-3-benzazepine (E213a) (69 mg, 0.21 mmol) was dissolved in a solution of ethanol saturated with hydrogen chloride (5 ml). The reaction mixture was stirred at reflux for 18 hours, cooled and concentrated in vacuo. Purification of the resulting residue by column chromatography eluting with a mixture of 0.880 ammonia:methanol:dichloromethane (1:9:90) afforded the title compound (E213). MS (ES+) m/e 311 [M+H]$^+$.

Example 214

1-{6-[(3-Cyclobutyl-2,3,4,5-tetrahydro-1H-3-benza-zepin-7-yl)oxy]-3-pyridinyl}ethanone (E214)

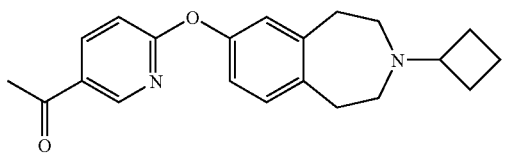

Example 214 (E214) was prepared from 3-cyclobutyl-2,3,4,5-tetrahydro-1H-benzo[d]azepin-7-ol (E3) and 1-(6-chloropyridin-3-yl)ethanone using the method described for Example 100 (E100); MS (ES+) m/e 337 [M+H]$^+$.

Example 215

3-Cyclobutyl-7-{[5-(1H-pyrazol-5-yl)-2-pyridinyl]oxy}-2,3,4,5-tetrahydro-1H-3-benzazepine (E215)

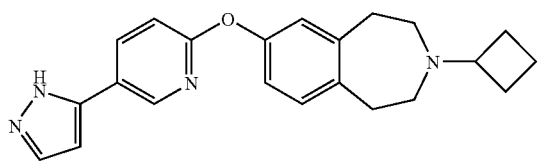

A mixture of (2E)-1-{6-[(3-cyclobutyl-2,3,4,5-tetrahydro-1H-3-benzazepin-7-yl)oxy]-3-pyridinyl}-3-(dimethylamino)-2-propen-1-one (D53) (195 mg, 0.5 mmol) and hydrazine hydrate (0.4 ml) in methanol (3 ml) was heated at reflux for 24 hours. The reaction mixture was cooled and applied to a SCX ion exchange cartridge (Varian bond-elute, 10 g) and washed with methanol and then a mixture of 0.880 ammonia/methanol (1:9). The combined basic fractions were concentrated in vacuo and the resulting residue purified by column chromatography eluting with a mixture of 0.880 ammonia:methanol:dichloromethane (1:9:90) to afford the title compound (E215). MS (ES+) m/e 361 [M+H]$^+$.

Example 216

3-Cyclobutyl-7-{[5-(5-methyl-1,3,4-oxadiazol-2-yl)-2-pyridinyl]oxy}-2,3,4,5-tetrahydro-1H-3-benzazepine (E216)

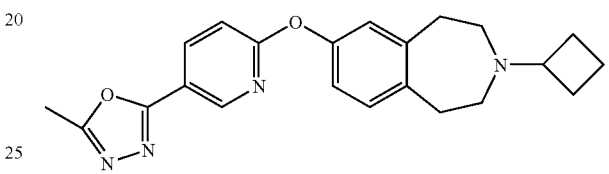

A mixture of triethylorthoacetate (3 ml) and 6-[(3-cyclobutyl-2,3,4,5-tetrahydro-1H-3-benzazepin-7-yl)oxy]-3-pyridinecarbohydrazide (D54) (185 mg, 0.52 mmol) was heated at reflux for 16 hours. The reaction mixture was concentrated and the resulting residue was purified by column chromatography eluting with a mixture of 0.880 ammonia:methanol:dichloromethane (0.1:5:95) to afford the title compound (E216). MS (ES+) m/e 377 [M+H]$^+$.

Example 217

1-{6-[(3-Cyclobutyl-2,3,4,5-tetrahydro-1H-3-benza-zepin-7-yl)oxy]-3-pyridinyl}-2-pyrrolidinone (E217)

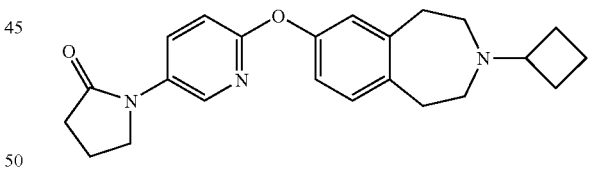

A mixture of 3-cyclobutyl-7-[(5-iodo-2-pyridinyl)oxy]-2,3,4,5-tetrahydro-1H-3-benzazepine (E207) (252 mg, 0.6 mmol), 2-pyrrolidinone (153 mg, 1.8 mmol), potassium carbonate (83 mg, 0.6 mmol), copper powder (126 mg, 1.2 mmol) were heated in a microwave reactor at 150° C. for 1 minute. The reaction mixture was diluted with 2-pyrrolidinone (1 g, 12 mmol) and heated for a further 20 minutes at 200° C. The reaction mixture was cooled and applied to a SCX ion exchange cartridge (Varian bond-elute, 10 g) and washed with methanol and then a mixture of 0.880 ammonia/methanol. The combined basic fractions were concentrated in vacuo and the resulting residue purified by column chromatography eluting with a mixture of 0.880 ammonia:methanol:dichloromethane (1:9:90) to afford the title compound (E217). MS (ES+) m/e 378 [M+H]$^+$.

Example 218

1-{6-[(3-Cyclobutyl-2,3,4,5-tetrahydro-1H-3-benzazepin-7-yl)oxy]-3-pyridinyl}-2-piperidinone (E218)

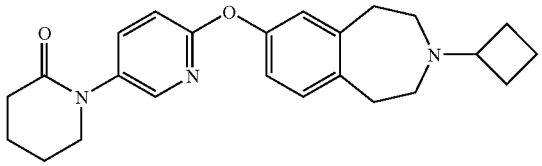

Example 218 (E218) was prepared from 3-cyclobutyl-7-[(5-iodo-2-pyridinyl)oxy]-2,3,4,5-tetrahydro-1H-3-benzazepine (E207) and 2-piperidinone using the method described for Example 217 (E217); MS (ES+) m/e 392 [M+H]$^+$.

Example 219

1-{6-[(3-Cyclobutyl-2,3,4,5-tetrahydro-1H-3-benzazepin-7-yl)oxy]-3-pyridinyl}-2-azetidinone (E219)

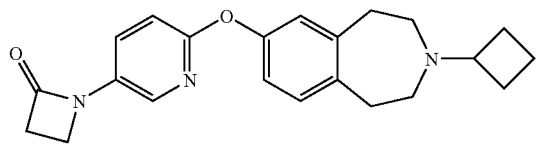

Cesium carbonate (678 mg, 1.04 mmol) was added to a solution of 2-azetidinone (308 mg, 4.3 mmol) in dioxane (1 ml). The mixture was heated in a microwave reactor at 150° C. for 1 minute then a mixture of 3-cyclobutyl-7-[(5-iodo-2-pyridinyl)oxy]-2,3,4,5-tetrahydro-1H-3-benzazepine (E207) (294 mg, 0.7 mmol), trans-1,2-diaminocyclohexane (0.02 ml) and copper (I) iodide (126 mg, 1.2 mmol) were added and the resulting mixture was heated in microwave reactor at 180° C. for 1 hour. The reaction mixture was cooled and applied to a SCX cartridge (Varian bond-elute, 10 g) and washed with methanol and then a mixture of 0.880 ammonia:methanol (1:9). The combined basic fractions were concentrated in vacuo and the resulting residue purified by column chromatography (0.5:2.5:97.5) to afford the title compound (E219). MS (ES+) m/e 364 [M+H]$^+$.

Example 220

3-{6-[(3-Cyclobutyl-2,3,4,5-tetrahydro-1H-3-benzazepin-7-yl)oxy]-3-pyridinyl}-1,3-oxazolidin-2-one (E220)

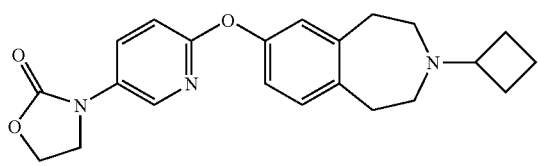

Example 220 (E220) was prepared from 3-cyclobutyl-7-[(5-iodo-2-pyridinyl)oxy]-2,3,4,5-tetrahydro-1H-3-benzazepine (E207) and 1,3-oxazolidin-2-one using the method described for Example 219 (E219); MS (ES+) m/e 380 [M+H]$^+$.

Example 221

3-Cyclobutyl-7-{[5-(1H-pyrazol-1-yl)-2-pyridinyl]oxy}-2,3,4,5-tetrahydro-1H-3-benzazepine (E221)

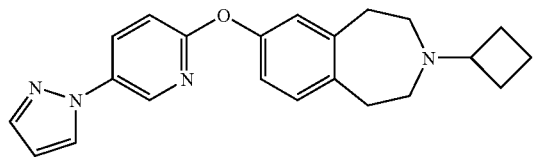

A mixture of 3-cyclobutyl-7-[(5-iodo-2-pyridinyl)oxy]-2,3,4,5-tetrahydro-1H-3-benzazepine (E207) (294 mg, 0.7 mmol), pyrazole (58 mg, 0.84 mmol), cesium carbonate (479 mg, 1.5 mmol), copper (I) iodide (7 mg, 0.04 mmol) and 1,10 phenanthroline (13 mg, 0.07 mmol) in dioxane (2 ml) were heated in a microwave reactor at 180° C. for 20 minutes. The reaction mixture was diluted with ethyl acetate and washed with a saturated solution of ammonium chloride, water, brine and dried (magnesium sulfate). The organic layer was filtered, concentrated in vacuo and the resulting residue was purified by column chromatography eluting with a mixture of 0.880 ammonia:methanol:dichloromethane (0.5:4.5:95) to afford the title compound (E221); MS (ES+) m/e 361 [M+H]$^+$.

Example 222

3-Cyclobutyl-7-{[5-(3,5-dimethyl-4-isoxazolyl)-2-pyridinyl]oxy}-2,3,4,5-tetrahydro-1H-3-benzazepine (E222)

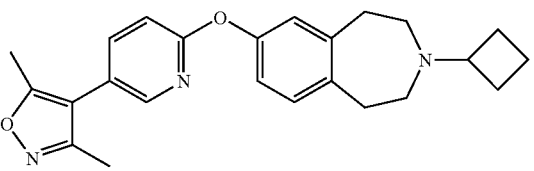

A mixture of 3-cyclobutyl-7-[(5-iodo-2-pyridinyl)oxy]-2,3,4,5-tetrahydro-1H-3-benzazepine (E207) (252 mg, 0.6 mmol), 3,5 dimethyl-4-isoxazoyl boronic acid (168 mg, 1.2 mmol) and tetrakis(triphenylphosphine)palladium(0) in 2M sodium carbonate solution (5 ml) and ethylene glycol dimethyl ether (10 ml) was stirred at reflux for 14 hours. The reaction mixture was diluted with ethyl acetate and washed with a saturated solution of sodium bicarbonate, water, brine and dried (sodium sulfate). The organic layer was filtered, concentrated in vacuo and the resulting residue was purified by column chromatography eluting with a mixture of 0.880 ammonia:methanol:dichloromethane (0.5:4.5:95) to afford the title compound (E222); MS (ES+) m/e 390 [M+H]$^+$.

Example 223

6-[(3-Cyclopentyl-2,3,4,5-tetrahydro-1H-3-benzazepin-7-yl)oxy]-N-methyl-3-pyridinecarboxamide (E223)

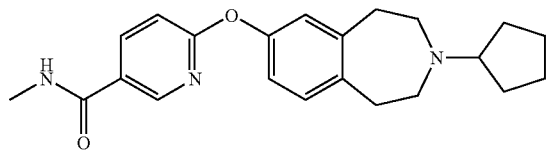

N-Methyl-6-(2,3,4,5-tetrahydro-1H-3-benzazepin-7-yloxy)-3-pyridinecarboxamide (D40) (150 mg, 0.5 mmol) was dissolved in 2.5% acetic acid in methanol (5 ml) and treated dropwise with cyclopentanone (0.09 ml, 1 mmol). The mixture was stirred for 30 minutes and then (polystyrylmethyl)trimethylammonium cyanoborohydride (2.04 mmol/g, 490 mg, 0.1 mmol) was added. The reaction mixture was stirred at room temperature for 14 hours, applied to a SCX cartridge (Varian bond-elute, 10 g) and washed with methanol and then a mixture of 0.880 ammonia/methanol. The combined basic fractions were concentrated in vacuo and the resulting residue purified by column chromatography eluting with a mixture of 0.880 ammonia:methanol:dichloromethane (0.25:2.25:97.5) to afford the title compound (E223). MS (ES+) m/e 366 [M+H]$^+$.

Example 224

N-Methyl-6-{[3-(2-methylcyclopentyl)-2,3,4,5-tetrahydro-1H-3-benzazepin-7-yl]oxy}-3-pyridinecarboxamide (E224)

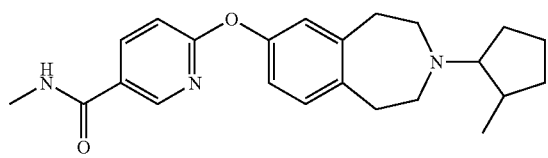

Example 224 (E224) was prepared from N-methyl-6-(2,3,4,5-tetrahydro-1H-3-benzazepin-7-yloxy)-3-pyridinecarboxamide (D40) and 2-methyl cyclopentanone using the method described for Example 223; MS (ES+) m/e 380 [M+H]$^+$.

Example 225

6-[(3-Cyclobutyl-8-iodo-2,3,4,5-tetrahydro-1H-3-benzazepin-7-yl)oxy]-N-methyl-3-pyridinecarboxamide (E225)

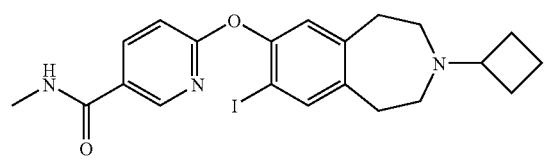

N-Methyl-6-(8-iodo-2,3,4,5-tetrahydro-1H-3-benzazepin-7-yloxy)-3-pyridinecarboxamide (D43) (423 mg, 1.0 mmol) was dissolved in 2.5% acetic acid in methanol (5 ml) and treated dropwise with cyclobutanone (0.11 ml, 1.5 mmol). The mixture was stirred for 30 minutes and then (polystyrylmethyl)trimethylammonium cyanoborohydride (2.0 mmol/g, 1 g, 2 mmol) was added. The reaction mixture was stirred at room temperature for 18 hours, applied to a SCX ion exchange cartridge (Varian bond-elute, 10 g) and washed with methanol and then a mixture of 0.880 ammonia: methanol (1:9). The combined basic fractions were concentrated in vacuo and the resulting residue purified by column chromatography eluting with a mixture of 0.880 ammonia: methanol:dichloromethane (0.5:2.25:97.5) to afford the title compound (E225). MS (ES+) m/e 478 [M+H]$^+$.

Example 226

3-Cyclobutyl-7-iodo-8-[(phenyl methyl)oxy]-2,3,4,5-tetrahydro-1H-3-benzazepine (E226)

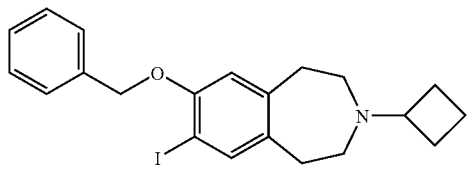

Example 226 (E226) was prepared from 7-iodo-8-[(phenylmethyl)oxy]-2,3,4,5-tetrahydro-1H-3-benzazepine (D45) and cyclobutanone using the method described for Example 225 (E225); MS (ES+) m/e 434 [M+H]$^+$.

Example 227

3-Cyclobutyl-7-{[6-methyl-4-(methyloxy)-2-quinolinyl]oxy}-2,3,4,5-tetrahydro-1H-3-benzazepine (E227)

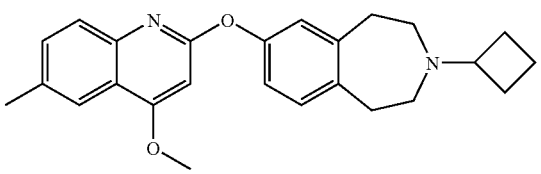

A mixture of 3-cyclobutyl-2,3,4,5-tetrahydro-1H-benzo [d]azepin-7-ol (E3) (58 mg, 0.267 mmol), 2-chloro-6-methyl-4-(methyloxy)quinoline (WO 99/55677) (56 mg, 0.027 mmol) and cesium carbonate (260 mg, 0.801 mmol) in dry DMF (3 ml) was heated at 150° C. for 2×30 mins. (300 W) in a microwave reactor. The cooled reaction mixture was partitioned between ethyl acetate (3×20 ml) and water (30 ml). The combined organic layers were washed with brine (2×30 ml), dried (Na$_2$SO$_4$), filtered and concentrated in vacuo. Purification of the resulting residue by column chromatography on silica gel, eluting with a mixture of 0.880 ammonia:methanol:dichloromethane (0.5:4.5:95) to afford the title compound (E227); MS (ES+) m/e 389 [M+H]$^+$.

Examples 228-230

Examples 228-230 (E228-E230) were prepared from 3-cyclobutyl-2,3,4,5-tetrahydro-1H-benzo[d]azepin-7-ol (E3) and the appropriate aromatic halide indicated in the table using an analogous method to that described for Example 227:

| Example | Aromatic chloride | LC/MS (M + H$^+$) |
|---|---|---|
| 3-Cyclobutyl-7-{[4-(methyloxy)-1,7-naphthyridin-2-yl]oxy}-2,3,4,5-tetrahydro-1H-3-benzazepine (E228) | 2-Chloro-4-(methyloxy)-1,7-naphthyridine | 376 |
| 3-Cyclobutyl-7-(1,5-naphthyridin-2-yloxy)-2,3,4,5-tetrahydro-1H-3-benzazepine (E229) | 2-Bromo-1,5-naphthyridine (J. W. Henk, J.Org.Chem., 1982, 47(9), 1673-1677) | 346 |
| N-{7-[(3-Cyclobutyl-2,3,4,5-tetrahydro-1H-3-benzazepin-7-yl)oxy]-6-methyl-1,8-naphthyridin-2-yl}acetamide (E230) | N-(7-Chloro-6-methyl-1,8-naphthyridin-2-yl)acetamide (S. Carboni, Gazz. Chim. Ital., 1966, 96(11), 1456-1469) | 417 |

Example 231

Dimethyl 6-[(3-cyclobutyl-2,3,4,5-tetrahydro-1H-3-benzazepin-7-yl)oxy]-2,3-pyridinedicarboxylate (E231)

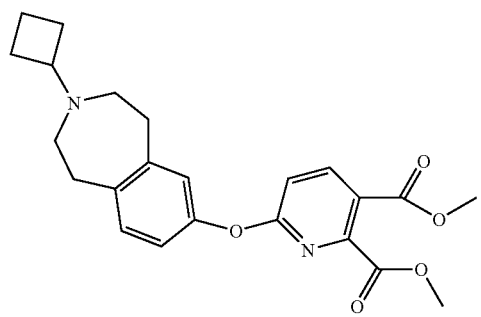

A mixture of 3-cyclobutyl-2,3,4,5-tetrahydro-1H-benzo[d]azepin-7-ol (E3) (1.5 g), dimethyl 6-chloro-2,3-pyridinedicarboxylate (1.58 g; Kenji Niiyama et al. Bioorg. Med. Chem. Lett. 12, 21, 2002, 3041-3054) and cesium carbonate (4.4 g) in dry DMF (30 ml) was heated at 80° C. for 3 h. The cooled mixture was partitioned between water (20 ml) and ethyl acetate (3×100 ml), the combined organic extracts were washed with brine (2×100 ml) and dried (Na$_2$SO$_4$). The solvent was evaporated to give an oil which was purified by column chromatography eluting with a mixture of 0.880 ammonia:methanol:dichloromethane (0.5:4.5:95) to afford the title compound (E231); MS (ES+) m/e 411 [M+H]$^+$.

Example 232

Disodium 6-[(3-cyclobutyl-2,3,4,5-tetrahydro-1H-3-benzazepin-7-yl)oxy]-2,3-pyridinedicarboxylate (E232)

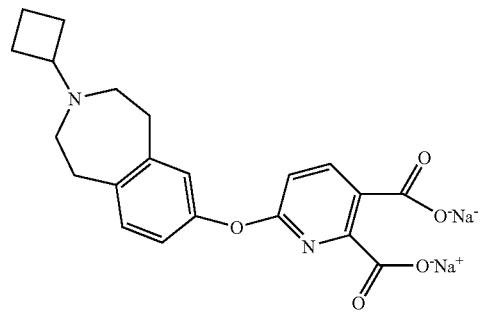

Sodium hydroxide (0.66 g) in water (3 ml) was added to a solution of dimethyl 6-[(3-cyclobutyl-2,3,4,5-tetrahydro-1H-3-benzazepin-7-yl)oxy]-2,3-pyridinedicarboxylate (E231) (1.69 g, 4.12 mmol) in ethanol (20 ml) at room temperature. The mixture was vigorously stirred at room temperature for 4 h and the resulting precipitate filtered off to give the title compound as a colourless solid (E232); MS (ES+) m/e 383 [M+H]$^+$.

Example 233

2-[(3-Cyclobutyl-2,3,4,5-tetrahydro-1H-3-benzazepin-7-yl)oxy]-5H-pyrrolo[3,4-b]pyridine-5,7(6H)-dione (E233)

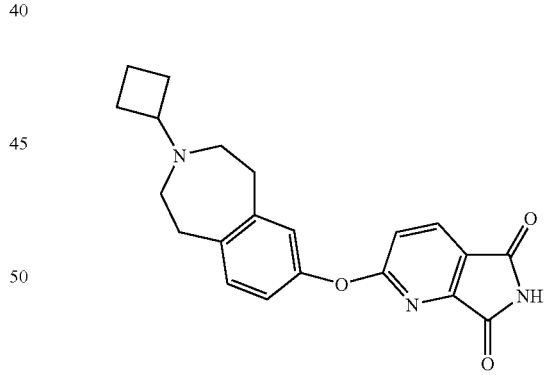

A suspension of disodium 6-[(3-cyclobutyl-2,3,4,5-tetrahydro-1H-3-benzazepin-7-yl)oxy]-2,3-pyridinedicarboxylate (E232) (0.2 g, 0.52 mmol) in acetic anhydride (2 ml) was stirred and heated at 120° C. for 20 mins. The cooled mixture was concentrated in vacuo and acetamide (0.1 g) added to the residue and the mixture heated at 160° C. for 0.5 h. The cooled mixture was then purified by column chromatography eluting with a mixture of 0.880 ammonia:methanol:dichloromethane (0.5:4.5:95). The resulting pale yellow solid was triturated with ether (5 ml) and filtered to give the title compound (E233); MS (ES+) m/e 364 [M+H]$^+$.

Example 234

2-[(3-Cyclobutyl-2,3,4,5-tetrahydro-1H-3-benzazepin-7-yl)oxy]-7-hydroxy-6,7-dihydro-5H-pyrrolo[3,4-b]pyridin-5-one (E234)

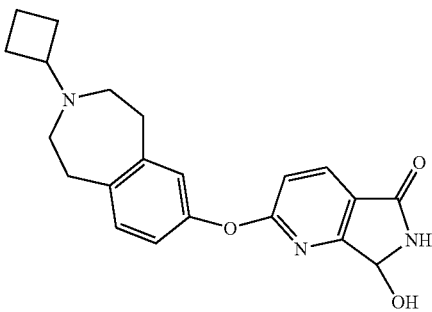

Magnesium perchlorate (0.89 g) was added to a solution of 2-[(3-cyclobutyl-2,3,4,5-tetrahydro-1H-3-benzazepin-7-yl)oxy]-5H-pyrrolo[3,4-b]pyridine-5,7(6H)-dione (E233) (0.72 g, 1.98 mmol) in a mixture of chloroform:methanol (1:1; 20 ml) at 0° C. under argon. Sodium borohydride (113 mg) was added and the mixture stirred at for 0.5 h. The mixture was adjusted to pH 2 with HCl (2M), stirred for an additional 0.5 h, then taken to pH 11 with sodium hydroxide (2N). The mixture was then extracted with dichloromethane and the combined organic extracts dried ($Na_2SO_4$) and evaporated. The residue was purified by column chromatography eluting with a mixture of 0.880 ammonia:methanol:dichloromethane (1:9:90) to afford the title compound (E234); MS (ES+) m/e 366 [M+H]$^+$.

Example 235

2-[(3-Cyclobutyl-2,3,4,5-tetrahydro-1H-3-benzazepin-7-yl)oxy]-6,7-dihydro-5H-pyrrolo[3,4-b]pyridin-5-one (E235)

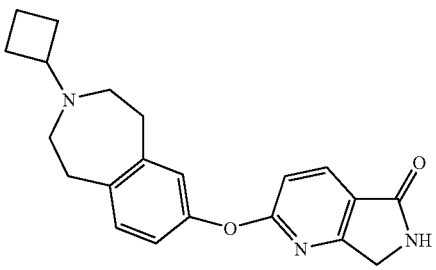

A mixture of 2-[(3-cyclobutyl-2,3,4,5-tetrahydro-1H-3-benzazepin-7-yl)oxy]-7-hydroxy-6,7-dihydro-5H-pyrrolo[3,4-b]pyridin-5-one (E234) (90 mg, 0.25 mmol) and triethylsilane (0.1 ml) in trifluoroacetic acid (0.1 ml) was vigorously stirred at room temperature for 1 h. The mixture was concentrated in vacuo and the residue purified by column chromatography eluting with a mixture of 0.880 ammonia:methanol:dichloromethane (1:9:90); MS (ES+) m/e 350 [M+H]$^+$.

Example 236

6-[(3-Cyclobutyl-2,3,4,5-tetrahydro-1H-3-benzazepin-7-yl)oxy]-3-pyridinamine (E236)

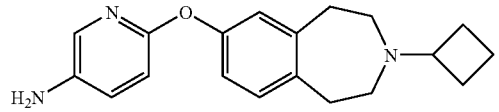

3-Cyclobutyl-7-[(5-nitro-2-pyridinyl)oxy]-2,3,4,5-tetrahydro-1H-3-benzazepine (E208) (100 mg, 0.29 mmol) was dissolved in ethanol (10 ml). Palladium (20 mg, 10% on charcoal paste) was added and the reaction mixture was stirred at room temperature under hydrogen (1 atmosphere) for 12 hours. The reaction mixture was filtered through celite and the filtrate concentrated in vacuo to afford the title compound (E236); MS (ES+) m/e 310 [M+H]$^+$.

Example 237

Morpholine-4-carboxylic acid[6-(3-cyclobutyl-2,3,4,5-tetrahydro-1H-benzo[d]azepin-7-yloxy-pyridin-3-yl-amide (E237)

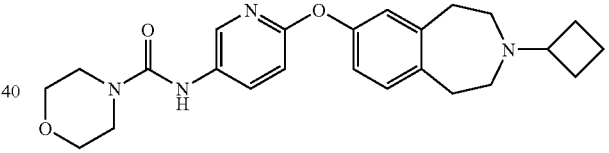

Morpholine-4-carbonyl chloride (0.15 ml, 1.38 mmol) was added to a stirred solution of 6-[(3-cyclobutyl-2,3,4,5-tetrahydro-1H-3-benzazepin-7-yl)oxy]-3-pyridinamine (E236) (77 mg, 0.25 mmol) and triethylamine (0.04 ml, 0.30 mmol) in dichloromethane (5 ml) at 0° C. The reaction mixture was warmed to room temperature and allowed to stir for 24 hours. The reaction mixture was applied to a SCX ion exchange cartridge (Varian bond-elute, 5 g) and washed with methanol and then a mixture of 0.880 ammonia:methanol (1:9). The combined basic fractions were concentrated in vacuo and the resulting residue purified by column chromatography eluting with a mixture of 0.880 ammonia:methanol:dichloromethane (0.5:4.5:95) to afford the title compound; MS (ES+) m/e 423 [M+H]$^+$.

Examples 238-240

Examples 238-240 were prepared from 6-[(3-cyclobutyl-2,3,4,5-tetrahydro-1H-3-benzazepin-7-yl)oxy]-3-pyridinamine (E236) and the appropriate carbonyl chloride or acid chloride indicated in the table using an analogous method to that described for Example 237 (E237):

| Example | Carbonyl Chloride/Acid Chloride | LC/MS (M + H⁺) |
|---|---|---|
| Piperidine-1-carboxylic acid[6-(3-cyclobutyl-2,3,4,5-tetrahydro-1H-benzo[d]azepin-7-yloxy-pyridin-3-yl]-amide (E238) | Piperidine-1-carbonyl chloride | 421 |
| Pyrrolidine-1-carboxylic acid[6-(3-cyclobutyl-2,3,4,5-tetrahydro-1H-benzo[d]azepin-7-yloxy)-pyridin-3-yl]-amide (E239) | Pyrrolidine-1-carbonyl chloride | 407 |
| N-[6-(3-Cyclobutyl-2,3,4,5-tetrahydro-1H-benzo[d]azepin-7-yloxy)-pyridin-3-yl] isobutyramide (E240) | Isobutyryl chloride | 380 |

Example 241

Tetrahydro-pyran-4-carboxylic acid [6-(3-cyclobutyl-2,3,4,5-tetrahydro-1H-benzo[d]azepin-7-yloxy)-pyridin-3-yl]-amide (E241)

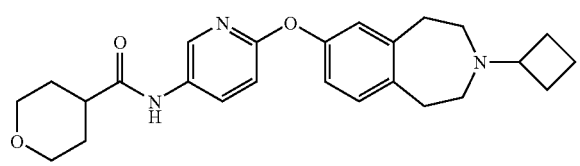

Tetrahydro-pyran-4-carboxylic acid (252 mg, 1.94 mmol), 1-hydroxy benzotriazole hydrate (262 mg, 1.94 mmol) and N-cyclohexylcarbodiimide N'-methyl polystyrene (1.7 mmol/g, 2.3 g, 3.88 mmol) were stirred at room temperature in dichloromethane (10 ml) for 15 minutes. 6-[(3-Cyclobutyl-2,3,4,5-tetrahydro-1H-3-benzazepin-7-yl)oxy]-3-pyridinamine (E236) (300 mg, 0.97 mmol) was added and stirring continued for 16 hours. The reaction mixture was applied to a SCX ion exchange cartridge (Varian bond-elute, 5 g) and washed with methanol and then a mixture of 0.880 ammonia/methanol. The combined basic fractions were concentrated in vacuo and the resulting residue was purified by column chromatography eluting with a mixture of 0.880 ammonia:methanol:dichloromethane (0.5:4.5:95) to afford the title product (E241); MS (ES+) m/e 422 [M+H]⁺.

Example 242

3-Cyclobutyl-7-[5-(4,6-dimethoxy-pyrimidin-2-yl)-pyridin-2-yloxy]-2,3,4,5-tetrahydro-1H-benzo[d]azepine (E242)

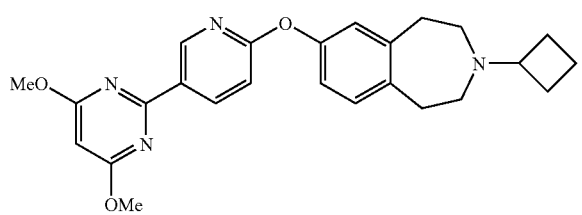

3-Cyclobutyl-2,3,4,5-tetrahydro-1H-benzo[d]azepin-7-ol (E3) (125 mg, 0.58 mmol), 2-(6-chloro-pyridin-3-yl)-4,6-dimethoxy-pyrimidine (145 mg, 0.58 mmol), calcium carbonate (720 mg, 2.2 mmol) and dimethylformamide (4 ml) were heated in a microwave reactor at 180° C. for 900 seconds at 300 W. The mixture was diluted with ethyl acetate, washed with water, then brine and dried over sodium sulphate. The residue was purified by column chromatography eluting with a mixture of 0.880 ammonia:methanol:dichloromethane (0.2:1.8:98) to afford the title product. MS (ES+) m/e 433 [M+H]⁺.

Examples 243-249

Examples 243-249 (E243-E249) were prepared from 3-cyclobutyl-2,3,4,5-tetrahydro-1H-benzo[d]azepin-7-ol (E3) and the aryl chloride indicated in the table using an analogous method to that described for Example 242 (E242).

| Example | Aryl Chloride | LC/MS (M + H⁺) |
|---|---|---|
| 3-Cyclobutyl-7-[5-(4-methanesulfonyl-phenyl)-pyrazine-2-yloxy)-2,3,4,5-tetrahydro-1H-benzo[d]azepine (E243) | 2-(6-Chloro-pyridin-3-yl)-5-methanesulfonyl-pyrazine | 450 |
| N-{4-[5-(3-Cyclobutyl-2,3,4,5-tetrahydro-1H-benzo[d]azepin-7-yloxy)-pyrazin-2-yl]-phenyl}-acetamide (E244) | N-[4-(5-Chloro-pyrazin-2-yl)-phenyl]-acetamide | 429 |
| 3-Cyclobutyl-7-(3,5-dimethyl-pyridin-2-yloxy)-2,3,4,5-tetrahydro-1H-benzo[d]azepine (E245) | 2-Chloro-3,5-dimethyl-pyridine | 323 |
| 3-Cyclobutyl-7-[5-(morpholine-4-sulfonyl)-pyridin-2-yloxy]-2,3,4,5-tetrahydro-1H-benzo[d]azepine (E246) | 4-(6-Chloro-pyridine-3-sulfonyl)-morpholine | 444 |
| 3-Cyclobutyl-7-(2-methyl-furo[2,3-c]pyridin-7-yloxy)-2,3,4,5-tetrahydro-1H-benzo[d]azepine (E247) | 7-Chloro-2-methyl-furo[2,3-c]pyridine | 349 |
| 2-(3-Cyclobutyl-2,3,4,5-tetrahydro-1H-benzo[d]azepin-7-yloxy)-4-ethoxy-nicotinonitrile (E248) | 2-Chloro-4-ethoxy-nicotinonitrile | 364 |
| 6-(3-Cyclobutyl-2,3,4,5-tetrahydro-11H-benzo[d]azepin-7-yloxy)-2-methyl-nicotinonitrile (E249) | 6-Chloro-2-methyl-nicotinonitrile | 334 |

Example 250

1-{6-[(3-Cyclobutyl-2,3,4,5-tetrahydro-1H-3-benzazepin-7-yl)oxy]-3-pyridinyl}-5-methyl-2-pyrrolidinone (E250)

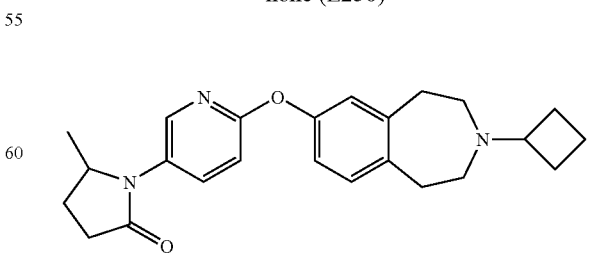

3-Cyclobutyl-7-[(5-iodo-2-pyridinyl)oxy]-2,3,4,5-tetrahydro-1H-3-benzazepine (E207) (294 mg, 0.7 mmol) 1,10 phenanthroline (38 mg, 0.2 mmol), 5-methyl-2-pyrrolidinone (139 mg 1.4 mmol) were dissolved in dioxane (2 ml). Copper (I) Iodide (39 mg, 0.2 mmol) and caesium carbonate (479 mg, 1.5 mmol) were added and the mixture heated in a microwave reactor at 175° C. for 15 minutes. The mixture was cooled and filtered through celite, washing through with dichloromethane. The filtrate was concentrated in vacuo and the crude material purified by column chromatography, eluting with dichloromethane through to a mixture of 0.880 ammonia:methanol:dichloromethane (1:9:90) to afford the title compound (137 mg); MS (ES+) m/e 392 [M+H]$^+$.

Example 251

1-{6-[(3-Cyclobutyl-2,3,4,5-tetrahydro-1H-3-benzazepin-7-yl)oxy]-3-pyridinyl}-3-methyl-2-imidazolidine (E251)

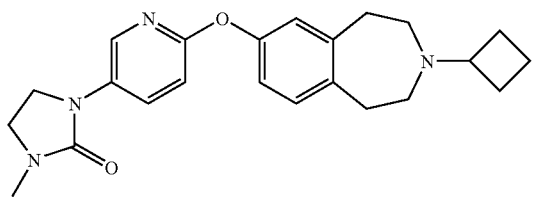

3-Cyclobutyl-7-[(5-iodo-2-pyridinyl)oxy]-2,3,4,5-tetrahydro-1H-3-benzazepine (E207) (294 mg 0.7 mmol), 1-methyl-2-imidazolidinone (90 mg, 0.9 mmol) caesium carbonate (364 mg 1.1 mmol) xantphos (12 mg, 0.02 mmol), were suspended in toluene (10 ml). tris(dibenzylideneacetone)dipalladium(0) (6 mg, 0.007 mmol) was added and the mixture heated at reflux overnight. The reaction was then applied directly on to SCX ion exchange cartridge (Varian, 5 g) and washed with methanol then a mixture of 0.880 ammonia:methanol (1:9). The basic fractions were reduced and the crude material purified by automated reverse phase chromatography to afford the title product (104 mg); MS (ES+) m/e 393 [M+H]$^+$.

Example 252

(4R)-1-{6-[(3-Cyclobutyl-2,3,4,5-tetrahydro-1H-3-benzazepin-7-yl)oxy]-3-pyridinyl}-4-hydroxy-2-pyrrolidinone (E252)

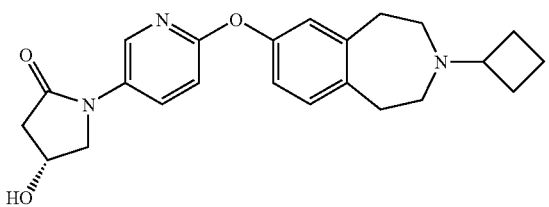

Example 252 (E252) was prepared from 3-cyclobutyl-7-[(5-iodo-2-pyridinyl)oxy]-2,3,4,5-tetrahydro-1H-3-benzazepine (E207) and (4R)-4-{[(1,1-dimethylethyl)(dimethyl)silyl]oxy}-2-pyrrolidinone (Tetrahedron, 2000, 56(39), 7705-7713) using the method described in E251; MS (ES+) m/e 394 [M+H]$^+$.

Example 253

N-Methyl-6-{[3-(3-methylcyclopentyl)-2,3,4,5-tetrahydro-1H-3-benzazepin-7-yl]oxy}-3-pyridinecarboxamide (E253)

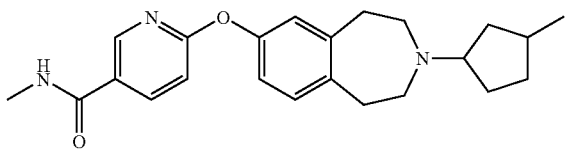

Example 253 (E253) was prepared from n-methyl-6-(2,3,4,5-tetrahydro-1H-3-benzazepin-7-yloxy)-3-pyridinecarboxamide (D40) and 3-methyl cyclopentanone using the method described for Example 223; MS (ES+) m/e 380 [M+H]$^+$.

Example 254

5-[(3-Cyclopentyl-2,3,4,5-tetrahydro-1H-3-benzazepin-7-yl)oxy]-N-methyl-2-pyrazinecarboxamide (E254)

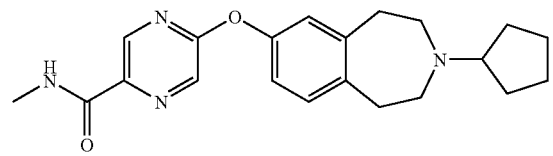

Example 254 (E254) was prepared from n-methyl-5-(2,3,4,5-tetrahydro-1H-3-benzazepin-7-yloxy)-2-pyrazinecarboxamide (D49) and cyclopentanone using the method described for Example 223; MS (ES+) m/e 367 [M+H]$^+$.

Example 255

N-Methyl-5-{[3-(3-methylcyclopentyl)-2,3,4,5-tetrahydro-1H-3-benzazepin-7-yl]oxy}-2-pyrazinecarboxamide (E255)

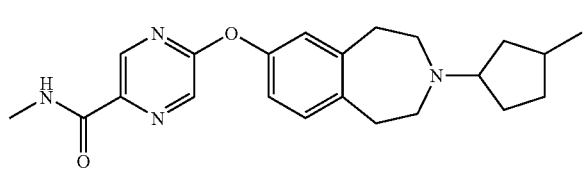

Example 255 (E255) was prepared from N-methyl-5-(2,3,4,5-tetrahydro-1H-3-benzazepin-7-yloxy)-2-pyrazinecarboxamide (D49) and 3-methyl cyclopentanone using the method described for Example 223; MS (ES+) m/e 381 [M+H]+.

Example 256

1-{3-[(3-Cyclobutyl-2,3,4,5-tetrahydro-1H-3-benza-zepin-7-yl)oxy]-2-pyrazinyl}-2-pyrrolidinone (E256)

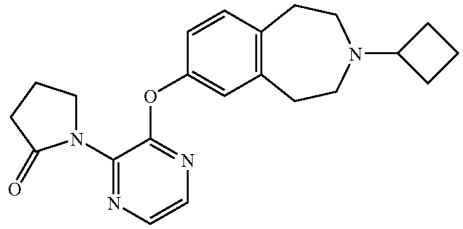

3-Cyclobutyl-2,3,4,5-tetrahydro-1H-benzo[d]azepin-7-ol (E3) (103 mg, 0.47 mmol) was dissolved in dry dimethylformamide (3 ml), cooled to 0° C. and treated with sodium hydride (60% in mineral oil, 20 mg, 0.49 mmol). The mixture was allowed to warm to room temperature over 40 minutes. A solution of 1-(3-chloro-2-pyrazinyl)-2-pyrrolidinone (D46) (103 mg, 0.52 mmol) in dry dimethylformamide (1 ml) was added and the mixture stirred at room temperature for 2 hours and heated at 80° C. for 2.5 hours. The mixture was allowed to cool to room temperature and applied to a SCX column and washed with methanol then a mixture of 0.880 ammonia/methanol (1:9). The basic fractions were combined and concentrated in vacuo and resulting residue was purified by column chromatography eluting with a mixture of 0.880 ammonia:methanol:dichloromethane (0.2:1.8:98) to afford the title compound (86 mg); MS (ES+) m/e 379 [M+H]+.

Example 257

7-[(5-Chloro-2-pyrazinyl)oxy]-3-cyclobutyl-2,3,4,5-tetrahydro-1H-3-benzazepine (E257)

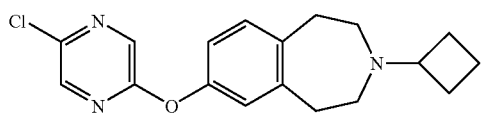

3-Cyclobutyl-2,3,4,5-tetrahydro-1H-benzo[d]azepin-7-ol (E3) (184 mg, 0.85 mmol) was dissolved in dry dimethylformamide (3 ml), cooled to 0° C. and treated with sodium hydride (60% in mineral oil, 36 mg, 0.89 mmol). The mixture was allowed to warm to room temperature over 30 minutes. A solution of 2,5-dichloropyrazine (D47) (139 mg, 0.94 mmol) in dry dimethylformamide (1 ml) was added and the mixture stirred at room temperature for 5 hours. The mixture was applied to a SCX column and washed with methanol then a mixture of 0.880 ammonia/methanol (1:9). The basic fractions were combined and concentrated in vacuo to afford the title compound (268 mg); MS (ES+) m/e 330 [M+H]+.

Example 258

1-{5-[(3-Cyclobutyl-2,3,4,5-tetrahydro-1H-3-benza-zepin-7-yl)oxy]-2-pyrazinyl}-2-pyrrolidinone (E258)

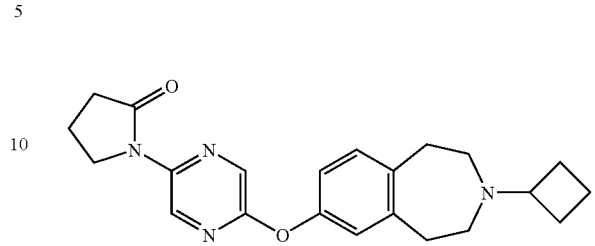

7-[(5-Chloro-2-pyrazinyl)oxy]-3-cyclobutyl-2,3,4,5-tetrahydro-1H-3-benzazepine (E257) (132 mg, 0.40 mmol), pyrrolidinone (0.06 ml, 0.80 mmol), potassium carbonate (200 mg, 1.45 mmol), copper (I) iodide (23 mg, 0.12 mmol) and N,N'-dimethylethylenediamine (0.01 ml, 0.12 mmol) were added together in dry dioxane (3 ml) and heated in a microwave reactor at 175° C. for 30 minutes. The mixture was diluted with methanol and applied to a SCX column and washed with methanol then a mixture of 0.880 ammonia/methanol (1:9). The basic fractions were combined and concentrated in vacuo and the resulting residue was purified by column chromatography eluting with a mixture of 0.880 ammonia:methanol:dichloromethane (0.2:1.8:98) to afford the title compound (64 mg); MS (ES+) m/e 379 [M+H]+.

Example 259

7-[(5-Bromo-2-pyrazinyl)oxy]-3-cyclobutyl-2,3,4,5-tetrahydro-1H-3-benzazepine (E259)

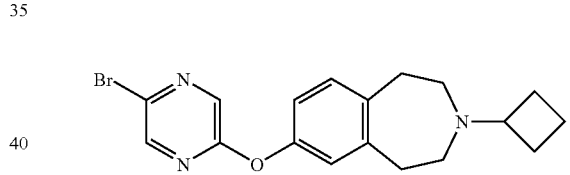

The title compound was prepared from 3-Cyclobutyl-2,3,4,5-tetrahydro-1H-benzo[d]azepin-7-ol (E3) and 2,5-dibromopyrazine (D48) using the method of Example 257 (E257); MS (ES+) m/e 375 [M+H]+.

Example 260

3-{5-[(3-Cyclobutyl-2,3,4,5-tetrahydro-1H-3-benza-zepin-7-yl)oxy]-2-pyrazinyl}-1,3-oxazolidin-2-one (E260)

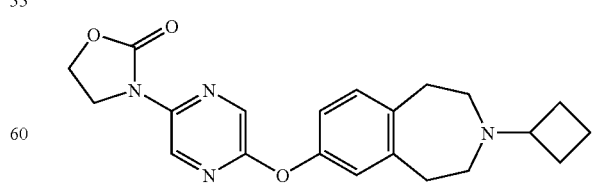

The title compound was prepared from 7-[(5-bromo-2-pyrazinyl)oxy]-3-cyclobutyl-2,3,4,5-tetrahydro-1H-3-benzazepine (E259) and oxazolidinone using the method of Example 258 (E258); MS (ES+) m/e 381 [M+H]+.

Example 261

3-Cyclobutyl-7-[5-(1,1-dioxo-2-isothiazolidin-2-yl)-pyridin-2-yloxy]-2,3,4,5-tetrahydro-1H-3-benzazepine (E261)

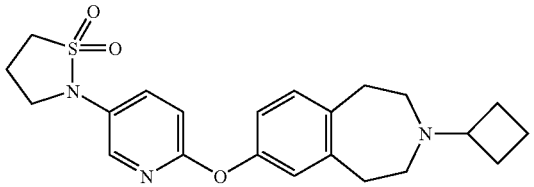

3-Cyclobutyl-7-[(5-iodo-2-pyridinyl)oxy]-2,3,4,5-tetrahydro-1H-3-benzazepine (E207) (200 mg, 0.48 mmol), isothiazolidine 1,1-dioxide (116 mg, 0.96 mmol), (Evans, Brian J.; Takahashi Doi, Joyce; Musker, W. Kenneth; J. Org. Chem.; 55; 9; 1990; 2580-2586) potassium carbonate (238 mg, 1.73 mmol), copper (I) iodide (27 mg, 0.14 mmol) and N,N-dimethylethylenediamine (0.02 ml, 0.14 mmol) were added together in dry dioxane (3 ml) and heated in a microwave reactor at 140° C. for 20 minutes. The mixture was diluted with methanol and applied to a SCX column eluting with methanol and then a mixture of 0.880 ammonia/methanol (1:9). The basic fractions were combined and concentrated in vacuo. The resulting residue was purified by column chromatography eluting with a mixture of 0.880 ammonia:methanol:dichloromethane (0.5:4.5:95) to afford the title compound (145 mg); MS (ES+) m/e 414 [M+H]+.

Example 262

1-{6-[(3-Cyclobutyl-2,3,4,5-tetrahydro-1H-3-benzazepin-7-yl)oxy]-3-pyridinyl}-2-imidazolidinone (E262)

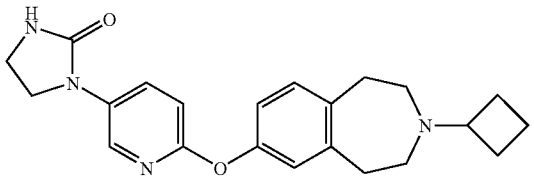

The title compound was prepared from 3-cyclobutyl-7-[(5-iodo-2-pyridinyl)oxy]-2,3,4,5-tetrahydro-1H-3-benzazepine (E207) and 2-imidazolidinone using the method of Example 261; MS (ES+) m/e 379 [M+H]+.

Example 263

5-[(3-Cyclobutyl-2,3,4,5-tetrahydro-1H-3-benzazepin-7-yl)oxy]-2-pyrazinecarboxamide (E263)

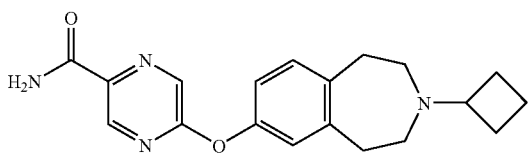

5-[(3-Cyclobutyl-2,3,4,5-tetrahydro-1H-3-benzazepin-7-yl)oxy]-2-pyrazinecarboxylic acid (E123a) (168 mg, 0.47 mmol) was dissolved in dry dimethylformamide (5 ml), treated with 1,1'-carbonyldiimidazole (230 mg, 1.42 mmol) and the resulting mixture stirred at room temperature for 1.5 hours. The mixture was treated with 0.880 ammonia (0.14 ml, 2.84 mmol) and stirred for 4 hours. The reaction mixture was concentrated in vacuo and the resulting residue purified by column chromatography eluting with a mixture of (0.5:4.5:95) to afford the title compound; MS (ES+) m/e 339 [M+H]+.

Example 264

4-[(3-Cyclobutyl-2,3,4,5-tetrahydro-1H-3-benzazepin-7-yl)oxy]-N-methyl-3-(methyloxy)benzamide (E264)

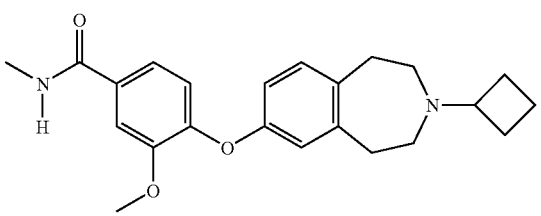

Step 1: 1,1-Dimethylethyl 7-(4,4,5,5-tetramethyl-1,3,2-dioxaborolan-2-yl)-1,2,4,5-tetrahydro-3H-3-benzazepine-3-carboxylate 1,1-Dimethylethyl 7-{[(trifluoromethyl)sulfonyl]oxy}-1,2,4,5-tetrahydro-3H-3-benzazepine-3-carboxylate (2.0 g, 5.06 mmol) (Bioorg. Med. Chem. Lett.; 10; 22; 2000; 2553-2556), bis(pinacolato)diboron (1.41 g, 5.57 mmol), 1,1'-bis(diphenylphosphino)ferrocenedichloropalladium (II) complex (0.22 g, 0.30 mmol), 1,1'-bis(diphenylphosphino) ferrocene (0.17 g, 0.30 mmol) and potassium acetate (1.49 g, 15.2 mmol) were added together in dry dioxane and the resulting mixture heated at 80° C. for 3 hours. The mixture was allowed to cool to room temperature, diluted with ethyl acetate and washed with water and brine. The organic portion was dried under magnesium sulfate and evaporated in vacuo. The resulting residue was purified by column chromatography eluting with a mixture of ethyl acetate:pentane (1:9) to afford the title compound (1.60 g); MS (ES+) m/e 274 [(M+H)—CO$_2^t$Bu]+.

Step 2: (3-{[(1,1-Dimethylethyl)oxy]carbonyl}-2,3,4,5-tetrahydro-1H-3-benzazepin-7-yl)boronic acid 1,1-Dimethylethyl 7-(4,4,5,5-tetramethyl-1,3,2-dioxaborolan-2-yl)-1,2,4,5-tetrahydro-3H-3-benzazepine-3-carboxylate (E264, Step 1) (1.60 g, 4.29 mmol) was dissolved in acetone (25 ml), treated with sodium periodate (2.75 g, 12.9 mmol), ammonium acetate (0.73 g, 9.44 mmol) and water (25 ml) and the resulting mixture was stirred for 18 hours at room temperature. The acetone was removed by evaporation in vacuo and the remaining water layer was extracted with ethyl acetate and dichloromethane. The organic layers were combined, dried under magnesium sulfate and evaporated in vacuo to give the title compound (1.06 g); MS (ES+) m/e 192 [(M+H)—CO$_2^t$Bu]+.

Step 3: 1,1-Dimethylethyl 7-({2-(methyloxy)-4-[(methyloxy)carbonyl]phenyl}oxy)-1,2,4,5-tetrahydro-3H-3-benzazepine-3-carboxylate (3-{[(1,1-Dimethylethyl)oxy]carbonyl}-2,3,4,5-tetrahydro-1H-3-benzazepin-7-yl)boronic acid (E264, Step 2) (500 mg, 1.72 mmol) was dissolved in dry dichloromethane (15 ml) and treated sequentially with methyl vanillate (313 mg, 1.72 mmol), molecular sieves (4A, 1.0 g), copper acetate (467 mg, 2.58 mmol) and triethylamine (1.20 ml, 8.60 mmol) and the resulting mixture was stirred at room temperature for 18 hours. The mixture was diluted with dichloromethane, filtered through celite and evaporated in vacuo. The residue was dissolved in ethyl acetate and washed with saturated sodium bicarbonate solution. The organic portion was dried under magnesium sulfate and evaporated in vacuo. The resulting residue was purified by column chromatography eluting with a mixture of (0.1:9.9) to afford the title compound (240 mg). MS (ES+) m/e 328 [(M+H)—CO$_2^t$Bu]$^+$.

Step 4: 4-[(3-{[(1,1-Dimethylethyl)oxy]carbonyl}-2,3,4,5-tetrahydro-1H-3-benzazepin-7-yl)oxy]-3-(methyloxy)benzoic acid 1,1-Dimethylethyl 7-({2-(methyloxy)-4-[(methyloxy)carbonyl]phenyl}oxy)-1,2,4,5-tetrahydro-3H-3-benzazepine-3-carboxylate (E264, Step 3) (240 mg, 0.56 mmol) was dissolved in ethanol (2 ml), treated with 2M sodium hydroxide (1 ml) and the resulting mixture was stirred for 1.5 hours. The mixture was acidified with 2M hydrochloric acid and extracted with ethyl acetate. The ethyl acetate layers were combined, dried under magnesium sulfate and evaporated in vacuo to afford the title compound (0.15 g); MS (ES+) m/e 314 [(M+H)—CO$_2^t$Bu]$^+$.

Step 5: 1,1-Dimethylethyl 7-{[4-[(methylamino)carbonyl]-2-(methyloxy)phenyl]oxy}-1,2,4,5-tetrahydro-3H-3-benzazepine-3-carboxylate 4-[(3-{[(1,1-Dimethylethyl)oxy]carbonyl}-2,3,4,5-tetrahydro-1H-3-benzazepin-7-yl)oxy]-3-(methyloxy)benzoic acid (E264, Step 4) (145 mg, 0.35 mmol) was dissolved in dry dimethylformamide (5 ml), treated with 1,1'-carbonyldiimidazole (85 mg, 0.53 mmol) and the resulting mixture stirred at room temperature for 3 hours. The mixture was treated with methylamine (0.53 ml, 1.05 mmol, 2M in THF) and stirred for 4 hours. The reaction mixture was concentrated in vacuo and the resulting residue purified by column chromatography (1:1 ethyl acetate:pentane) to afford the title compound (0.10 g); MS (ES+) m/e 327 [(M+H)—CO$_2^t$Bu]$^+$.

Step 6: N-Methyl-3-(methyloxy)-4-(2,3,4,5-tetrahydro-1H-3-benzazepin-7-yloxy)benzamide 1,1-Dimethylethyl 7-{[4-[(methylamino)carbonyl]-2-(methyloxy)phenyl]oxy}-1,2,4,5-tetrahydro-3H-3-benzazepine-3-carboxylate (E264, Step 5) (100 mg, 0.23 mmol) was dissolved in dry dichloromethane (2 ml), treated with trifluoroacetic acid (1 ml) and the resulting mixture was stirred at room temperature for 2 hours. The solvent was removed in vacuo and the residue dissolved in methanol and applied to a SCX column eluting with methanol and then a mixture of 0.880 ammonia:methanol (1:9). The basic fractions were combined and concentrated in vacuo to afford the title compound (78 mg); MS (ES+) m/e 327 [M+H]$^+$.

Step 7: 4-[(3-Cyclobutyl-2,3,4,5-tetrahydro-1H-3-benzazepin-7-yl)oxy]-N-methyl-3-(methyloxy)benzamide N-Methyl-3-(methyloxy)-4-(2,3,4,5-tetrahydro-1H-3-benzazepin-7-yloxy)benzamide (E264, Step 6) (78 mg, 0.24 mmol) was dissolved in dry dichloromethane (5 ml), treated with cyclobutanone (0.04 ml, 0.48 mmol) and acetic acid (1 drop) and the resulting mixture stirred for 15 minutes. Sodium triacetoxyborohydride (102 mg, 0.48 mmol) was added and the mixture stirred for 30 minutes. The mixture was diluted with methanol and applied to a SCX column eluting with methanol and then a mixture of 0.880 ammonia/methanol (1:9). The basic fractions were combined and concentrated in vacuo. The resulting residue was purified by column chromatography eluting with a mixture of ammonia:methanol:dichloromethane (0.5:4.5:95.880) to afford the title compound (20 mg); MS (ES+) m/e 381 [M+H]$^+$.

Example 265

2-[(3-Cyclobutyl-2,3,4,5-tetrahydro-1H-3-benzazepin-7-yl)oxy]benzonitrile (E265)

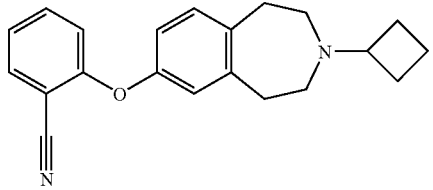

3-Cyclobutyl-2,3,4,5-tetrahydro-1H-benzo[d]azepin-7-ol (E3) (300 mg, 1.38 mmol) was dissolved in pyridine (10 ml), cooled in an ice bath and treated with sodium hydride (60% in mineral oil) (66 mg, 1.66 mmol) under argon. The resulting mixture was stirred for 5 minutes, treated with copper (I) bromide (277 mg, 1.93 mmol) and allowed to warm to room temperature over 30 minutes. A solution of 2-iodobenzonitrile (948 mg, 4.14 mmol) in pyridine (2 ml) was added and the mixture heated under reflux for 2.5 hours. The mixture was allowed to cool to room temperature and the solvent removed in vacuo. The resulting residue was purified by column chromatography eluting with a mixture of ammonia:methanol:dichloromethane (0.2:1.8:98) to afford the title compound (180 mg); MS (ES+) m/e 319 [M+H]$^+$.

Example 266

3-[(3-Cyclobutyl-2,3,4,5-tetrahydro-1H-3-benzazepin-7-yl)oxy]-N-methyl-4-(methyloxy)benzamide (E266)

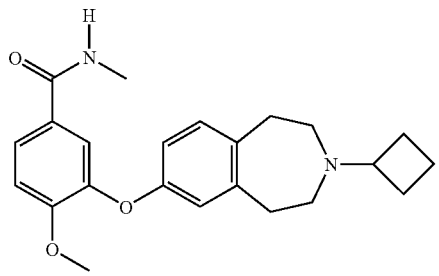

Step 1: 1,1-Dimethylethyl 7-({2-(methyloxy)-5-[(methyloxy)carbonyl]phenyl}oxy)-1,2,4,5-tetrahydro-3H-3-benzazepine-3-carboxylate The title compound was prepared from (3-{[(1,1-dimethylethyl)oxy]carbonyl}-2,3,4,5-tetrahydro-1H-3-benzazepin-7-yl)boronic acid (E264, Step 2) and methyl-3-hydroxy-4-methoxybenzoate using the method of Example 264 Step 3; MS (ES+) m/e 328 [(M+H)—CO$_2$$^t$Bu]$^+$.

Step 2: 3-[(3-{[(1,1-Dimethylethyl)oxy]carbonyl}-2,3,4,5-tetrahydro-1H-3-benzazepin-7-yl)oxy]-4-(methyloxy)benzoic acid The title compound was prepared from 1,1-dimethylethyl 7-({2-(methyloxy)-5-[(methyloxy)carbonyl]phenyl}oxy)-1,2,4,5-tetrahydro-3H-3-benzazepine-3-carboxylate (E266, Step 1) using the method of Example 264 Step 4; MS (ES+) m/e 314 [(M+H)—CO$_2$$^t$Bu]$^+$.

Step 3: 1,1-Dimethylethyl 7-{[5-[(methylamino)carbonyl]-2-(methyloxy)phenyl]oxy}-1,2,4,5-tetrahydro-3H-3-benzazepine-3-carboxylate The title compound was prepared from 3-[(3-{[(1,1-dimethylethyl)oxy]carbonyl}-2,3,4,5-tetrahydro-1H-3-benzazepin-7-yl)oxy]-4-(methyloxy)benzoic acid (E266, Step 2) and methylamine using the method of Example 264, Step 5; MS (ES+) m/e 327 [(M+H)—CO$_2$$^t$Bu]$^+$.

Step 4: N-Methyl-4-(methyloxy)-3-(2,3,4,5-tetrahydro-1H-3-benzazepin-7-yloxy)benzamide The title compound was prepared from 1,1-dimethylethyl 7-{[5-[(methylamino)carbonyl]-2-(methyloxy)phenyl]oxy}-1,2,4,5-tetrahydro-3H-3-benzazepine-3-carboxylate (E266, Step 3) using the method of Example 264 Step 6; MS (ES+) m/e 327 [M+H]$^+$.

Step 5: 3-[(3-Cyclobutyl-2,3,4,5-tetrahydro-1H-3-benzazepin-7-yl)oxy]-N-methyl-4-(methyloxy)benzamide The title compound was prepared from N-methyl-4-(methyloxy)-3-(2,3,4,5-tetrahydro-1H-3-benzazepin-7-yloxy)benzamide (E266, Step 4), using the method of Example 264 Step 7; MS (ES+) m/e 381 [M+H]$^+$.

Example 267

3-Chloro-4-[(3-cyclobutyl-2,3,4,5-tetrahydro-1H-3-benzazepin-7-yl)oxy]-N-methylbenzamide (E267)

Step 1: 1,1-Dimethylethyl 7-({2-chloro-4-[(methyloxy)carbonyl]phenyl}oxy)-1,2,4,5-tetrahydro-3H-3-benzazepine-3-carboxylate The title compound was prepared from methyl 3-chloro-4-hydroxy benzoate (320 mg, 1.72 mmol) and (3-{[(1,1-dimethylethyl)oxy]carbonyl}-2,3,4,5-tetrahydro-1H-3-benzazepin-7-yl)boronic acid (E264, Step 2) using the method outlined in Example 264 Step 3 (211 mg, 29%); NMR (CDCl$_3$) δ 1.49 (9H, s), 2.88 (4H, m), 3.56 (4H, m), 3.91 (3H, s), 6.78-6.89 (3H, m), 7.12 (H, m), 7.84 (H, m), 8.14 (H, s)

Step 2: 3-Chloro-4-[(3-{[(1,1-dimethylethyl)oxy]carbonyl}-2,3,4,5-tetrahydro-1H-3-benzazepin-7-yl)oxy]benzoic acid The title compound was prepared from 1,1-dimethylethyl 7-({2-chloro-4-[(methyloxy)carbonyl]phenyl}oxy)-1,2,4,5-tetrahydro-3H-3-benzazepine-3-carboxylate acid (E267, Step 1) using the method outlined in Example 264 Step 4; MS (ES−), m/e 416 & 418 [M−H].

Step 3: 1,1-Dimethylethyl 7-({2-chloro-4-[(methylamino)carbonyl]phenyl}oxy)-1,2,4,5-tetrahydro-3H-3-benzazepine-3-carboxylate The title compound was prepared from 3-chloro-4-[(3-{[(1,1-dimethylethyl)oxy]carbonyl}-2,3,4,5-tetrahydro-1H-3-benzazepin-7-yl)oxy]benzoic acid (E267, Step 2) and methylamine using the method outlined in Example 264 Step 5 (82 mg, 52%); MS (ES+), m/e 431 & 433 [M+H]$^+$.

Step 4: 3-Chloro-N-methyl-4-(2,3,4,5-tetrahydro-1H-3-benzazepin-7-yloxy)benzamide The title compound was prepared from 1,1-dimethylethyl 7-({2-chloro-4-[(methylamino)carbonyl]phenyl}oxy)-1,2,4,5-tetrahydro-3H-3-benzazepine-3-carboxylate (E267, Step 3) using the method outlined in Example 264 Step 6 (54 mg, 94%); MS (ES+), m/e 331 & 333 [M+H]$^+$.

Step 5: 3-Chloro-4-[(3-cyclobutyl-2,3,4,5-tetrahydro-1H-3-benzazepin-7-yl)oxy]-N-methylbenzamide The title compound was prepared from 3-chloro-N-methyl-4-(2,3,4,5-tetrahydro-1H-3-benzazepin-7-yloxy)benzamide (E267, Step 4) and cyclobutanone using the method outlined in Example 264 Step 7 (36 mg, 57%) MS (ES+), m/e 385 & 387 [M+H]$^+$.

Example 268

4-[(3-Cyclobutyl-2,3,4,5-tetrahydro-1H-3-benzazepin-7-yl)oxy]-N,3-dimethyl benzamide (E268)

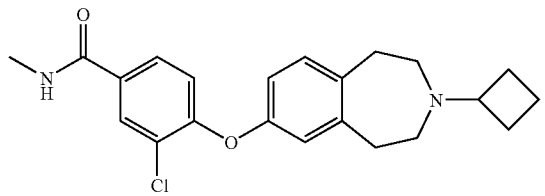

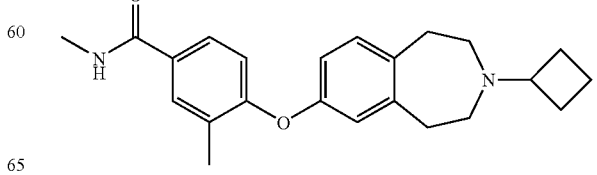

Step 1: 1,1-Dimethylethyl 7-({2-methyl-4-[(methyloxy)carbonyl]phenyl}oxy)-1,2,4,5-tetrahydro-3H-3-benzazepine-3-carboxylate The title compound was prepared from 7-hydroxy-1,2,4,5-tetrahydro-benzo[d]azepine-3-carboxylic acid tert-butyl ester (PCT Int. Appl. (2002), WO 02/40471) and methyl 4-bromo-3-methylbenzoate using the method outlined in Example 128 (211 mg, 29%); NMR (CDCl₃) δ 1.49 (9H, s), 2.32 (3H, m), 2.86 (4H, m), 3.55 (4H, m), 3.89 (3H, s), 6.71-6.81 (3H, m), 7.08 (H, m), 7.80 (H, m), 7.94 (H, s)

Step 2: 4-[(3-{[(1,1-Dimethylethyl)oxy]carbonyl}-2,3,4,5-tetrahydro-1H-3-benzazepin-7-yl)oxy]-3-methylbenzoic acid The title compound was prepared from 1,1-dimethylethyl 7-({2-methyl-4-[(methyloxy)carbonyl]phenyl}oxy)-1,2,4,5-tetrahydro-3H-3-benzazepine-3-carboxylate (E268, Step 1) using the method outlined in Example 264 Step 4; (247 mg, 94%) MS (ES–), m/e 396 [M–H].

Step 3: 1,1-Dimethylethyl 7-({2-methyl-4-[(methylamino)carbonyl]phenyl}oxy)-1,2,4,5-tetrahydro-3H-3-benzazepine-3-carboxylate The title compound was prepared from 4-[(3-{[(1,1-dimethylethyl)oxy]carbonyl}-2,3,4,5-tetrahydro-1H-3-benzazepin-7-yl)oxy]-3-methylbenzoic acid (E268, Step 2) and methylamine using the method outlined in Example 264 Step 5 (136 mg, 53%); MS (ES+), m/e 411 [M+H]⁺.

Step 4: N,3-Dimethyl-4-(2,3,4,5-tetrahydro-1H-3-benzazepin-7-yloxy)benzamide The title compound was prepared from 1,1-dimethylethyl 7-({2-methyl-4-[(methylamino)carbonyl]phenyl}oxy)-1,2,4,5-tetrahydro-3H-3-benzazepine-3-carboxylate (E268, Step 3) using the method outlined in Example 264 Step 6 (90 mg, 88%); MS (ES+), m/e 311 [M+H]⁺.

Step 5: 4-[(3-Cyclobutyl-2,3,4,5-tetrahydro-1H-3-benzazepin-7-yl)oxy]-N,3-dimethylbenzamide The title compound was prepared from N,3-dimethyl-4-(2,3,4,5-tetrahydro-1H-3-benzazepin-7-yloxy)benzamide (E268, Step 4) (90 mg, 0.29 mmol) and cyclobutanone (50 μl, 0.58 mmol) using the method outlined in Example 264 Step 7 (71 mg, 67%); MS (ES+), m/e 365 [M+H]⁺.

Example 269

3-Cyclobutyl-8-[(phenyl methyl)oxy]-2,3,4,5-tetrahydro-1H-3-benzazepine-7-carbonitrile (E269)

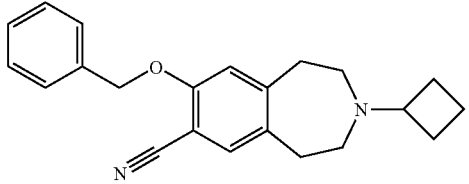

A mixture of 3-cyclobutyl-7-iodo-8-[(phenylmethyl)oxy]-2,3,4,5-tetrahydro-1H-3-benzazepine (E226) (250 mg, 0.58 mmol), tetrakis(triphenylphosphine)palladium (0) (33 mg, 0.029 mmol), copper (I) iodide (11 mg, 0.058 mmol) and sodium cyanide (56 mg, 1.15 mmol) in tetrahydrofuran (5 ml) was heated at reflux for 16 hours. The mixture was cooled and diluted with ethyl acetate, filtered through celite, washed with water then brine and dried over sodium sulfate and concentrated in vacuo. The crude mixture was purified by reverse phase HPLC to afford the title compound; MS (ES+) m/e 333 [M+H]⁺.

Example 270

3-Cyclobutyl-7-[(2-fluorophenyl)oxy]-2,3,4,5-tetrahydro-1H-3-benzazepine (E270)

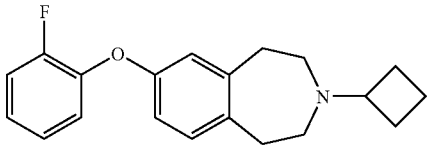

Example 270 (E270) was prepared from 3-cyclobutyl-2,3,4,5-tetrahydro-1H-benzo[d]azepin-7-ol (E3) and 2-fluoro iodobenzene using the method described for Example 128; MS (ES+) m/e 312 [M+H]⁺.

Example 271

4-[(3-Cyclobutyl-2,3,4,5-tetrahydro-1H-3-benzazepin-7-yl)oxy]-3-fluorobenzonitrile (E271)

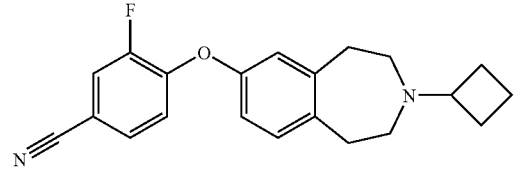

A mixture of 3-cyclobutyl-2,3,4,5-tetrahydro-1H-3-benzazepin-7-ol (E3) (100 mg, 0.46 mmol), 3,4-difluorobenzonitrile (70 mg, 0.51 mmol) and potassium carbonate (159 mg, 1.15 mmol) in dimethylsulfoxide (2 ml) was heated at 85° C. for 2 hours. The reaction mixture was cooled and applied to a SCX ion exchange cartridge (Varian bond-elute, 10 g) and washed with methanol and then a mixture of 0.880 ammonia/methanol (1:9). The combined basic fractions were concentrated in vacuo to afford the title compound (E271). MS (ES+) m/e 337 [M+H]⁺.

Example 272

4-[(3-Cyclobutyl-2,3,4,5-tetrahydro-1H-3-benzazepin-7-yl)oxy]-3-fluorobenzoic acid (E272)

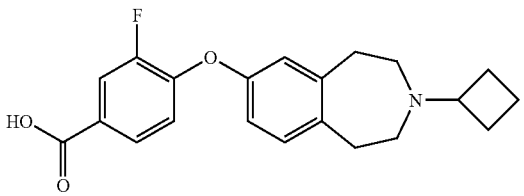

4-[(3-Cyclobutyl-2,3,4,5-tetrahydro-1H-3-benzazepin-7-yl)oxy]-3-fluorobenzonitrile (E271) (150 mg, 0.45 mmol)

was dissolved in a mixture of ethanol (1 ml) and water (1.5 ml), treated with sodium hydroxide (150 mg, 4.5 mmol) and heated at reflux for 2 hours. The reaction was then treated with acetic acid (0.39 ml, 6.75 mmol) and concentrated in vacuo. The resulting residue was purified by column chromatography eluting with a mixture of 0.880 ammonia:methanol:dichloromethane (2:18:80) to afford the title compound. MS (ES+) m/e 356 [M+H]+.

Example 273

4-[(3-Cyclobutyl-2,3,4,5-tetrahydro-1H-3-benzazepin-7-yl)oxy]-3-fluoro-N-methylbenzamide (E273)

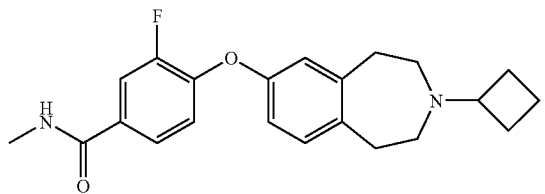

A solution of 4-[(3-cyclobutyl-2,3,4,5-tetrahydro-1H-3-benzazepin-7-yl)oxy]-3-fluorobenzoic acid (E272) (164 mg, 0.36 mmol) and O-(7-azabenzotriazol-1-yl)-N,N,N',N'-tetramethyluronium hexafluorophosphate (438 mg, 1.15 mmol) in dimethylformamide (2 ml) was treated with diisopropyl ethylamine (0.40 ml, 2.3 mmol) followed by a 2M methylamine solution in tetrahydrofuran (2 ml). The reaction was stirred at room temperature for 4 hours, applied to a SCX ion exchange column (Varian bond-elute, 10 g) and washed with methanol and then a mixture of 0.880 ammonia/methanol, and the basic fractions concentrated in vacuo. The resulting residue was purified by column chromatography eluting with a mixture of 0.880 ammonia:methanol:dichloromethane (0.5:4.5:95) to afford the title compound. MS (ES+) m/e 369 [M+H]+.

Example 274

3-Cyclobutyl-7-[(2-fluoro-4-iodophenyl)oxy]-2,3,4,5-tetrahydro-1H-3-benzazepine (E274)

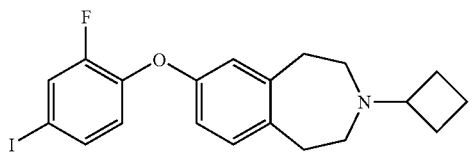

Step 1: 1,1-Dimethylethyl 7-[(2-fluoro-4-nitrophenyl)oxy]-1,2,4,5-tetrahydro-3H-3-benzazepine-3-carboxylate 3,4-difluoronitrobenzene (664 mg, 4.18 mmol) was added to a mixture of 7-hydroxy-1,2,4,5-tetrahydro-benzo[d]azepine-3-carboxylic acid tert-butyl ester (WO 02/40471) (1 g, 3.8 mmol) and potassium carbonate (1.3 g, 9.49 mmol) in dimethylformamide (10 ml) and the reaction heated at 130° C. for 3 hours. The reaction was cooled, diluted with ethyl acetate, washed with water and then with a mixture of water: brine (1:1), dried over sodium sulfate and concentrated in vacuo. The resulting residue was purified by column chromatography eluting with a mixture of ethyl acetate:pentane (1:10) to afford the title compound. MS (ES+) m/e 303 [M-COOtBu]+.

Step 2: 1,1-Dimethylethyl 7-[(4-amino-2-fluorophenyl)oxy]-1,2,4,5-tetrahydro-3H-3-benzazepine-3-carboxylate To a solution of 1,1-dimethylethyl 7-[(2-fluoro-4-nitrophenyl)oxy]-1,2,4,5-tetrahydro-3H-3-benzazepine-3-carboxylate (E274, Step 1) (1.37 g, 3.40 mmol) in ethanol (25 ml) was added palladium on charcoal (10 wt % palladium) (300 mg) and the reaction was stirred at room temperature under hydrogen (1 atmosphere) for 3 hours. The reaction mixture was filtered through celite and concentrated in vacuo to afford the title compound. MS (ES+) m/e 273 [M-M-COOtBu]+.

Step 3: 1,1-Dimethylethyl 7-[(2-fluoro-4-iodophenyl)oxy]-1,2,4,5-tetrahydro-3H-3-benzazepine-3-carboxylate To a solution of 1,1-dimethylethyl 7-[(4-amino-2-fluorophenyl)oxy]-1,2,4,5-tetrahydro-3H-3-benzazepine-3-carboxylate (E274, Step 2) (0.5 g, 1.34 mmol) and iodoform (1 g, 2.69 mmol) in tetrahydrofuran (10 ml) was added dropwise tert-butyl nitrite (0.32 ml, 2.69 mmol). The reaction was then heated at reflux for 1 hour, cooled and concentrated in vacuo and resulting residue was purified by column chromatography eluting with a mixture of ethyl acetate:pentane (1:10) to afford the title compound. MS (ES+) m/e 384 [M-COOtBu]+.

Step 4: 7-[(2-Fluoro-4-iodophenyl)oxy]-2,3,4,5-tetrahydro-1H-3-benzazepine

The title compound was prepared from 1,1-dimethylethyl 7-[(2-fluoro-4-iodophenyl)oxy]-1,2,4,5-tetrahydro-3H-3-benzazepine-3-carboxylate (E274, Step 3) using an analogous method to that described for Description 2 (D2). MS (ES+) m/e 384 [M+H]+.

Step 5: 3-Cyclobutyl-7-[(2-fluoro-4-iodophenyl)oxy]-2,3,4,5-tetrahydro-1H-3-benzazepine The title compound was prepared from 7-[(2-fluoro-4-iodophenyl)oxy]-2,3,4,5-tetrahydro-1H-3-benzazepine (E274, Step 4) using an analogous method to that described for Example 1 (E1). MS (ES+) m/e 438 [M+H]+.

Example 275

1-{4-[(3-Cyclobutyl-2,3,4,5-tetrahydro-1H-3-benzazepin-7-yl)oxy]-3-fluorophenyl}-2-pyrrolidinone (E275)

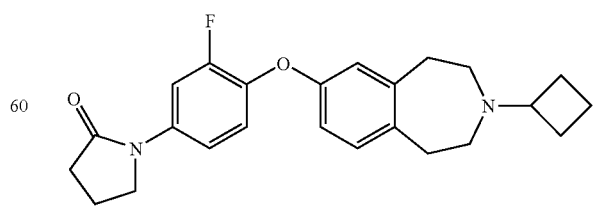

The title product was prepared from 3-cyclobutyl-7-[(2-fluoro-4-iodophenyl)oxy]-2,3,4,5-tetrahydro-1H-3-benza-

Example 276

N-{4-[(3-Cyclobutyl-2,3,4,5-tetrahydro-1H-3-benzazepin-7-yl)oxy]-3-fluorophenyl}acetamide (E276)

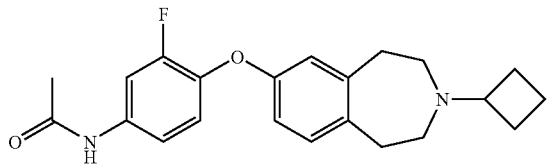

Step 1: 1,1-Dimethylethyl 7-{[4-(acetylamino)-2-fluorophenyl]oxy}-1,2,4,5-tetrahydro-3H-3-benzazepine-3-carboxylate To a solution of 1,1-dimethylethyl 7-[(4-amino-2-fluorophenyl)oxy]-1,2,4,5-tetrahydro-3H-3-benzazepine-3-carboxylate (E274, Step 2) (250 mg, 0.67 mmol) in dichloromethane (10 ml) was added triethylamine (0.19 ml, 1.34 mmol) and acetyl chloride (50 μL, 0.74 ml) and the reaction stirred at room temperature for 16 hours. The reaction was then diluted with dichloromethane and washed with a 3N aqueous solution of citric acid, then saturated sodium bicarbonate then water and the dichloromethane dried over sodium sulfate and concentrated in vacuo. The resulting residue was purified by column chromatography eluting with a mixture of ethyl acetate:pentane (1:1) to afford the title compound. MS (ES+) m/e 413 [M−H]⁻.

Step 2: N-{4-[(3-Cyclobutyl-2,3,4,5-tetrahydro-1H-3-benzazepin-7-yl)oxy]-3-fluorophenyl}acetamide The title compound was prepared from 1,1-dimethylethyl 7-{[4-(acetylamino)-2-fluorophenyl]oxy}-1,2,4,5-tetrahydro-3H-3-benzazepine-3-carboxylate (E276, Step 1) via an analogous 2 step procedure described in Example 274 steps 4-5. MS (ES+) m/e 369 [M+H]⁺.

Example 277

Example 277 (E277) was prepared from 3-cyclobutyl-2,3,4,5-tetrahydro-1H-benzo[d]azepin-7-ol (E3) and the appropriate aromatic iodide indicated in the table using an analogous method to that described for Example 128 (E128):

| Example | Aromatic Iodide | LC/MS [M + H]⁺ |
|---|---|---|
| 1-[3-(3-Cyclobutyl-2,3,4,5-tetrahydro-1H-benzo[d]azepin-7-yloxy)-phenyl]-1-pyrrolidin-1-yl-methanone (E277) | 1-[(3-Iodophenyl)carbonyl]pyrrolidine (D52) | 391 |

Example 278

Example 278 (E278) was prepared from 5-[(3-cyclobutyl-2,3,4,5-tetrahydro-1H-3-benzazepin-7-yl)oxy]-2-pyridinecarboxylic acid (E187a) and the appropriate amine indicated in the table using an analogous method to that described for Example 177 (E177):

| Example | Amine | LC/MS [M + H]⁺ |
|---|---|---|
| 5-[(3-Cyclobutyl-2,3,4,5-tetrahydro-1H-3-benzazepin-7-yl)oxy]-N-(tetrahydro-2H-pyran-4-yl)-2-pyridinecarboxamide (E278) | Tetrahydro-2H-pyran-4-amine | 422 |

Example 279

3-Cyano-4-[(3-cyclobutyl-2,3,4,5-tetrahydro-1H-3-benzazepin-7-yl)oxy]-N-methylbenzamide (E279)

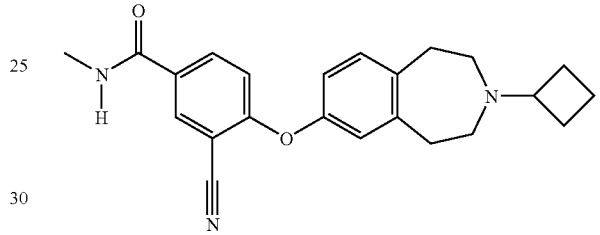

Step 1: 3-Cyano-4-(methyloxy)benzoic acid

The title compound was prepared from methyl 3-cyano-4-(methyloxy)benzoate using the method of Example 264 Step 4; ¹H NMR (CDCl₃) 8.32 (1H, d), 8.29-8.27 (1H, dd), 7.06-7.04 (1H, d), 4.03 (3H, s).

Step 2: 3-Cyano-N-methyl-4-(methyloxy)benzamide

The title compound was prepared from 3-cyano-4-(methyloxy)benzoic acid (E279, Step 1), using the method of Example 264 Step 5; MS (ES+) m/e 191 [M+H]⁺.

Step 3: 3-Cyano-4-hydroxy-N-methylbenzamide

3-Cyano-N-methyl-4-(methyloxy)benzamide (E279, Step 2) (346 mg, 1.82 mmol), was dissolved in dry dichloromethane (10 ml), cooled to 0° C. and treated with boron tribromide (1 M solution in dichloromethane) (9.11 ml, 9.11 mmol). The mixture was stirred for 30 minutes, allowed to warm to room temperature and stirred for 18 hours. The mixture was cooled in an ice bath, treated with water added dropwise and then allowed to warm to room temperature. The mixture was poured onto 2M hydrochloric acid (10 ml) and extracted with ethyl acetate. The ethyl acetate layers were combined, dried under magnesium sulfate and evaporated in vacuo. The resulting residue was purified by column chromatography eluting with a mixture of ethyl acetate dichloromethane (1:1) to afford the title compound (86 mg); MS (ES+) m/e 177 [M+H]⁺.

Step 4: 1,1-Dimethylethyl 7-({2-cyano-4-[(methylamino)carbonyl]phenyl}oxy)-1,2,4,5-tetrahydro-3H-3-benzazepine-3-carboxylate The title compound was prepared from 3-cyano-4-hydroxy-N-methylbenzamide (E279, Step 3) and (3-{[(1,1-dimethylethyl)oxy]carbonyl}-2,3,4,5-tetrahydro-1H-3-benzazepin-7-yl)boronic acid (E264, Step 2), using the method of Example 264 Step 3; MS (ES+) m/e 322 [(M+H)—CO₂ᵗBu]⁺.

Step 5: 3-Cyano-N-methyl-4-(2,3,4,5-tetrahydro-1H-3-benzazepin-7-yloxy)benzamide The title compound was prepared from 1,1-dimethylethyl 7-({2-cyano-4-[(methylamino)carbonyl]phenyl}oxy)-1,2,4,5-tetrahydro-3H-3-benzazepine-3-carboxylate (E279, Step 4) using the method of Example 264 Step 6; MS (ES+) m/e 322 [M+H]⁺.

Step 6: 3-Cyano-4-[(3-cyclobutyl-2,3,4,5-tetrahydro-1H-3-benzazepin-7-yl)oxy]-N-methylbenzamide The title compound was prepared from 3-cyano-N-methyl-4-(2,3,4,5-tetrahydro-1H-3-benzazepin-7-yloxy)benzamide (E279, Step 5), using the method of Example 264 Step 7; MS (ES+) m/e 376 [M+H]⁺.

Example 280

3-Cyclobutyl-7-{[6-(4-morpholinylcarbonyl)-3-pyridazinyl]oxy}-2,3,4,5-tetrahydro-1H-3-benzazepine (E280)

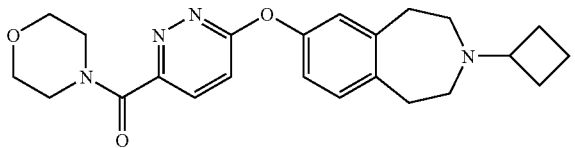

Step 1: 4-[(6-Chloro-3-pyridazinyl)carbonyl]morpholine

A mixture of 6-oxo-1,6-dihydro-3-pyridazinecarboxylic acid (A. E Mourad et al J. Het. Chem 1992; 29 (6), 1583-1592; 0.5 g) in phosphorus oxychloride (2 ml) was heated under reflux for 2 h. Excess phosphorus oxychloride was evaporated and THF (5 ml) added to the residue. The solution was then cooled to 0° C. and triethylamine (1.1 ml) added, followed by morpholine (1.87 ml). The mixture was allowed to warm to room temperature, stirred for 16 h then diluted with ethyl acetate (10 ml) and filtered. The filtrate was evaporated and purified by chromatography on silica gel, eluting with ethyl acetate to afford the title compound; MS (ES+) m/e 228 [M+H]⁺.

Step 2: 3-Cyclobutyl-7-{[6-(4-morpholinylcarbonyl)-3-pyridazinyl]oxy}-2,3,4,5-tetrahydro-1H-3-benzazepine A mixture of 3-cyclobutyl-2,3,4,5-tetrahydro-1H-3-benzazepine-7-ol (E3) (84 mg, 0.385 mmol), 4-[(6-chloro-3-pyridazinyl)carbonyl]morpholine (E280, Step 1) (70 mg, 0.308 mmol) and potassium carbonate (85 mg, 0.616 mmol) in dry acetone (3 ml) was heated at 140° C. for 2×15 mins. (300 W) in a microwave reactor. The cooled reaction mixture was filtered, concentrated in vacuo. and Purified by column chromatography on silica gel, eluting with a mixture of 0.880 ammonia:methanol:dichloromethane (0.5:4.5:190) to afford the title compound; MS (ES+) m/e 409 [M+H]⁺.

Examples 281-282

Examples 281-282 (E281-282) were prepared from 3-cyclobutyl-2,3,4,5-tetrahydro-1H-3-benzazepine-7-ol (E3) and 6-oxo-1,6-dihydro-3-pyridazinecarboxylic acid using the appropriate amine as indicated in the table using the two step procedure as described for Example 280:

| Example | Amine | LC/MS (M + H⁺) |
|---|---|---|
| 6-[(3-Cyclobutyl-2,3,4,5-tetrahydro-1H-3-benzazepin-7-yl)oxy]-N-methyl-3-pyridazinecarboxamide (E281) | Methylamine | 353 |
| 6-[(3-Cyclobutyl-2,3,4,5-tetrahydro-1H-3-benzazepin-7-yl)oxy]-N-ethyl-N-methyl-3-pyridazinecarboxamide (E282) | Ethyl(methyl)amine | 381 |

Example 283

3-Cyclobutyl-7-{[4-(4-morpholinyl)-4-oxobutyl]oxy}-2,3,4,5-tetrahydro-1H-3-benzazepine (E283)

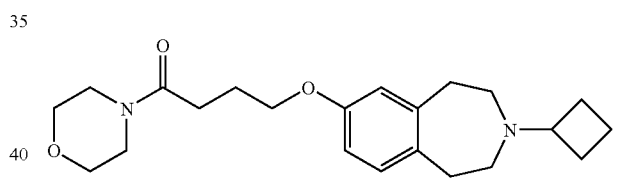

Step 1: 4-[(3-Cyclobutyl-2,3,4,5-tetrahydro-1H-3-benzazepin-7-yl)oxy]butanoic acid Ethyl 4-[(3-cyclobutyl-2,3,4,5-tetrahydro-1H-3-benzazepin-7-yl)oxy]butanoate (E167a) (2.2 g, 6.6 mmol) was dissolved in methanol (40 ml) and treated with 2N sodium hydroxide (10.0 ml). After stirring at reflux for 1 hour, the reaction mixture was cooled to room temperature and concentrated in vacuo. The crude mixture was applied to a SCX ion exchange cartridge (Varian bond-elute) and washed with water and then methanol. The organic fractions were reduced in vacuo to afford the title compound (E283); MS (ES+) m/e 304 [M+H]⁺.

Step 2: 3-Cyclobutyl-7-{[4-(4-morpholinyl)-4-oxobutyl]oxy}-2,3,4,5-tetrahydro-1H-3-benzazepine 4-[(3-cyclobutyl-2,3,4,5-tetrahydro-1H-3-benzazepin-7-yl)oxy]butanoic acid (E283, Step 1) (0.15 g, 0.50 mmole) was dissolved in dry dichloromethane (5 ml) and dry dimethylformamide (2 ml) was treated with 1-hydroxybenzotriazole hydrate (0.14 g, 1.0 mmole) and N-cyclohexylcarbodiimide, N'-methyl polystyrene HL (0.53 g, 1.0 mmol, 1.7 mmol/g) and stirred for 45 minutes. Morpholine (0.056 ml, 0.65 mmol)

was added and the mixture stirred for 3 hours at ambient temperature. The crude reaction mixture was applied to a SCX ion exchange cartridge (Varian bond-elute) and washed with water, methanol and then a mixture of 0.880 ammonia:methanol (1:9). The combined basic fractions were reduced in vacuo. The resulting residue was purified by column chromatography eluting with a mixture of 0.880 ammonia:methanol:dichloromethane (0.5:4.5:95 to 1:9:90) to afford the title compound (E283); MS (ES+) m/e 373 [M+H]+.

Examples 284-285

Examples 284-285 (E284-285) were prepared from 3-cyclobutyl-7-(piperidin-4-yloxy)-2,3,4,5-tetrahydro-1H-benzo[d]azepine (E6) and the appropriate acid as indicated in the table using an analogous method to that described for Example 13 (E13):

| Example | Acid | LC/MS (M + H+) |
| --- | --- | --- |
| 3-Cyclobutyl-7-[(1-{[4-(4-morpholinyl)phenyl]carbonyl}-4-piperidinyl)oxy]-2,3,4,5-tetrahydro-1H-3-benzazepine (E284) | 4-(4-Morpholinyl)-benzoic acid | 490 |
| 3-Cyclobutyl-7-{[1-(cyclopropylacetyl)-4-piperidinyl]oxy}-2,3,4,5-tetrahydro-1H-3-benzazepine (E285) | Cyclopropylacetic acid | 383 |

Example 286

3-Cyclobutyl-7-[(1-{[(2R,6S)-2,6-dimethyl-4-morpholinyl]carbonyl}-4-piperidinyl)oxy]-2,3,4,5-tetrahydro-1H-3-benzazepine (E286)

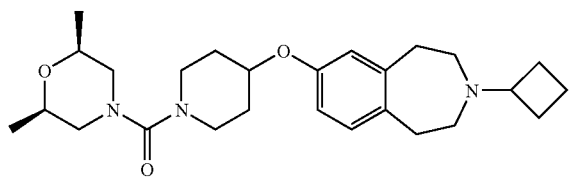

Example 286 (E286) was prepared from 3-cyclobutyl-7-(piperidin-4-yloxy)-2,3,4,5-tetrahydro-1H-benzo[d]azepine (E6) and cis-2,6-dimethylmorpholine using the method described for Example 61 (E61); MS (ES+) m/e 442 [M+H]+.

Example 287

3-Cyclobutyl-7-{[trans-4-(4-morpholinylcarbonyl)cyclohexyl]oxy}-2,3,4,5-tetrahydro-1H-3-benzazepine (E287)

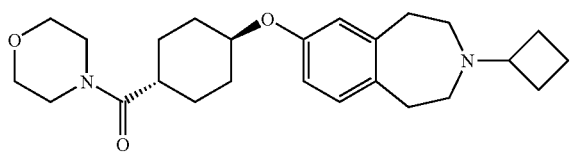

Example 287 (E287) was prepared from 3-cyclobutyl-7-(piperidin-4-yloxy)-2,3,4,5-tetrahydro-1H-benzo[d]azepine (E6) and cis-4-(4-morpholinylcarbonyl)-cyclohexanol (D55) using the method described for Example 5a (E5a); MS (ES+) m/e 413 [M+H]+.

All publications, including but not limited to patents and patent applications, cited in this specification are herein incorporated by reference as if each individual publication were specifically and individually indicated to be incorporated by reference herein as though fully set forth.

Example 288

3-Cyclobutyl-7-{[6-(4-morpholinyl)-2-pyrazinyl]oxy}-2,3,4,5-tetrahydro-1H-3-benzazepine (E288)

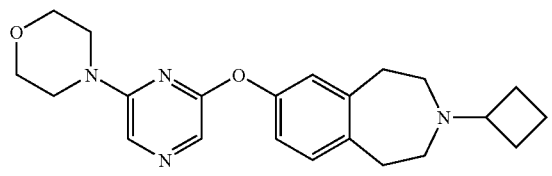

Example (E288) was prepared from 3-cyclobutyl-2,3,4,5-tetrahydro-1H-benzo[d]azepin-7-ol (E3) and 4-(6-chloro-2-pyrazinyl)morpholine [Zagulyaeva, . A., J. Org. Chem. USSR, EN, 14; 1978; 377-380] using an analogous method to that described for Example 242 (E242); MS (ES+) m/e 381 [M+H]+.

Biological Data

A membrane preparation containing histamine H3 receptors may be prepared in accordance with the following procedures:

(i) Generation of Histamine H3 Cell Line

DNA encoding the human histamine H3 gene (Huvar, A. et al. (1999) Mol. Pharmacol. 55(6), 1101-1107) was cloned into a holding vector, pcDNA3.1 TOPO (InVitrogen) and its cDNA was isolated from this vector by restriction digestion of plasmid DNA with the enzymes BamH1 and Not-1 and ligated into the inducible expression vector pGene (InVitrogen) digested with the same enzymes. The GeneSwitch™ system (a system where in transgene expression is switched off in the absence of an inducer and switched on in the presence of an inducer) was performed as described in U.S. Pat. Nos. 5,364,791; 5,874,534; and 5,935,934. Ligated DNA was transformed into competent DH5α E. coli host bacterial cells and plated onto Luria Broth (LB) agar containing Zeocin™ (an antibiotic which allows the selection of cells expressing the sh ble gene which is present on pGene and pSwitch) at 50 μg ml−1. Colonies containing the re-ligated plasmid were identified by restriction analysis. DNA for transfection into mammalian cells was prepared from 250 ml cultures of the host bacterium containing the pGeneH3 plasmid and isolated using a DNA preparation kit (Qiagen Midi-Prep) as per manufacturers guidelines (Qiagen).

CHO K1 cells previously transfected with the pSwitch regulatory plasmid (InVitrogen) were seeded at 2×10e6 cells per T75 flask in Complete Medium, containing Hams F12 (GIBCOBRL, Life Technologies) medium supplemented with 10% v/v dialysed foetal bovine serum, L-glutamine, and hygromycin (100 μg ml−1), 24 hours prior to use. Plasmid DNA was transfected into the cells using Lipofectamine plus according to the manufacturers guidelines (InVitrogen). 48 hours post transfection cells were placed into complete medium supplemented with 500 µg ml$^{-1}$ Zeocin™.

10-14 days post selection 10 nM Mifepristone (InVitrogen), was added to the culture medium to induce the expression of the receptor. 18 hours post induction cells were detached from the flask using ethylenediamine tetra-acetic acid (EDTA; 1:5000; InVitrogen), following several washes with phosphate buffered saline pH 7.4 and resuspended in Sorting Medium containing Minimum Essential Medium (MEM), without phenol red, and supplemented with Earles salts and 3% Foetal Clone II (Hyclone). Approximately 1×10e7 cells were examined for receptor expression by staining with a rabbit polyclonal antibody, 4a, raised against the N-terminal domain of the histamine H3 receptor, incubated on ice for 60 minutes, followed by two washes in sorting medium. Receptor bound antibody was detected by incubation of the cells for 60 minutes on ice with a goat anti rabbit antibody, conjugated with Alexa 488 fluorescence marker (Molecular Probes). Following two further washes with Sorting Medium, cells were filtered through a 50 µm Filcon™ (BD Biosciences) and then analysed on a FACS Vantage SE Flow Cytometer fitted with an Automatic Cell Deposition Unit. Control cells were non-induced cells treated in a similar manner. Positively stained cells were sorted as single cells into 96-well plates, containing Complete Medium containing 500 µg ml$^{-1}$ Zeocin™ and allowed to expand before reanalysis for receptor expression via antibody and ligand binding studies. One clone, 3H3, was selected for membrane preparation.

(ii) Membrane Preparation from Cultured Cells

All steps of the protocol are carried out at 4° C. and with pre-cooled reagents. The cell pellet is resuspended in 10 volumes of buffer A2 containing 50 mM N-2-hydroxyethylpiperazine-N'-2-ethanesulfonic acid (HEPES) (pH 7.40) supplemented with 10e–4M leupeptin (acetyl-leucyl-leucyl-arginal; Sigma L2884), 25 µg/ml bacitracin (Sigma B0125), 1 mM ethylenediamine tetra-acetic acid (EDTA), 1 mM phenylmethylsulfonyl fluoride (PMSF) and 2×10e–6M pepstain A (Sigma). The cells are then homogenised by 2×15 second bursts in a 1 liter glass Waring blender, followed by centrifugation at 500 g for 20 minutes. The supernatant is then spun at 48,000 g for 30 minutes. The pellet is resuspended in 4 volumes of buffer A2 by vortexing for 5 seconds, followed by homogenisation in a Dounce homogeniser (10-15 strokes). At this point the preparation is aliquoted into polypropylene tubes and stored at −70° C.

Compounds of the invention may be tested for in vitro biological activity in accordance with the following assays:

(I) Histamine H3 Binding Assay

For each compound being assayed, in a white walled clear bottom 96 well plate, is added:—

(a) 10 µl of test compound (or 10 µl of iodophenpropit (a known histamine H3 antagonist) at a final concentration of 10 mM) diluted to the required concentration in 10% DMSO;

(b) 10 µl $^{125}$I 4-[3-(4-iodophenylmethoxy)propyl]-1H-imidazolium (iodoproxyfan) (Amersham;

1.85 MBq/µl or 50 µCi/ml; Specific Activity ~2000 Ci/mmol) diluted to 200 µM in assay buffer (50 mM Tris(hydroxymethyl)aminomethane buffer (TRIS) pH 7.4, 0.5 mM ethylenediamine tetra-acetic acid (EDTA)) to give 20 µM final concentration; and (c) 80 µl bead/membrane mix prepared by suspending Scintillation Proximity Assay (SPA) bead type WGA-PVT at 100 mg/ml in assay buffer followed by mixing with membrane (prepared in accordance with the methodology described above) and diluting in assay buffer to give a final volume of 80 µl which contains 7.5 µg protein and 0.25 mg bead per well—mixture was pre-mixed at room temperature for 60 minutes on a roller.

The plate is shaken for 5 minutes and then allowed to stand at room temperature for 3-4 hours prior to reading in a Wallac Microbeta counter on a 1 minute normalised tritium count protocol. Data was analysed using a 4-parameter logistic equation.

(II) Histamine H3 Functional Antagonist Assay

For each compound being assayed, in a white walled clear bottom 96 well plate, is added:—

(a) 10 µl of test compound (or 10 µl of guanosine 5'-triphosphate (GTP) (Sigma) as non-specific binding control) diluted to required concentration in assay buffer (20 mM N-2-Hydroxyethylpiperazine-N'-2-ethanesulfonic acid (HEPES)+ 100 mM NaCl+10 mM MgCl$_2$, pH7.4 NaOH);

(b) 60 µl bead/membrane/GDP mix prepared by suspending wheat germ agglutinin-polyvinyltoluene (WGA-PVT) scintillation proximity assay (SPA) beads at 100 mg/ml in assay buffer followed by mixing with membrane (prepared in accordance with the methodology described above) and diluting in assay buffer to give a final volume of 60 µl which contains 10 g protein and 0.5 mg bead per well—mixture is pre-mixed at 4° C. for 30 minutes on a roller and just prior to addition to the plate, 10 µM final concentration of guanosine 5' diphosphate (GDP) (Sigma; diluted in assay buffer) is added;

The plate is incubated at room temperature to equilibrate antagonist with receptor/beads by shaking for 30 minutes followed by addition of:

(c) 10 µl histamine (Tocris) at a final concentration of 0.3 µM; and (d) 20 µl guanosine 5' [γ35-S] thiotriphosphate, triethylamine salt (Amersham; radioactivity concentration=37 kBq/µl or 1 mCi/ml; Specific Activity 1160 Ci/mmol) diluted to 1.9 nM in assay buffer to give 0.38 nM final.

The plate is then incubated on a shaker at room temperature for 30 minutes followed by centrifugation for 5 minutes at 1500 rpm. The plate is read between 3 and 6 hours after completion of centrifuge run in a Wallac Microbeta counter on a 1 minute normalised tritium count protocol. Data is analysed using a 4-parameter logistic equation. Basal activity used as minimum i.e. histamine not added to well.

Results

The compounds of Examples E1-3, E5-149, E151-230, E233-235, E237-256, E258, E260-270, E273 and E275-288 were tested in the histamine H3 functional antagonist assay and exhibited antagonism in the following range: 6.5-10.5 pK$_b$. More particularly, the compounds of Examples 1, 52, 121, 125 and 217 exhibited antagonism in the following range 9.0-10.5 pK$_b$. Yet more particularly, the compound of Example 121 exhibited antagonism>9.5 pK$_b$.

The invention claimed is:

1. A method of treatment of cognitive impairments in Alzheimer's disease, mild cognitive impairment, age-related memory dysfunction, epilepsy, neuropathic pain, Parkinson's disease, cognitive deficit of schizophrenia, attention deficit hyperactivity disorder, or depression, in a human, which comprises administering to said human, an effective amount of a compound of formula (I) or a pharmaceutically acceptable salt thereof:

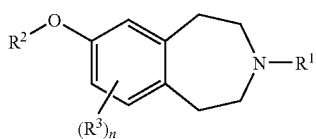

wherein:
$R^1$ represents —$C_{3-7}$ cycloalkyl optionally substituted by $C_{1-3}$ alkyl;
$R^2$ represents:
hydrogen;
—$C_{1-6}$ alkyl, optionally substituted by a —$CO_2R^4$ or —$CONR^5R^6$ group;
—X—$C_{3-8}$ cycloalkyl-Y-heterocyclyl;
—X-aryl-Y—$C_{3-8}$ cycloalkyl;
—X-aryl, optionally substituted by one or two halogen, $C_{1-6}$ alkyl, $C_{1-6}$ alkoxy, —$CO_2R^4$, —$CONR^5R^6$, —$NR^5COR^6$, —$SO_2NR^5R^6$ or cyano groups;
—X-aryl-Y-heterocyclyl, optionally substituted by one or two =O, halogen or $R^4$ groups;
—X-heteroaryl, optionally substituted by one or two halogen, $C_{1-6}$ alkyl, $C_{1-6}$ alkoxy, cyano, nitro, hydroxy, —$COR^4$, —$CO_2R^4$, —$NR^5R^6$, —$NR^5COR^6$, —$CONR^5R^6$ or =O groups;
—X-heteroaryl-Y-aryl, optionally substituted by a $C_{1-6}$ alkylsulfonyl or —$NR^5COR^6$ group;
—X-heteroaryl-Y-heteroaryl, optionally substituted by a $C_{1-6}$ alkyl group;
—X-heteroaryl-Y-heterocyclyl, optionally substituted by one or two =O, $C_{1-6}$ alkyl, hydroxy, or halogen groups;
—X-heterocyclyl, optionally substituted by a $C_{1-6}$ alkylsulfonyl, $C_{1-6}$ alkoxycarbonyl, —$CO_2R^4$, —$COR^4$ or —$CONR^5R^6$ group;
—X-heterocyclyl-Y-aryl, optionally substituted by a halogen, cyano, $C_{1-6}$ alkylsulfonyl, $R^4$ or —$CONR^5R^6$ group;
—X-heterocyclyl-Y-heterocyclyl, optionally substituted by one or two =O or $R^4$ groups;
—X-heterocyclyl-Y—$C_{3-8}$ cycloalkyl; or
—X-heterocyclyl-Y-heteroaryl, optionally substituted by one or two $C_{1-6}$ alkyl, =O, cyano or —$CONR^5R^6$ groups;
X represents a bond or $C_{1-6}$ alkyl;
Y represents a bond, $C_{1-6}$ alkyl, CO, $COC_{2-6}$ alkenyl, O or $SO_2$;
$R^3$ represents halogen, $C_{1-6}$ alkyl, $C_{1-6}$ alkoxy, cyano, amino or trifluoromethyl;
n is 0, 1 or 2; and
$R^4$, $R^5$ and $R^6$ independently represent hydrogen, $C_{1-6}$ alkyl, —$C_{3-8}$ cycloalkyl, —$C_{1-6}$ alkyl-$C_{3-8}$ cycloalkyl, aryl, heterocyclyl or heteroaryl or —$NR^5R^6$ may represent a nitrogen containing heterocyclyl group, wherein said $R^4$, $R^5$ and $R^6$ groups may be optionally substituted by 1, 2 or 3 substituents which may be the same or different, and which are selected from the group consisting of halogen, hydroxy, $C_{1-6}$ alkyl, $C_{1-6}$ alkoxy, cyano, amino, =O or trifluoromethyl; and
wherein when $R^2$ represents —X-heterocyclyl, —X-heterocyclyl-Y—$C_{3-8}$ cycloalkyl, —X-heterocyclyl-Y-aryl, —X-heterocyclyl-Y-heteroaryl or —X-heterocyclyl-Y-heterocyclyl, said heterocyclyl group is attached to X via a carbon atom.

2. The method of claim 1 wherein $R^1$ represents unsubstituted cyclobutyl, cyclopentyl or cyclohexyl.

3. The method of claim 1 wherein $R^1$ represents unsubstituted cyclobutyl.

4. The method of claim 1 wherein $R^2$ represents:
—X-aryl, optionally substituted by one or two halogen, $C_{1-6}$ alkyl, $C_{1-6}$ alkoxy, —$CO_2R^4$, —$CONR^5R^6$, —$NR^5COR^6$, —$SO_2NR^5R^6$ or cyano groups;
—X-aryl-Y-heterocyclyl, optionally substituted by one or two =O, halogen or $R^4$ groups;
—X-heteroaryl, optionally substituted by one or two halogen, $C_{1-6}$ alkyl, $C_{1-6}$ alkoxy, cyano, nitro, hydroxy, —$CO_2R^4$, —$COR^4$, —$NR^5R^6$, —$NR^5COR^6$, —$CONR^5R^6$ or =O groups;
—X-heteroaryl-Y-heterocyclyl, optionally substituted by one or two =O, $C_{1-6}$ alkyl, hydroxy or halogen groups; or
—X-heterocyclyl-Y-heterocyclyl, optionally substituted by one or two =O or $R^4$ groups.

5. The method of claim 4 wherein $R^2$ represents:
—X-aryl, optionally substituted by one or two halogen, $C_{1-6}$ alkoxy, —$CONR^5R^6$, —$NR^5COR^6$ or cyano groups;
—X-aryl-Y-heterocyclyl, optionally substituted by one or two =O or halogen groups; unsubstituted —X-heterocyclyl-Y-heterocyclyl;
—X-heteroaryl, optionally substituted by CON(H)(Me); or
—X-heteroaryl-Y-heterocyclyl, wherein said heterocyclyl group is optionally substituted by an =O group.

6. The method of claim 5 wherein $R^2$ represents:
-phenyl, optionally substituted by one or two fluorine, methoxy, —CON(H)(Me), —NHCOMe or cyano groups;
-phenyl-pyrrolidinyl, optionally substituted by one or two =O or fluorine groups;
unsubstituted-piperidinyl-CO-morpholinyl;
-2-pyridinyl or -2-pyrazinyl, optionally substituted by CON(H)(Me); or
-2-pyridinyl-N-pyrrolidinyl, wherein said pyrrolidinyl group is optionally substituted by an =O group.

7. The method of claim 6 wherein $R^2$ represents 4-methylaminocarbonylpyridin-2-yl.

8. The method of claim 1 wherein X represents a bond or —$CH_2$—.

9. The method of claim 8 wherein X represents a bond.

10. The method of claim 1 wherein Y represents a bond, CO, $SO_2$ or —CO—CH=CH—.

11. The method of claim 10 wherein Y represents a bond.

12. The method of claim 1 wherein $R^4$ represents hydrogen, $C_{1-6}$ alkyl, —$C_{1-6}$ alkyl-$C_{3-8}$ cycloalkyl, aryl, heterocyclyl or heteroaryl, optionally substituted by a halogen or $C_{1-6}$ alkoxy group.

13. The method of claim 1 wherein $R^5$ and $R^6$ independently represent hydrogen, $C_{1-6}$ alkyl, —$C_{3-8}$ cycloalkyl, —$C_{1-6}$ alkyl-$C_{3-8}$ cycloalkyl, aryl or heterocyclyl, optionally substituted by a halogen, cyano or $C_{1-6}$ alkoxy group;
or —$NR^5R^6$ represents a nitrogen containing heterocyclyl group, optionally substituted by one or two =O groups.

14. The method of claim 13 wherein $R^5$ and $R^6$ independently represent hydrogen, $C_{1-6}$ alkyl, —$C_{3-8}$ cycloalkyl or —$C_{1-6}$ alkyl-$C_{3-8}$ cycloalkyl.

15. The method of claim 1 wherein n represents 0 or 1.

16. The method of claim 15 wherein n represents 1 and $R^3$ represents a halogen atom or a cyano group.

17. The method of claim 15 wherein n represents 0.

18. The method of claim 1 wherein said compound is selected from the group consisting of:

- 7-Benzyloxy-3-cyclobutyl-2,3,4,5-tetrahydro-1H-benzo[d]azepine;
- 7-Benzyloxy-3-cyclopentyl-2,3,4,5-tetrahydro-1H-benzo[d]azepine;
- 3-Cyclobutyl-2,3,4,5-tetrahydro-1H-benzo[d]azepin-7-ol;
- 3-Cyclopentyl-2,3,4,5-tetrahydro-1H-benzo[d]azepin-7-ol;
- 4-(3-Cyclopentyl-2,3,4,5-tetrahydro-1H-benzo azepin-7-yloxy)-piperidine-1-carboxylic acid-tert-butyl ester;
- 3-Cyclopentyl-7-(piperidin-4-yloxy)-2,3,4,5-tetrahydro-1H-benzo[d]azepine;
- 3-Cyclobutyl-7-(piperidin-4-yloxy)-2,3,4,5-tetrahydro-1H-benzo[d]azepine;
- 3-Cyclobutyl-7-(piperidin-4-ylmethoxy)-2,3,4,5-tetrahydro-1H-benzo[d]azepine;
- 3-Cyclobutyl-7-((R)-1-pyrrolidin-2-ylmethoxy)-2,3,4,5-tetrahydro-1H-benzo[d]azepine;
- 3-Cyclobutyl-7-((R)-pyrrolidin-3-yloxy)-2,3,4,5-tetrahydro-1H-benzo[d]azepine;
- 3-Cyclobutyl-7-((S)-pyrrolidin-3-yloxy)-2,3,4,5-tetrahydro-1H-benzo[d]azepine;
- 3-Cyclobutyl-7-((S)-1-pyrrolidin-2-ylmethoxy)-2,3,4,5-tetrahydro-1H-benzo[d]azepine;
- 3-Cyclopentyl-7-(piperidin-4-ylmethoxy)-2,3,4,5-tetrahydro-1H-benzo[d]azepine;
- 4-{1-[4-(3-Cyclobutyl-2,3,4,5-tetrahydro-1H-benzo[d]azepin-7-yloxy)-piperidin-1-yl]-methanoyl}-benzonitrile;
- 1-[4-(3-Cyclobutyl-2,3,4,5-tetrahydro-1H-benzo[d]azepin-7-yloxy)-piperidin-1-yl]-1-(tetrahydro-pyran-4-yl)-methanone;
- 1-[4-(3-Cyclobutyl-2,3,4,5-tetrahydro-1H-benzo[d]azepin-7-yloxy)-piperidin-1-yl]-1-cyclohexyl-methanone;
- 1-[4-(3-Cyclobutyl-2,3,4,5-tetrahydro-1H-benzo[d]azepin-7-yloxy)-piperidin-1-yl]-1-isoquinolin-1-yl-methanone;
- 4-{(E)-3-[4-(3-Cyclobutyl-2,3,4,5-tetrahydro-1H-benzo[d]azepin-7-yloxy)-piperidin-1-yl]-3-oxo-propenyl}-benzonitrile;
- 1-[4-(3-Cyclobutyl-2,3,4,5-tetrahydro-1H-benzo[d]azepin-7-yloxy)-piperidin-1-yl]-1-isoquinolin-6-yl-methanone;
- 1-[4-(3-Cyclobutyl-2,3,4,5-tetrahydro-1H-benzo[d]azepin-7-yloxy)-piperidin-1-yl]-1-(5-methyl-isoxazol-3-yl)-methanone;
- 1-Benzothiazol-6-yl-1-[4-(3-cyclobutyl-2,3,4,5-tetrahydro-1H-benzo[d]azepin-7-yloxy)-piperidin-1-yl]-methanone;
- 1-[4-(3-Cyclobutyl-2,3,4,5-tetrahydro-1H-benzo[d]azepin-7-yloxy)-piperidin-1-yl]-1-pyridin-4-yl-methanone;
- 1-[4-(3-Cyclobutyl-2,3,4,5-tetrahydro-1H-benzo[d]azepin-7-yloxy)-piperidin-1-yl]-1-[4-(1-pyrrolidin-1-yl-methanoyl)-phenyl]-methanone;
- 1-[4-(3-Cyclobutyl-2,3,4,5-tetrahydro-1H-benzo[d]azepin-7-yloxy)-piperidin-1-yl]-1-thiophen-3-yl-methanone;
- 1-[4-(3-Cyclobutyl-2,3,4,5-tetrahydro-1H-benzo[d]azepin-7-yloxy)-piperidin-1-yl]-1-furan-3-yl-methanone;
- 1-[4-(3-Cyclobutyl-2,3,4,5-tetrahydro-1H-benzo[d]azepin-7-yloxymethyl)-piperidin-1-yl]-1-tetrahydro-pyran-4-yl)-methanone;
- 1-[(R)-2-(3-Cyclobutyl-2,3,4,5-tetrahydro-1H-benzo[d]azepin-7-yloxymethyl)-pyrrolidin-1-yl]-1-(tetrahydro-pyran-4-yl)-methanone;
- 1-[(R)-3-(3-Cyclobutyl-2,3,4,5-tetrahydro-1H-benzo[d]azepin-7-yloxy)-pyrrolidin-1-yl]-1-(tetrahydro-pyran-4-yl)-methanone;
- 1-[(S)-3-(3-Cyclobutyl-2,3,4,5-tetrahydro-1H-benzo[d]azepin-7-yloxy)-pyrrolidin-1-yl]-1-(tetrahydro-pyran-4-yl)-methanone;
- 1-[(S)-2-(3-Cyclobutyl-2,3,4,5-tetrahydro-1H-benzo azepin-7-yloxy)-pyrrolidin-1-yl]-1-(tetrahydro-pyran-4-yl)-methanone;
- 1-[4-(3-Cyclobutyl-2,3,4,5-tetrahydro-1H-benzo[d]azepin-7-yloxy)-piperidin-1-yl]-1-(methanesulfonyl-phenyl)-methanone;
- 1-[4-(3-Cyclobutyl-2,3,4,5-tetrahydro-1H-benzo[d]azepin-7-yloxy)-piperidin-1-yl]-1-pyrazin-2-yl-methanone;
- 5-{1-[4-(3-Cyclobutyl-2,3,4,5-tetrahydro-1H-benzo[d]azepin-7-yloxy)-piperidin-1-yl]-methanoyl}-1H-pyridone;
- 1-[4-(3-Cyclobutyl-2,3,4,5-tetrahydro-1H-benzo[d]azepin-7-yloxy)-piperidin-1-yl]-1-(2,3-dihydro-benzofuran-5-yl)-methanone;
- 1-[4-(3-Cyclobutyl-2,3,4,5-tetrahydro-1H-benzo[d]azepin-7-yloxy)-piperidin-1-yl]-3-methoxy-propan-1-one;
- 1-[4-(3-Cyclobutyl-2,3,4,5-tetrahydro-1H-benzo[d]azepin-7-yloxy)-piperidin-1-yl]-(2,3-dihydro-benzofuran-7-yl)-methanone;
- 4-{1-[4-(3-Cyclopentyl-7-(piperidin-4-ylmethoxy)-2,3,4,5-tetrahydro-1H-benzo[d]azepin-7-yloxymethyl)piperidin-1-yl]-methanoyl}-benzonitrile;
- 1-[4-(3-Cyclopentyl-2,3,4,5-tetrahydro-1H-benzo[d]azepin-7-yloxymethyl)-piperidin-1-yl]-1-[4-(1-pyrrolidin-1-yl-methanoyl)-phenyl]-methanone;
- 4-{1-[4-(3-Cyclopentyl-2,3,4,5-tetrahydro-1H-benzo[d]azepin-7-yloxy)-piperidin-1-yl]-methanoyl}-benzonitrile;
- 1-[4-(3-Cyclopentyl-2,3,4,5-tetrahydro-1H-benzo[d]azepin-7-yloxy)-piperidin-1-yl]-1-pyridin-4-yl-methanone;
- 1-[4-(3-Cyclopentyl-2,3,4,5-tetrahydro-1H-benzo[d]azepin-7-yloxy)-piperidin-1-yl]-1-quinolin-6-yl-methanone;
- 1-[4-(3-Cyclopentyl-2,3,4,5-tetrahydro-1H-benzo[d]azepin-7-yloxy)-piperidin-1-yl]-1-[4-(1-pyrrolidin-1-yl-methanoyl)-phenyl]methanone;
- 1-Biphenyl-4-yl-1-[4-(3-cyclopentyl-2,3,4,5-tetrahydro-1H-benzo[d]azepin-7-yloxy)-piperidin-1-yl]-methanone;
- 1-[4-(3-Cyclobutyl-2,3,4,5-tetrahydro-1H-benzo[d]azepin-7-yloxy)-piperidin-1-yl]-1-cyclopentyl-methanone;
- 4-{1-[4-(3-Cyclobutyl-2,3,4,5-tetrahydro-1H-benzo[d]azepin-7-yloxymethyl)-piperidin-1-yl]-methanoyl}-benzonitrile;
- 4-{1-[(R)-2-(3-Cyclobutyl-2,3,4,5-tetrahydro-1H-benzo[d]azepin-7-yloxymethyl)-pyrrolidin-1-yl]-methanoyl}-benzonitrile;
- 4-{1-[(R)-3-(3-Cyclobutyl-2,3,4,5-tetrahydro-1H-benzo[d]azepin-7-yloxy)-pyrrolidin-1-yl]-methanoyl}-benzonitrile;
- 4-{1-[(S)-3-(3-Cyclobutyl-2,3,4,5-tetrahydro-1H-benzo[d]azepin-7-yloxy)-pyrrolidin-1-yl]-methanoyl}-benzonitrile;

4-{1-[(S)-2-(3-Cyclobutyl-2,3,4,5-tetrahydro-1H-benzo[d]azepin-7-yloxy)-pyrrolidin-1-yl]-methanoyl}-benzonitrile;
1-[4-(3-Cyclobutyl-2,3,4,5-tetrahydro-1H-benzo[d]azepin-7-yloxy)-piperidin-1-yl]-2,2-dimethyl-propan-1-one;
1-[4-(3-Cyclobutyl-2,3,4,5-tetrahydro-1H-benzo[d]azepin-7-yloxy)-piperidin-1-yl]-1-cyclopropyl-methanone;
1-Cyclobutyl-1-[4-(3-cyclobutyl-2,3,4,5-tetrahydro-1H-benzo[d]azepin-7-yloxy)-piperidine-1-yl]-methanone;
1-[4-(3-Cyclobutyl-2,3,4,5-tetrahydro-1H-benzo[d]azepin-7-yloxy)-piperidin-1-yl]-1-morpholin-4-yl-methanone;
1-[4-(3-Cyclobutyl-2,3,4,5-tetrahydro-1H-benzo[d]azepin-7-yloxymethyl)-piperidin-1-yl]-1-morpholin-4-yl-methanone;
1-[(R)-2-(3-Cyclobutyl-2,3,4,5-tetrahydro-1H-benzo[d]azepin-7-yloxymethyl)-pyrrolidin-1-yl]-1-morpholin-4-yl-methanone;
1-[(R)-3-(3-Cyclobutyl-2,3,4,5-tetrahydro-1H-benzo[d]azepin-7-yloxy)-pyrrolidin-1-yl]-1-morpholin-4-yl-methanone;
1-[(S)-3-(3-Cyclobutyl-2,3,4,5-tetrahydro-1H-benzo[d]azepin-7-yloxy)-pyrrolidin-1-yl]-1-morpholin-4-yl-methanone;
4-(3-Cyclobutyl-2,3,4,5-tetrahydro-1H-benzo[d]azepin-7-yloxy)-piperidine-1-carboxylic acid diisopropylamide;
1-[4-(3-Cyclobutyl-2,3,4,5-tetrahydro-1H-benzo[d]azepin-7-yloxy)-piperidin-1-yl]-pyrrolidin-1-yl-methanone;
1-[4-(3-Cyclobutyl-2,3,4,5-tetrahydro-1H-benzo[d]azepin-7-yloxy)-piperidin-1-yl]-1-piperidin-1-yl-methanone;
1-[(S)-2-(3-Cyclobutyl-2,3,4,5-tetrahydro-1H-benzo[d]azepin-7-yloxymethyl)-pyrrolidin-1-yl]-1-morpholin-4-yl-methanone;
4-(3-Cyclobutyl-2,3,4,5-tetrahydro-1H-benzo[d]azepin-7-yloxy)-piperidine-1-carboxylic acid diethylamide;
1-[4-(3-Cyclobutyl-2,3,4,5-tetrahydro-1H-benzo[d]azepin-7-yloxy)-piperidin-1-yl]-1-(1,3-dihydro-isoindol-2-yl)-methanone;
1-[4-(3-Cyclobutyl-2,3,4,5-tetrahydro-1H-benzo[d]azepin-7-yloxy)-piperidin-1-yl]-1-(2,3,5,6-tetrahydro-[1,2']bipyrazinyl-4-yl)-methanone;
4-(3-Cyclobutyl-2,3,4,5-tetrahydro-1H-benzo[d]azepin-7-yloxy)-piperidine-1-carboxylic acid isopropyl-(2-methoxy-ethyl) amide;
1-[4-(3-Cyclobutyl-2,3,4,5-tetrahydro-1H-benzo[d]azepin-7-yloxy)-piperidin-1-yl]-(1,1-dioxo-thiomorpholin-4-yl)-methanone;
4-(3-Cyclobutyl-2,3,4,5-tetrahydro-1H-benzo[d]azepin-7-yloxy)-piperidine-1-carboxylic acid isopropylamide;
4-(3-Cyclobutyl-2,3,4,5-tetrahydro-1H-benzo[d]azepin-7-yloxy)-piperidine-1-carboxylic acid (4-fluoro-phenyl)-amide;
2-(3-Cyclobutyl-2,3,4,5-tetrahydro-1H-benzo[d]azepin-7-yloxy)-N,N-dimethyl-acetamide;
2-(3-Cyclobutyl-2,3,4,5-tetrahydro-1H-benzo[d]azepin-7-yloxy)-N-phenyl-acetamide;
2-(3-Cyclobutyl-2,3,4,5-tetrahydro-1H-benzo[d]azepin-7-yloxy)-1-pyrrolidin-1-yl-ethanone;
2-(3-Cyclobutyl-2,3,4,5-tetrahydro-1H-benzo[d]azepin-7-yloxy)-1-morpholin-4-yl-ethanone;
3-Cyclobutyl-7-(1-methanesulfonyl-piperidin-4-yloxy)-2,3,4,5-tetrahydro-1H-benzo[d]azepine;
4-[4-(3-Cyclobutyl-2,3,4,5-tetrahydro-1H-benzo[d]azepin-7-yloxy)-piperidine-1-sulfonyl]-benzonitrile;
3-Cyclobutyl-7-[1-(3,5-dimethyl-isoxazole-4-sulfonyl)-piperidin-4-yloxy]-2,3,4,5-tetrahydro-1H-benzo[d]azepine;
4-[4-(3-Cyclobutyl-2,3,4,5-tetrahydro-1H-benzo[d]azepin-7-yloxymethyl)-piperidine-1-sulfonyl]-benzonitrile;
4-[(R)-2-(3-Cyclobutyl-2,3,4,5-tetrahydro-1H-benzo[d]azepin-7-yloxymethyl)-pyrrolidine-1-sulfonyl]-benzonitrile;
4-[(R)-3-(3-Cyclobutyl-2,3,4,5-tetrahydro-1H-benzo[d]azepin-7-yloxy)-pyrrolidine-1-sulfonyl]-benzonitrile;
4-[(S)-3-(3-Cyclobutyl-2,3,4,5-tetrahydro-1H-benzo[d]azepin-7-yloxy)-pyrrolidine-1-sulfonyl]-benzonitrile;
3-Cyclobutyl-7-(2,4-difluoro-benzyloxy)-2,3,4,5-tetrahydro-1H-benzo[d]azepine;
3-(3-Cyclobutyl-2,3,4,5-tetrahydro-1H-benzo[d]azepin-7-yloxymethyl)-benzonitrile;
3-Cyclobutyl-7-(3-methoxy-benzyloxy)-2,3,4,5-tetrahydro-1H-benzo[d]azepine;
3-Cyclobutyl-7-(pyridin-2-ylmethoxy)-2,3,4,5-tetrahydro-1H-benzo[d]azepine;
3-Cyclobutyl-7-(pyridin-3-ylmethoxy)-2,3,4,5-tetrahydro-1H-benzo[d]azepine;
3-Cyclobutyl-7-(pyridin-4-ylmethoxy)-2,3,4,5-tetrahydro-1H-benzo[d]azepine;
2-(3-Cyclobutyl-2,3,4,5-tetrahydro-1H-benzo[d]azepin-7-yloxymethyl)-benzonitrile;
4-(3-Cyclobutyl-2,3,4,5-tetrahydro-1H-benzo[d]azepin-7-yloxymethyl)-benzonitrile;
6-(3-Cyclobutyl-2,3,4,5-tetrahydro-1H-benzo[d]azepin-7-yloxy methyl)-1-methyl-1H-quinolin-2-one;
4-(3-Cyclopentyl-2,3,4,5-tetrahydro-1H-benzo[d]azepin-7-yloxymethyl)-benzoic acid methyl ester;
4-(3-Cyclopentyl-2,3,4,5-tetrahydro-1H-benzo[d]azepin-7-yloxymethyl)-benzoic acid;
1-[4-(3-Cyclopentyl-2,3,4,5-tetrahydro-1H-benzo[d]azepin-7-yloxymethyl)-phenyl]-1-pyrrolidin-yl-methanone;
1-[4-(3-Cyclopentyl-2,3,4,5-tetrahydro-1H-benzo azepin-7-yloxymethyl)-phenyl]-1-morpholin-4-yl-methanone;
1-[4-(3-Cyclopentyl-2,3,4,5-tetrahydro-1H-benzo[d]azepin-7-yloxymethyl)-phenyl]-1-(4-pyridin-4-yl-piperazin-1-yl)-methanone;
1-[4-(3-Cyclopentyl-2,3,4,5-tetrahydro-1H-benzo[d]azepin-7-yloxymethyl)-phenyl]-1-[4-(4-fluoro-phenyl)-piperazin-1-yl]-methanone;
3-(3-Cyclopentyl-2,3,4,5-tetrahydro-1H-benzo[d]azepin-7-yloxymethyl)-benzoic acid methyl ester;
3-(3-Cyclopentyl-2,3,4,5-tetrahydro-1H-benzo[d]azepin-7-yloxy methyl)-benzoic acid;
1-[3-(3-Cyclopentyl-2,3,4,5-tetrahydro-1H-benzo[d]azepin-7-yloxymethyl)-phenyl]-1-pyrrolidin-yl-methanone;
1-[3-(3-Cyclopentyl-2,3,4,5-tetrahydro-1H-benzo[d]azepin-7-yloxymethyl)-phenyl]-1-morpholin-4-yl-methanone;
1-[3-(3-Cyclopentyl-2,3,4,5-tetrahydro-1H-benzo[d]azepin-7-yloxymethyl)-phenyl]-1-(4-pyridin-4-yl-piperazin-1-yl)-methanone;
1-[3-(3-Cyclopentyl-2,3,4,5-tetrahydro-1H-benzo[d]azepin-7-yloxymethyl)-phenyl]-1-[4-(4-fluoro-phenyl)-piperazin-1-yl]-methanone;
6-(3-Cyclobutyl-2,3,4,5-tetrahydro-1H-benzo[d]azepin-7-yloxy)-nicotinonitrile;

3-Cyclobutyl-7-(pyridin-2-yloxy)-2,3,4,5-tetrahydro-1H-benzo[d]azepine;
1-[6-(3-Cyclobutyl-2,3,4,5-tetrahydro-1H-benzo[d]azepin-7-yloxy)-pyridin-3-yl]-1-morpholin-4-yl-methanone;
1-[6-(3-Cyclobutyl-2,3,4,5-tetrahydro-1H-benzo[d]azepin-7-yloxy)-pyridin-3-yl]-1-pyrrolidin-1-1-methanone;
6-(3-Cyclobutyl-2,3,4,5-tetrahydro-1H-benzo[d]azepin-7-yloxy)-nicotinamide;
6-(3-Cyclobutyl-2,3,4,5-tetrahydro-1H-benzo[d]azepin-7-yloxy)-N,N-dimethyl-nicotinamide;
6-(3-Cyclobutyl-2,3,4,5-tetrahydro-1H-benzo[d]azepin-7-yloxy)-N-ethyl-N-methyl-nicotinamide;
6-(3-Cyclobutyl-2,3,4,5-tetrahydro-1H-benzo[d]azepin-7-yloxy)-N-cyclopentyl-nicotinamide;
1-[6-(3-Cyclobutyl-2,3,4,5-tetrahydro-1H-benzo[d]azepin-7-yloxy)-pyridin-3-yl]-1-piperidin-1-yl-methanone;
1-[2-(3-Cyclobutyl-2,3,4,5-tetrahydro-1H-benzo azepin-7-yloxy)-pyridin-4-yl]-1-piperidin-1-yl-methanone;
1-[2-(3-Cyclobutyl-2,3,4,5-tetrahydro-1H-benzo[d]azepin-7-yloxy)-pyridin-4-yl]-1-pyrrolidin-1-yl-methanone;
1-[2-(3-Cyclobutyl-2,3,4,5-tetrahydro-1H-benzo[d]azepin-7-yloxy)-pyridin-4-yl]-1-morpholin-4-yl-methanone;
1-[6-(3-Cyclobutyl-2,3,4,5-tetrahydro-1H-benzo[d]azepin-7-yloxy)-pyridin-2-yl]-1-piperidin-1-yl-methanone;
1-[6-(3-Cyclobutyl-2,3,4,5-tetrahydro-1H-benzo[d]azepin-7-yloxy)-pyridin-2-yl]-1-(1,1-dioxothiomorpholin-4-yl)-methanone;
1-[6-(3-Cyclobutyl-2,3,4,5-tetrahydro-1H-benzo[d]azepin-7-yloxy)-pyridin-2-yl]-1-pyrrolidin-1-yl-methanone;
1-[6-(3-Cyclobutyl-2,3,4,5-tetrahydro-1H-benzo[d]azepin-7-yloxy)-pyridin-2-yl]-1-morpholin-4-yl-methanone;
1-[2-(3-Cyclobutyl-2,3,4,5-tetrahydro-1H-benzo[d]azepin-7-yloxy)-pyridin-3-yl]-1-morpholin-4-yl-methanone;
1-[2-(3-Cyclobutyl-2,3,4,5-tetrahydro-1H-benzo[d]azepin-7-yloxy)-pyridin-3-yl]-1-piperidin-1-yl-methanone;
3-Cyclobutyl-7-(pyrazin-2-yloxy)-2,3,4,5-tetrahydro-1H-benzo[d]azepine;
3-Cyclobutyl-7-(pyrimidin-2-yloxy)-2,3,4,5-tetrahydro-1H-benzo[d]azepine;
7-(5-Bromo-pyrimidin-2-yloxy)-3-Cyclobutyl-2,3,4,5-tetrahydro-1H-benzo[d]azepine;
6-(3-Cyclobutyl-2,3,4,5-tetrahydro-1H-benzo[d]azepin-7-yloxy)-N-methyl-nicotinamide;
5-(3-Cyclobutyl-2,3,4,5-tetrahydro-1H-benzo[d]azepin-7-yloxy)-pyrazine-2-carboxylic acid methyl ester;
5-(3-Cyclobutyl-2,3,4,5-tetrahydro-1H-benzo[d]azepin-7-yloxy)-pyrazine-2-carboxylic acid;
1-[5-(3-Cyclobutyl-2,3,4,5-tetrahydro-1H-benzo[d]azepin-7-yloxy)-pyrazin-2-yl]-1-morpholin-4-yl-methanone;
5-(3-Cyclobutyl-2,3,4,5-tetrahydro-1H-benzo[d]azepin-7-yloxy)-pyrazine-2-carboxylic acid ethylmethyl amide;
1-[5-(3-Cyclobutyl-2,3,4,5-tetrahydro-1H-benzo[d]azepin-7-yloxy)-pyrazin-2-yl]-1-piperidin-4-yl-methanone;
1-[5-(3-Cyclobutyl-2,3,4,5-tetrahydro-1H-benzo[d]azepin-7-yloxy)-pyrazin-2-yl]-1-pyrrolidin-4-yl-methanone;
5-(3-Cyclobutyl-2,3,4,5-tetrahydro-1H-benzo[d]azepin-7-yloxy)-pyrazine-2-carboxylic acid methyl amide;
3-Cyclobutyl-7-phenoxy-2,3,4,5-tetrahydro-1H-benzo[d]azepine;
1-[4-(3-Cyclobutyl-2,3,4,5-tetrahydro-1H-benzo[d]azepin-7-yloxy)-phenyl]-1-morpholin-4-yl-methanone;
4-(3-Cyclobutyl-2,3,4,5-tetrahydro-1H-benzo[d]azepin-7-yloxy)-N-cyclopropylmethyl-benzamide;
1-[4-(3-Cyclobutyl-2,3,4,5-tetrahydro-1H-benzo[d]azepin-7-yloxy)-phenyl]-1-pyrrolidin-1-yl-methanone;
N-Cyclobutyl-4-(3-Cyclobutyl-2,3,4,5-tetrahydro-1H-benzo[d]azepin-7-yloxy)-benzamide;
4-(3-Cyclobutyl-2,3,4,5-tetrahydro-1H-benzo[d]azepin-7-yloxy)-N,N-diethyl-benzamide;
N-(2-Cyano-ethyl)-4-(3-cyclobutyl-2,3,4,5-tetrahydro-1H-benzo[d]azepin-7-yloxy)-N-methyl-benzamide;
1-[3-(3-Cyclobutyl-2,3,4,5-tetrahydro-1H-benzo[d]azepin-7-yloxy)-phenyl]-1-morpholin-4-yl-methanone;
3-(3-Cyclobutyl-2,3,4,5-tetrahydro-1H-benzo[d]azepin-7-yloxy)-N-cyclopropylmethyl-benzamide;
3-Cyclobutyl-7-[4-(morpholine-4-sulfonyl)-phenoxy]-2,3,4,5-tetrahydro-1H-benzo[d]azepine;
4-(3-Cyclobutyl-2,3,4,5-tetrahydro-1H-benzo[d]azepin-7-yloxy)-N,N-diethyl-benzenesulfonamide;
7-Benzyloxy-3-cyclohexyl-2,3,4,5-tetrahydro-1H-benzo[d]azepine;
3-Cyclobutyl-7-{[2-(1-piperidinyl)-5-pyrimidinyl]oxy}-2,3,4,5-tetrahydro-1H-3-benzazepine;
3-Cyclobutyl-7-{[2-(1-pyrrolidinyl)-5-pyrimidinyl]oxy}-2,3,4,5-tetrahydro-1H-3-benzazepine;
3-Cyclobutyl-7-{[2-(1,1-dioxido-4-thiomorpholinyl)-5-pyrimidinyl]oxy}-2,3,4,5-tetrahydro-1H-3-benzazepine;
5-[(3-Cyclobutyl-2,3,4,5-tetrahydro-1H-3-benzazepin-7-yl)oxy]-N-methyl-2-pyrimidinamine;
3-Cyclobutyl-7-{[2-(methyloxy)-5-pyrimidinyl]oxy}-2,3,4,5-tetrahydro-1H-3-benzazepine;
1-[4-({4-[(3-Cyclobutyl-2,3,4,5-tetrahydro-1H-3-benzazepin-7-yl)oxy]-1-piperidinyl}carbonyl)phenyl]-2-pyrrolidinone;
3-Cyclobutyl-7-[(1-{[3-(methylsulfonyl)phenyl]carbonyl}-4-piperidinyl)oxy]-2,3,4,5-tetrahydro-1H-3-benzazepine;
3-Cyclobutyl-7-({1-[(1,1-dioxido-3,4-dihydro-2H-1-benzothiopyran-6-yl)carbonyl]-4-piperidinyl}oxy)-2,3,4,5-tetrahydro-1H-3-benzazepine;
3-Cyclobutyl-7-{[(3S)-3-pyrrolidinylmethyl]oxy}-2,3,4,5-tetrahydro-1H-3-benzazepine;
3-Cyclobutyl-7-{[(3S)-3-piperidinylmethyl]oxy}-2,3,4,5-tetrahydro-1H-3-benzazepine;
3-Cyclobutyl-7-[(3S)-3-piperidinyloxy]-2,3,4,5-tetrahydro-1H-3-benzazepine;
3-Cyclobutyl-7-({[(3S)-1-(4-morpholinylcarbonyl)-3-piperidinyl]methyl}oxy)-2,3,4,5-tetrahydro-1H-3-benzazepine;
3-Cyclobutyl-7-({[(3S)-1-(4-morpholinylcarbonyl)-3-pyrrolidinyl]methyl}oxy)-2,3,4,5-tetrahydro-1H-3-benzazepine;
3-Cyclobutyl-7-{[(3S)-1-(4-morpholinyl carbonyl)-3-piperidinyl]oxy}-2,3,4,5-tetrahydro-1H-3-benzazepine;

4-[((3S)-3-{[(3-Cyclobutyl-2,3,4,5-tetrahydro-1H-3-benzazepin-7-yl)oxy]methyl}-1-piperidinyl)carbonyl]benzonitrile;

4-[((3S)-3-{[(3-Cyclobutyl-2,3,4,5-tetrahydro-1H-3-benzazepin-7-yl) oxy]methyl}-1-pyrrolidinyl)carbonyl]benzonitrile;

4-({(3S)-3-[(3-Cyclobutyl-2,3,4,5-tetrahydro-1H-3-benzazepin-7-yl)oxy]-1-piperidinyl}carbonyl)benzonitrile;

3-Cyclobutyl-7-({[(3S)-1-(tetrahydro-2H-pyran-4-ylcarbonyl)-3-pyrrolidinyl]methyl}oxy)-2,3,4,5-tetrahydro-1H-3-benzazepine;

3-Cyclobutyl-7-({[(3S)-1-(tetrahydro-2H-pyran-4-ylcarbonyl)-3-piperidinyl]methyl}oxy)-2,3,4,5-tetrahydro-1H-3-benzazepine;

3-Cyclobutyl-7-{[(3S)-1-(tetrahydro-2H-pyran-4-ylcarbonyl)-3-piperidinyl]oxy}-2,3,4,5-tetrahydro-1H-3-benzazepine;

6-{4-[(3-Cyclobutyl-2,3,4,5-tetrahydro-1H-3-benzazepin-7-yl)oxy]-1-piperidinyl}-3-pyridinecarbonitrile;

6-{4-[(3-Cyclobutyl-2,3,4,5-tetrahydro-1H-3-benzazepin-7-yl)oxy]-1-piperidinyl}-N-(cyclopropylmethyl)-3-pyridinecarboxamide;

7-({1-[5-(1-Azetidinylcarbonyl)-2-pyridinyl]-4-piperidinyl}oxy)-3-cyclobutyl-2,3,4,5-tetrahydro-1H-3-benzazepine;

3-Cyclobutyl-7-({1-[5-(4-morpholinylcarbonyl)-2-pyridinyl]-4-piperidinyl}oxy)-2,3,4,5-tetrahydro-1H-3-benzazepine;

6-{4-[(3-Cyclobutyl-2,3,4,5-tetrahydro-1H-3-benzazepin-7-yl)oxy]-1-piperidinyl}-N-methyl-3-pyridinecarboxamide;

2-{4-[(3-Cyclobutyl-2,3,4,5-tetrahydro-1H-3-benzazepin-7-yl)oxy]-1-piperidinyl}-4-pyridinecarbonitrile;

3-Cyclobutyl-7-{[1-(2-pyrazinyl)-4-piperidinyl]oxy}-2,3,4,5-tetrahydro-1H-3-benzazepine;

Ethyl 4-[(3-cyclobutyl-2,3,4,5-tetrahydro-1H-3-benzazepin-7-yl)oxy]butanoate;

4-[(3-Cyclobutyl-2,3,4,5-tetrahydro-1H-3-benzazepin-7-yl)oxy]butanoic acid;

3-Cyclobutyl-7-{[4-oxo-4-(1-piperidinyl)butyl]oxy}-2,3,4,5-tetrahydro-1H-3-benzazepine;

3-Cyclobutyl-7-{[4-oxo-4-(1-pyrrolidinyl)butyl]oxy}-2,3,4,5-tetrahydro-1H-3-benzazepine;

4-[(3-Cyclobutyl-2,3,4,5-tetrahydro-1H-3-benzazepin-7-yl)oxy]-N-cyclopentylbutanamide;

4-[(3-Cyclobutyl-2,3,4,5-tetrahydro-1H-3-benzazepin-7-yl)oxy]-N-methylbutanamide;

5-[(3-Cyclobutyl-2,3,4,5-tetrahydro-1H-3-benzazepin-7-yl)oxy]-N-(1-methylethyl)-2-pyrazinecarboxamide;

5-[(3-Cyclobutyl-2,3,4,5-tetrahydro-1H-3-benzazepin-7-yl)oxy]-N-(tetrahydro-2H-pyran-4-yl)-2-pyrazinecarboxamide;

7-{[5-(1-Azetidinylcarbonyl)-2-pyrazinyl]oxy}-3-cyclobutyl-2,3,4,5-tetrahydro-1H-3-benzazepine;

5-[(3-Cyclobutyl-2,3,4,5-tetrahydro-1H-3-benzazepin-7-yl)oxy]-N,N-diethyl-2-pyrazinecarboxamide;

5-[(3-Cyclobutyl-2,3,4,5-tetrahydro-1H-3-benzazepin-7-yl)oxy]-N-[2-(methyloxy)ethyl]-2-pyrazinecarboxamide;

5-[(3-Cyclobutyl-2,3,4,5-tetrahydro-1H-3-benzazepin-7-yl)oxy]-N-ethyl-2-pyrazinecarboxamide;

5-[(3-Cyclobutyl-2,3,4,5-tetrahydro-1H-3-benzazepin-7-yl)oxy]-2-pyrimidinecarbonitrile;

5-[(3-Cyclobutyl-2,3,4,5-tetrahydro-1H-3-benzazepin-7-yl)oxy]-2-pyrimidinecarboxylic acid;

3-Cyclobutyl-7-{[2-(4-morpholinylcarbonyl)-5-pyrimidinyl]oxy}-2,3,4,5-tetrahydro-1H-3-benzazepine;

5-[(3-Cyclobutyl-2,3,4,5-tetrahydro-1H-3-benzazepin-7-yl)oxy]-N-(cyclopropylmethyl)-2-pyrimidinecarboxamide;

5-[(3-Cyclobutyl-2,3,4,5-tetrahydro-1H-3-benzazepin-7-yl)oxy]-N-ethyl-2-pyrimidinecarboxamide;

7-{[2-(1-Azetidinylcarbonyl)-5-pyrimidinyl]oxy}-3-cyclobutyl-2,3,4,5-tetrahydro-1H-3-benzazepine;

5-[(3-Cyclobutyl-2,3,4,5-tetrahydro-1H-3-benzazepin-7-yl)oxy]-N-ethyl-N-methyl-2-pyrimidinecarboxamide;

N-Cyclobutyl-5-[(3-cyclobutyl-2,3,4,5-tetrahydro-1H-3-benzazepin-7-yl)oxy]-2-pyrimidinecarboxamide;

5-[(3-Cyclobutyl-2,3,4,5-tetrahydro-1H-3-benzazepin-7-yl)oxy]-N-(tetrahydro-2H-pyran-4-yl)-2-pyrimidinecarboxamide;

3-Cyclobutyl-7-[2-(1-pyrrolidinylcarbonyl)-5-pyrimidinyl]oxy-2,3,4,5-tetrahydro-1H-3-benzazepine;

3-Cyclobutyl-7-{[2-(1-piperidinylcarbonyl)-5-pyrimidinyl]oxy}-2,3,4,5-tetrahydro-1H-3-benzazepine;

5-[(3-Cyclobutyl-2,3,4,5-tetrahydro-1H-3-benzazepin-7-yl)oxy]-N-methyl-2-pyrimidinecarboxamide;

5-[(3-Cyclobutyl-2,3,4,5-tetrahydro-1H-3-benzazepin-7-yl)oxy]-2-pyridinecarboxylic acid;

5-[(3-Cyclobutyl-2,3,4,5-tetrahydro-1H-3-benzazepin-7-yl)oxy]-N-methyl-2-pyridinecarboxamide;

5-[(3-Cyclobutyl-2,3,4,5-tetrahydro-1H-3-benzazepin-7-yl)oxy]-N-ethyl-2-pyridinecarboxamide;

5-[(3-Cyclobutyl-2,3,4,5-tetrahydro-1H-3-benzazepin-7-yl)oxy]-N-ethyl-N-methyl-2-pyridinecarboxamide;

5-[(3-Cyclobutyl-2,3,4,5-tetrahydro-1H-3-benzazepin-7-yl)oxy]-N,N-diethyl-2-pyridinecarboxamide;

5-[(3-Cyclobutyl-2,3,4,5-tetrahydro-1H-3-benzazepin-7-yl)oxy]-N-ethyl-N-[2-(methyloxy)ethyl]-2-pyridinecarboxamide;

3-Cyclobutyl-7-{[6-(1-pyrrolidinylcarbonyl)-3-pyridinyl]oxy}-2,3,4,5-tetrahydro-1H-3-benzazepine;

3-Cyclobutyl-7-{[6-(4-morpholinylcarbonyl)-3-pyridinyl]oxy}-2,3,4,5-tetrahydro-1H-3-benzazepine;

3-Cyclobutyl-7-{[6-(tetrahydro-1,4-oxazepin-4(5H)-ylcarbonyl)-3-pyridinyl]oxy}-2,3,4,5-tetrahydro-1H-3-benzazepine;

5-[(3-Cyclobutyl-2,3,4,5-tetrahydro-1H-3-benzazepin-7-yl)oxy]-N-cyclopentyl-2-pyridinecarboxamide;

6-[(3-Cyclobutyl-2,3,4,5-tetrahydro-1H-3-benzazepin-7-yl)oxy]-3-pyridinecarboxylic acid methyl ester;

6-[(3-Cyclobutyl-2,3,4,5-tetrahydro-1H-3-benzazepin-7-yl)oxy]-3-pyridinecarboxylic acid;

6-[(3-Cyclobutyl-2,3,4,5-tetrahydro-1H-3-benzazepin-7-yl)oxy]-N-cyclopropyl-3-pyridinecarboxamide;

6-[(3-Cyclobutyl-2,3,4,5-tetrahydro-1H-3-benzazepin-7-yl)oxy]-N-(1-methylethyl)-3-pyridinecarboxamide;

6-[(3-Cyclobutyl-2,3,4,5-tetrahydro-1H-3-benzazepin-7-yl)oxy]-N-ethyl-3-pyridinecarboxamide;

N-Cyclobutyl-6-[(3-cyclobutyl-2,3,4,5-tetrahydro-1H-3-benzazepin-7-yl)oxy]-3-pyridinecarboxamide;

6-[(3-Cyclobutyl-2,3,4,5-tetrahydro-1H-3-benzazepin-7-yl)oxy]-N-(tetrahydro-2H-pyran-4-yl)-3-pyridinecarboxamide;

6-[(3-Cyclobutyl-2,3,4,5-tetrahydro-1H-3-benzazepin-7-yl)oxy]-N,N-diethyl-3-pyridinecarboxamide;

6-[(3-Cyclobutyl-2,3,4,5-tetrahydro-1H-3-benzazepin-7-yl)oxy]-N-[2-(methyloxy)ethyl]-3-pyridinecarboxamide;

4-[(3-Cyclobutyl-2,3,4,5-tetrahydro-1H-3-benzazepin-7-yl)oxy]-N-ethyl-N-[2-(methyloxy)ethyl]benzamide;

4-[(3-Cyclobutyl-2,3,4,5-tetrahydro-1H-3-benzazepin-7-yl)oxy]-N-methylbenzamide;
3-Cyclobutyl-7-(3-pyridinyloxy)-2,3,4,5-tetrahydro-1H-3-benzazepine;
5-[(3-Cyclobutyl-2,3,4,5-tetrahydro-1H-3-benzazepin-7-yl)oxy]-2-pyridinecarbonitrile;
3-Cyclobutyl-7-[(5-iodo-2-pyridinyl)oxy]-2,3,4,5-tetrahydro-1H-3-benzazepine;
3-Cyclobutyl-7-[(5-nitro-2-pyridinyl)oxy]-2,3,4,5-tetrahydro-1H-3-benzazepine;
N-{6-[(3-Cyclobutyl-2,3,4,5-tetrahydro-1H-3-benzazepin-7-yl)oxy]-3-pyridinyl}acetamide;
3-Cyclobutyl-7-[(5-nitro-1,3-thiazol-2-yl)oxy]-2,3,4,5-tetrahydro-1H-3-benzazepine;
N-{2-[(3-Cyclobutyl-2,3,4,5-tetrahydro-1H-3-benzazepin-7-yl)oxy]-1,3-thiazol-5-yl}acetamide;
3-Cyclobutyl-7-[(5-nitro-2-thienyl)oxy]-2,3,4,5-tetrahydro-1H-3-benzazepine;
N-{5-[(3-Cyclobutyl-2,3,4,5-tetrahydro-1H-3-benzazepin-7-yl)oxy]-2-thienyl}acetamide;
3-Cyclobutyl-7-{[6-(methyloxy)-3-pyridinyl]oxy}-2,3,4,5-tetrahydro-1H-3-benzazepine;
5-[(3-Cyclobutyl-2,3,4,5-tetrahydro-1H-3-benzazepin-7-yl)oxy]-2(1H)-pyridinone;
1-{6-[(3-Cyclobutyl-2,3,4,5-tetrahydro-1H-3-benzazepin-7-yl)oxy]-3-pyridinyl}ethanone;
3-Cyclobutyl-7-{[5-(1H-pyrazol-5-yl)-2-pyridinyl]oxy}-2,3,4,5-tetrahydro-1H-3-benzazepine;
3-Cyclobutyl-7-{[5-(5-methyl-1,3,4-oxadiazol-2-yl)-2-pyridinyl]oxy}-2,3,4,5-tetrahydro-1H-3-benzazepine;
1-{6-[(3-Cyclobutyl-2,3,4,5-tetrahydro-1H-3-benzazepin-7-yl)oxy]-3-pyridinyl}-2-piperidinone;
1-{6-[(3-Cyclobutyl-2,3,4,5-tetrahydro-1H-3-benzazepin-7-yl)oxy]-3-pyridinyl}-2-azetidinone;
3-{6-[(3-Cyclobutyl-2,3,4,5-tetrahydro-1H-3-benzazepin-7-yl)oxy]-3-pyridinyl}-1,3-oxazolidin-2-one;
3-Cyclobutyl-7-{[5-(1H-pyrazol-1-yl)-2-pyridinyl]oxy}-2,3,4,5-tetrahydro-1H-3-benzazepine;
3-Cyclobutyl-7-{[5-(3,5-dimethyl-4-isoxazolyl)-2-pyridinyl]oxy}-2,3,4,5-tetrahydro-1H-3-benzazepine;
6-[(3-Cyclopentyl-2,3,4,5-tetrahydro-1H-3-benzazepin-7-yl)oxy]-N-methyl-3-pyridinecarboxamide;
N-Methyl-6-{[3-(2-methylcyclopentyl)-2,3,4,5-tetrahydro-1H-3-benzazepin-7-yl]oxy}-3-pyridinecarboxamide;
6-[(3-Cyclobutyl-8-iodo-2,3,4,5-tetrahydro-1H-3-benzazepin-7-yl)oxy]-N-methyl-3-pyridinecarboxamide;
3-Cyclobutyl-7-iodo-8-[(phenylmethyl)oxy]-2,3,4,5-tetrahydro-1H-3-benzazepine;
3-Cyclobutyl-7-{[6-methyl-4-(methyloxy)-2-quinolinyl]oxy}-2,3,4,5-tetrahydro-1H-3-benzazepine;
3-Cyclobutyl-7-{[4-(methyloxy)-1,7-naphthyridin-2-yl]oxy}-2,3,4,5-tetrahydro-1H-3-benzazepine;
3-Cyclobutyl-7-(1,5-naphthyridin-2-yloxy)-2,3,4,5-tetrahydro-1H-3-benzazepine;
N-{7-[(3-Cyclobutyl-2,3,4,5-tetrahydro-1H-3-benzazepin-7-yl)oxy]-6-methyl-1,8-naphthyridin-2-yl}acetamide;
Dimethyl 6-[(3-cyclobutyl-2,3,4,5-tetrahydro-1H-3-benzazepin-7-yl)oxy]-2,3-pyridinedicarboxylate;
Disodium 6-[(3-cyclobutyl-2,3,4,5-tetrahydro-1H-3-benzazepin-7-yl)oxy]-2,3-pyridinedicarboxylate;
2-[(3-Cyclobutyl-2,3,4,5-tetrahydro-1H-3-benzazepin-7-yl)oxy]-5H-pyrrolo[3,4-b]pyridine-5,7(6H)-dione;
2-[(3-Cyclobutyl-2,3,4,5-tetrahydro-1H-3-benzazepin-7-yl)oxy]-7-hydroxy-6,7-dihydro-5H-pyrrolo[3,4-b]pyridin-5-one;
2-[(3-Cyclobutyl-2,3,4,5-tetrahydro-1H-3-benzazepin-7-yl)oxy]-6,7-dihydro-5H-pyrrolo[3,4-b]pyridin-5-one;
6-[(3-Cyclobutyl-2,3,4,5-tetrahydro-1H-3-benzazepin-7-yl)oxy]-3-pyridinamine;
N-{6-[(3-cyclobutyl-2,3,4,5-tetrahydro-1H-3-benzazepin-7-yl)oxy]-3-pyridinyl}-4-morpholinecarboxamide;
N-{6-[(3-cyclobutyl-2,3,4,5-tetrahydro-1H-3-benzazepin-7-yl)oxy]-3-pyridinyl}-1-piperidinecarboxamide;
N-{6-[(3-cyclobutyl-2,3,4,5-tetrahydro-1H-3-benzazepin-7-yl)oxy]-3-pyridinyl}-1-pyrrolidinecarboxamide;
N-[6-(3-Cyclobutyl-2,3,4,5-tetrahydro-1H-benzo[d]azepin-7-yloxy)-pyridin-3-yl]isobutyramide;
Tetrahydro-pyran-4-carboxylic acid [6-(3-cyclobutyl-2,3,4,5-tetrahydro-1H-benzo[d]azepin-7-yloxy)-pyridin-3-yl]-amide;
3-Cyclobutyl-7-[5-(4-methanesulfonyl-phenyl)-pyrazine-2-yloxy]-2,3,4,5-tetrahydro-1H-benzo[d]azepine;
N-{4-[5-(3-Cyclobutyl-2,3,4,5-tetrahydro-1H-benzo[d]azepin-7-yloxy)-pyrazin-2-yl]-phenyl}-acetamide;
3-Cyclobutyl-7-(3,5-dimethyl-pyridin-2-yloxy)-2,3,4,5-tetrahydro-1H-benzo[d]azepine;
3-Cyclobutyl-7-[5-(morpholine-4-sulfonyl)-pyridin-2-yloxy]-2,3,4,5-tetrahydro-1H-benzo[d]azepine;
3-Cyclobutyl-7-(2-methyl-furo[2,3-c]pyridin-7-yloxy)-2,3,4,5-tetrahydro-1H-benzo[d]azepine;
2-(3-Cyclobutyl-2,3,4,5-tetrahydro-1H-benzo[d]azepin-7-yloxy)-4-ethoxy-nicotinonitrile;
6-(3-Cyclobutyl-2,3,4,5-tetrahydro-1H-benzo[d]azepin-7-yloxy)-2-methyl-nicotinonitrile;
1-{6-[(3-Cyclobutyl-2,3,4,5-tetrahydro-1H-3-benzazepin-7-yl)oxy]-3-pyridinyl}-5-methyl-2-pyrrolidinone;
1-{6-[(3-Cyclobutyl-2,3,4,5-tetrahydro-1H-3-benzazepin-7-yl)oxy]-3-pyridinyl}-3-methyl-2-imidazolidine;
(4R)-1-{6-[(3-Cyclobutyl-2,3,4,5-tetrahydro-1H-3-benzazepin-7-yl)oxy]-3-pyridinyl}-4-hydroxy-2-pyrrolidinone;
N-Methyl-6-{[3-(3-methylcyclopentyl)-2,3,4,5-tetrahydro-1H-3-benzazepin-7-yl]oxy}-3-pyridinecarboxamide;
5-[(3-Cyclopentyl-2,3,4,5-tetrahydro-1H-3-benzazepin-7-yl)oxy]-N-methyl-2-pyrazinecarboxamide;
N-Methyl-5-{[3-(3-methylcyclopentyl)-2,3,4,5-tetrahydro-1H-3-benzazepin-7-yl]oxy}-2-pyrazinecarboxamide;
1-{3-[(3-Cyclobutyl-2,3,4,5-tetrahydro-1H-3-benzazepin-7-yl)oxy]-2-pyrazinyl}-2-pyrrolidinone;
7-[(5-Chloro-2-pyrazinyl)oxy]-3-cyclobutyl-2,3,4,5-tetrahydro-1H-3-benzazepine;
1-{5-[(3-Cyclobutyl-2,3,4,5-tetrahydro-1H-3-benzazepin-7-yl)oxy]-2-pyrazinyl}-2-pyrrolidinone;
7-[(5-Bromo-2-pyrazinyl)oxy]-3-cyclobutyl-2,3,4,5-tetrahydro-1H-3-benzazepine;
3-{5-[(3-Cyclobutyl-2,3,4,5-tetrahydro-1H-3-benzazepin-7-yl)oxy]-2-pyrazinyl}-1,3-oxazolidin-2-one;
3-Cyclobutyl-7-[5-(1,1-dioxo-2-isothiazolidin-2-yl)-pyridin-2-yloxy]-2,3,4,5-tetrahydro-1H-3-benzazepine;
1-{6-[(3-Cyclobutyl-2,3,4,5-tetrahydro-1H-3-benzazepin-7-yl)oxy]-3-pyridinyl}-2-imidazolidinone;
5-[(3-Cyclobutyl-2,3,4,5-tetrahydro-1H-3-benzazepin-7-yl)oxy]-2-pyrazinecarboxamide;
4-[(3-Cyclobutyl-2,3,4,5-tetrahydro-1H-3-benzazepin-7-yl)oxy]-N-methyl-3-(methyloxy)benzamide;

2-[(3-Cyclobutyl-2,3,4,5-tetrahydro-1H-3-benzazepin-7-yl)oxy]benzonitrile;
3-[(3-Cyclobutyl-2,3,4,5-tetrahydro-1H-3-benzazepin-7-yl)oxy]-N-methyl-4-(methyloxy)benzamide;
3-Chloro-4-[(3-cyclobutyl-2,3,4,5-tetrahydro-1H-3-benzazepin-7-yl)oxy]-N-methylbenzamide;
4-[(3-Cyclobutyl-2,3,4,5-tetrahydro-1H-3-benzazepin-7-yl)oxy]-N,3-dimethylbenzamide;
3-Cyclobutyl-8-[(phenylmethyl)oxy]-2,3,4,5-tetrahydro-1H-3-benzazepine-7-carbonitrile;
3-Cyclobutyl-7-[(2-fluorophenyl)oxy]-2,3,4,5-tetrahydro-1H-3-benzazepine;
4-[(3-Cyclobutyl-2,3,4,5-tetrahydro-1H-3-benzazepin-7-yl)oxy]-3-fluorobenzonitrile;
4-[(3-Cyclobutyl-2,3,4,5-tetrahydro-1H-3-benzazepin-7-yl)oxy]-3-fluorobenzoic acid;
4-[(3-Cyclobutyl-2,3,4,5-tetrahydro-1H-3-benzazepin-7-yl)oxy]-3-fluoro-N-methylbenzamide;
3-Cyclobutyl-7-[(2-fluoro-4-iodophenyl)oxy]-2,3,4,5-tetrahydro-1H-3-benzazepine;
1-{4-[(3-Cyclobutyl-2,3,4,5-tetrahydro-1H-3-benzazepin-7-yl)oxy]-3-fluorophenyl}-2-pyrrolidinone;
N-{4-[(3-Cyclobutyl-2,3,4,5-tetrahydro-1H-3-benzazepin-7-yl)oxy]-3-fluorophenyl}acetamide;
1-[3-(3-Cyclobutyl-2,3,4,5-tetrahydro-1H-benzo[d]azepin-7-yloxy)-phenyl]-1-pyrrolidin-1-yl-methanone;
5-[(3-Cyclobutyl-2,3,4,5-tetrahydro-1H-3-benzazepin-7-yl)oxy]-N-(tetrahydro-2H-pyran-4-yl)-2-pyridinecarboxamide;
3-Cyano-4-[(3-cyclobutyl-2,3,4,5-tetrahydro-1H-3-benzazepin-7-yl)oxy]-N-methylbenzamide;
3-Cyclobutyl-7-{[6-(4-morpholinylcarbonyl)-3-pyridazinyl]oxy}-2,3,4,5-tetrahydro-1H-3-benzazepine;
6-[(3-Cyclobutyl-2,3,4,5-tetrahydro-1H-3-benzazepin-7-yl)oxy]-N-methyl-3-pyridazinecarboxamide;
6-[(3-Cyclobutyl-2,3,4,5-tetrahydro-1H-3-benzazepin-7-yl)oxy]-N-ethyl-N-methyl-3-pyridazinecarboxamide;
3-Cyclobutyl-7-{[4-(4-morpholinyl)-4-oxobutyl]oxy}-2,3,4,5-tetrahydro-1H-3-benzazepine;
3-Cyclobutyl-7-[(1-{[4-(4-morpholinyl)phenyl]carbonyl}-4-piperidinyl)oxy]-2,3,4,5-tetrahydro-1H-3-benzazepine;
3-Cyclobutyl-7-{[1-(cyclopropylacetyl)-4-piperidinyl]oxy}-2,3,4,5-tetrahydro-1H-3-benzazepine;
3-Cyclobutyl-7-[(1-{[(2R,6S)-2,6-dimethyl-4-morpholinyl]carbonyl}-4-piperidinyl)oxy]-2,3,4,5-tetrahydro-1H-3-benzazepine;
3-Cyclobutyl-7-{[trans-4-(4-morpholinylcarbonyl)cyclohexyl]oxy}-2,3,4,5-tetrahydro-1H-3-benzazepine;
3-Cyclobutyl-7-{[6-(4-morpholinyl)-2-pyrazinyl]oxy}-2,3,4,5-tetrahydro-1H-3-benzazepine;
or a pharmaceutically acceptable salt thereof.

19. The method of claim 18 wherein said compound is:
5-(3-Cyclobutyl-2,3,4,5-tetrahydro-1H-benzo[d]azepin-7-yloxy)-pyrazine-2-carboxylic acid methyl amide;
or a pharmaceutically acceptable salt thereof.

\* \* \* \* \*